US008084459B2

(12) United States Patent
Kok et al.

(10) Patent No.: US 8,084,459 B2
(45) Date of Patent: *Dec. 27, 2011

(54) SUBSTITUTED QUINAZOLINONES FOR TREATING NEUROLOGICAL CONDITIONS

(75) Inventors: Gaik Beng Kok, North Carlton (AU); Brenda Kwan Yi Leung, Balwyn (AU)

(73) Assignee: Prana Biotechnology Ltd, Parkville, Victoria (AU)

( * ) Notice: Subject to any disclaimer, the term of this patent is extended or adjusted under 35 U.S.C. 154(b) by 103 days.

This patent is subject to a terminal disclaimer.

(21) Appl. No.: 11/547,056

(22) PCT Filed: Apr. 1, 2005

(86) PCT No.: PCT/AU2005/000477
§ 371 (c)(1),
(2), (4) Date: Nov. 13, 2007

(87) PCT Pub. No.: WO2005/095360
PCT Pub. Date: Oct. 13, 2005

(65) Prior Publication Data
US 2008/0119470 A1    May 22, 2008

(30) Foreign Application Priority Data

| Apr. 2, 2004 | (AU) | 2004901802 |
| Apr. 2, 2004 | (AU) | 2004901804 |
| Dec. 24, 2004 | (AU) | 2004907359 |

(51) Int. Cl.
*A61K 31/517* (2006.01)
(52) U.S. Cl. ..................... 514/266.3; 544/287
(58) Field of Classification Search ............ 514/266.3; 544/287
See application file for complete search history.

(56) References Cited

U.S. PATENT DOCUMENTS

| 5,756,502 A | 5/1998 | Padia |
| 6,337,332 B1 | 1/2002 | Carpino |
| 2002/0161014 A1 | 10/2002 | Sadhu et al. |
| 2004/0048853 A1 | 3/2004 | Bergnes |
| 2005/0043239 A1 | 2/2005 | Douangpanya et al. |
| 2005/0282834 A1 | 12/2005 | Malik et al. |

FOREIGN PATENT DOCUMENTS

| GB | 713767 | 8/1954 |
| WO | WO 97/10221 | 3/1997 |
| WO | WO 98/21186 | 5/1998 |
| WO | WO 98/26664 | 6/1998 |
| WO | WO 00/24707 A1 | 5/2000 |
| WO | WO 01/16114 A2 | 3/2001 |
| WO | WO 01/30768 A1 | 5/2001 |
| WO | WO 01/81346 A2 | 11/2001 |
| WO | WO 01/98278 A1 | 12/2001 |
| WO | WO 02/48115 A2 | 6/2002 |
| WO | WO 03/039460 A2 | 5/2003 |
| WO | WO 03/043961 A2 | 5/2003 |
| WO | WO 03/043995 A1 | 5/2003 |
| WO | WO 03/070701 A2 | 8/2003 |
| WO | WO 03/076418 A1 | 9/2003 |
| WO | WO 03/084544 A2 | 10/2003 |
| WO | WO 2004/031161 A1 | 4/2004 |
| WO | WO 2005/016348 A1 | 2/2005 |
| WO | WO 2005/016349 A1 | 2/2005 |
| WO | WO 2005/051922 A1 | 6/2005 |
| WO | WO 2005/067901 A2 | 7/2005 |
| WO | WO 2005/095360 A1 | 10/2005 |
| WO | WO 2005/011789 A1 | 12/2005 |
| WO | WO 2005/112935 A1 | 12/2005 |
| WO | WO 2005/115993 A1 | 12/2005 |
| WO | WO 2005/120511 A1 | 12/2005 |

OTHER PUBLICATIONS

Jordan, V. C. Nature Reviews: Drug Discovery, 2, 2003, p. 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Vippagunta, et al. Advanced Drug Delivery Reviews, 48, 2001, p. 18.*
Wolff, Manfred E., Ed. Burger's Medicinal Chemistry and Drug Discovery—Fifth Edition, New York: John Wiley & Sons, 1996, vol. 1, pp. 975-976.*
Iyer, et al. J. Sci. Ind. Res., 20C, 1961, 175-177.*
STN File CA, abstract No. 57:56272 & R.N. Iyer and M.L. Dhar, Journal of Scientific & Industrial Research (1961), 20C, 175-177.
R.N. Iyer et al., "Studies in Potential Amodbicides: Part VII-Synthesis of Some 3-Alkyl-2-styryl-8-hydroxy- (& 8-methoxy) -4-quinazolones", J. Sci. Industr. Res., 17C, (1958).

* cited by examiner

*Primary Examiner* — James O Wilson
*Assistant Examiner* — Douglas M Willis
(74) *Attorney, Agent, or Firm* — Scully, Scott, Murphy & Presser, P.C.

(57) ABSTRACT

Compounds of the formula

I

[chemical structure: quinazolinone with substituents $R^5$, X, $R^3$, $R^7$, OH, $R^2$]

or salts, tautomers or isomers thereof, are useful for treating neurological conditions, especially neurodegenerative disorders, such as Alzheimer's disease.

5 Claims, No Drawings

SUBSTITUTED QUINAZOLINONES FOR TREATING NEUROLOGICAL CONDITIONS

The present invention relates to neurologically-active compounds, processes for their preparation and their use as pharmaceutical or veterinary agents, in particular for the treatment of neurological conditions, more specifically neurodegenerative conditions such as Alzheimer's disease.

BACKGROUND

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in Australia or in any other country.

The life span is thought to be biologically fixed for each species, and the length of the human life span is uncertain, but may be up to 120 years. Since life expectancy has risen significantly in this century, the elderly are an increasing segment of our population, and their health care needs will continue to grow for decades.

Although normal aging is characterized by modest reductions in the mass and volume of the human brain, which may be due to the atrophy and/or death of brain cells, these changes are far more profound in the brains of patients who succumb to a neurodegenerative condition. Most of these conditions are sporadic (i.e., not due to genetic mutations) and of unknown cause, but hundreds of different mutations in many genes have been shown to cause familial (inherited) variants of several neurodegenerative conditions. Many of the dozen or more genes that harbor these mutations were discovered in the quest to determine the genetic basis of neurodegenerative conditions just in the last ten years. Neurodegenerative conditions evolve gradually after a long period of normal brain function, due to progressive degeneration (i.e., nerve cell dysfunction and death) of specific brain regions. Since symptomatic expression of disease occurs when nerve cell loss exceeds a "threshold" for the continuing function (e.g., memory, movement) performed by the affected brain region, the actual onset of brain degeneration may precede clinical expression by many years.

Intellectual and higher integrative cognitive faculties become progressively impaired and interfere with activities of daily living in neurological conditions resulting in dementia. The precise prevalence of dementia in the elderly population is unknown, but may be 15% of people over 65 years old with 5% severely and 10% mildly to moderately demented. The prevalence of severe dementia increases from 1% at 65 years to 45% at 85 years. There are many causes of dementia, but Alzheimer's Disease (AD) accounts for 50% of demented patients over 65 years of age.

AD is a primary degenerative disease of the brain. It is characterized by progressive decline of cognitive functions such as memory, thinking, comprehension, calculation, language, learning capacity and judgement. Dementia is diagnosed when these declines are sufficient to impair personal activities of daily living. AD shows an insidious onset with slow deterioration. This disease needs to be clearly differentiated from age-related normal decline of cognitive functions. The normal decline is much less, much more gradual and leads to milder disabilities. The onset of AD is usually after 65 years of age, although earlier onset is not uncommon. As age advances, the incidence increases rapidly (it roughly doubles every 5 years). This has obvious implications for the total number of individuals living with this disorder as life expectancy increases in the population.

The aetiology of dementia of AD is unclear. There is considerable evidence of a heritable predisposition for some forms of AD (reviewed in St George-Hyslop, 2000), and the expression of certain isoforms of ApoE has also been linked to a higher risk of AD (Corder et al, 1993; Czech et al 1994). The toxic accumulation of aluminium has been suggested as a causative agent in AD, although this hypothesis has now been largely superseded. The brains of AD patients display abnormal deposits which include β-amyloid protein (Aβ).

Aβ is known to be present in the brains of individuals with certain neurodegenerative diseases, but it is not known whether it is symptomatic of an underlying disease process, or is actually involved in the aetiology of the disease. For example, some authors believe that the Aβ deposits may be indicative of a normal brain defense mechanism, in which the brain attempts to sequester the Aβ; such deposits can be present in the brains of normal individuals. There is a mutation of tau protein in which neurofibrillary tangles, but no amyloid plaques are present in the brain; this condition is known as tauopathy.

One proposed approach to AD therapy is to inhibit production of Aβ in the brain. Proteolytic cleavage of APP by BACE1 and γ-secretase generates the full-length Aβ, which is then released from cells (Nunan and Small, 2000). Therefore inhibitors of either BACE1 or γ-secretase may be of therapeutic value. Alternatively, a number of studies have shown that cholesterol can influence Aβ release (Simons et al., 1998; Hartmann, 2001; Fassbender et al., 2001; Frears et al., 1999; Friedhoff et al., 2001). However, there is some disagreement in the art as to the value of lowering cholesterol levels, and some workers consider that cholesterol is actually beneficial. For example, Ji et al, (2002) have suggested that the binding of Aβ to cholesterol might prevent Aβ toxicity by inhibiting its oligomerization.

In an alternative approach, it has been proposed that by unraveling the proteolytic processing of the amyloid precursor protein (APP), which generates the Aβ amyloid monomer, a number of possible therapeutic targets may be possible (Shearman et al., 2000; Sinha et al., 1999), and this approach is in an early stage of clinical development. Attempts to promote the clearance of Aβ from the brain through immunization with Aβ, while efficacious in a transgenic mouse model for AD (Schenk et al 1999), have been found to have significant adverse effects (Brower, 2002).

It has also been suggested that deposition of amyloid-like fibrils may also be important in other neurodegenerative diseases. These include Parkinson's disease, dementia with Lewy body formation, multiple system atrophy, Hallerboden-Spatz disease, and diffuse Lewy body disease.

One of the competing theories of the aetiology of AD is that the causative step(s) lies within the pathway of the intracerebral biogenesis and accumulation of the Aβ amyloid protein (see recent reviews by Selkoe, 2001; Beyreuther et al., 2001; Bush, 2001). However, to date no drugs or agents which target this pathway have been demonstrated to have a lasting effect on modifying the clinical expression of the disease or in preventing or ameliorating the decline in cognitive function associated with neurodegenerative disorders, including Alzheimer's disease.

A further hypothesis is that AD is caused by the toxic accumulation of Aβ amyloid, due in part to excess binding of copper and zinc, metal ions which are abundant in the regions most affected. Moreover, it has been suggested that when $Zn^{2+}$ and $Cu^{2+}$ ions interact with Aβ, aggregation of Aβ into fibrils and plaques occurs (Atwood et al., 1998); confirmed by recent data from animals deficient in synaptic $Zn^{2+}$ (Lee et al., 2002). It has also been suggested that redox-active $Cu^{2+}$-Aβ interactions can generate $H_2O_2$ from $O_2$ (Huang et al., 1999). Both $Cu^{2+}$ and $Zn^{2+}$ have been shown to affect Aβ-lipid membrane interactions (Curtain et al., 2001).

The brain is an organ that concentrates metal ions and recent evidence suggests that a breakdown in metal homeostasis plays a critical role in a variety of age-related neurodegenerative diseases. Common features of these diseases include the deposition of misfolded protein (each disease has its own specific amyloid protein) and substantial cellular damage as a result of oxidative stress. Indeed data is now rapidly accumulating that metallochemical reactions could emerge as the common denominator underlying amyloidogenic neurological disorders such as Alzheimer's disease, amylotrophic lateral sclerosis (ALS), prion diseases—including Creutzfeldt-Jakob Disease (CJD), transmissible spongioform encephalopathies (TSE), cataracts, mitochondrial disorders, Parkinson's disease and Huntington's disease. In these instances, the pathological aggregation of a specific protein is promoted by abnormal redox activity in a physiological environment typified by the presence of transition metals and available reducing agents. [Bush, 2000 (Curr Opin Chem. Biol. 2000 April; 4(2):184-91)].

A method of treatment of AD using iodochlorohydroxyquinoline an antibiotic [also known as clioquinol (CQ)], is disclosed and claimed in U.S. Pat. Nos. 5,994,323 and 6,001,852 by P. N. Geromylatos S. A. and in U.S. patent application Ser. No. 09/972,913 by Bush et al. CQ was withdrawn as an antibiotic in 1970, because of its association with an uncommon neurological syndrome, subacute myelo-optic neuropathy (SMON), which was observed only in Japan in the 1960s, in patients thought to have received the drug over long periods and probably at doses higher than those recommended at the time (Shiraki, 1975). However, recent evidence suggests that SMON was caused by an overuse-related vitamin B12 deficiency in an exceptionally vulnerable population, and therefore could be rehabilitated for study in a clinical setting (Yassin et al., 2000; Bush and Masters, 2001).

However, no in vivo results in animal models or in humans are provided in the Geromylatos and Bush patents. U.S. Pat. No. 5,994,323 discloses a composition comprising CQ and Vitamin B12, and its use for the treatment of "diseases or disorders responsive to CQ administration while inhibiting detrimental side effects" of CQ. These diseases include AD. U.S. Pat. No. 6,001,852 discloses a method of treatment of AD using CQ, preferably together with Vitamin B12. Both U.S. Pat. Nos. 5,994,323 and 6,001,852 suggest a dosage of 10-750 mg per day; U.S. Pat. No. 5,994,323 recommends that if treatment is over a long period CQ should be given intermittently, for up to 3 weeks at a time followed by a "wash-out" period of 1-4 weeks.

In U.S. application Ser. No. 09/972,913 CQ is exclusively referred to in terms of its ability to disaggregate Aβ deposits. No other mechanism of neurotoxicity is discussed. PCT/US99/05291 by General Hospital Corporation discloses the use of CQ in combination with specific copper and zinc chelators to promote dissolution of amyloid plaques and inhibition of amyloid plaque formation and/or the production of ROS by Aβ.

U.S. Pat. No. 6,001,852 also suggests that a composition comprising CQ and Vitamin B12 could be used in the treatment of Parkinson's disease; however, in this context it is suggested that CQ acts primarily via clearing iron from the substantia nigra.

The efficacy of CQ in the treatment of AD rests upon its ability to enter the CNS and then sequester the transition metals Cu, Zn and Fe from various Aβ entities thereby reducing Aβ toxicity and liberating it for clearance. The effectiveness of CQ is restricted by its poor aqueous solubility which limits its oral bioavailability. CQ is also known to undergo considerable conjugative metabolism and has a history of toxicity as discussed above. The fact that CQ is a bidentate metal ligand makes necessary the commitment of at least two molecules for every metal ion captured.

SUMMARY

The present invention provides a means of treating neurological conditions including those characterised by the abnormal reaction between proteins and metals.

International Patent Publication No. WO2004/031161 describes heterocyclic compounds having two fused 6-membered rings with a nitrogen at position 1 and a hydroxy or mercapto group at position 8 with at least one ring being aromatic. These compounds are useful as pharmaceutical or veterinary agents, in particular for the treatment of neurological conditions, more specifically neurogenerative conditions such as Alzheimer's disease.

We have now developed heterocyclic compounds having two fused 6-membered rings with nitrogen atoms at positions 1 and 3, a carboxy group at position 4 and a hydroxy group at position 8 with both rings being aromatic through the collective optimization of one or more of the following properties:

(a) metal chelation (as hereinafter defined);

(b) aqueous solubility;

(c) reduced cell toxicity;

(d) amyloid dispersion properties;

(e) membrane permeability appropriate for CNS penetration; and (f) metabolic stability.

These compounds fall within the generic scope of International Patent Publication No. 2004/031161, but are not specifically disclosed therein and include examples of therapeutics which are concentrated in the CNS through active transport, contain antioxidant activity in addition to their metal chelation properties which in some cases leads to enhanced metal chelation properties and demonstrate a prodrug strategy which masks the 8-hydroxy moiety to favour CNS penetration and make use of the known esterase activity which resides on the inner surface of the blood brain barrier (BBB).

While not wishing to be bound by any theory, it is believed that the nature of the substituents at positions 2 and 3 may be important in enhancing plaque disaggregation. It is preferable that these substituents are planar in 3D terms. Planar substituents on the ring system allow both the free ligand and the metal chelate to more effectively interact with, and disaggregate, the plaques.

According to the present invention there is provided a compound of the formula I $$\text{I}$$

[Structure: bicyclic ring with positions labeled 1-8, $R^5$ at position 5, X at position 4, $R^3$ on N at position 3, $R^2$ at position 2, N at position 1, OH at position 8, $R^7$ at position 7]

in which
$R^2$ is H or $CH_2NR^1R^4$ in which $R^1$ and $R^4$ are independently selected from H, optionally substituted $C_{1-6}$ alkyl and optionally substituted $C_{3-6}$ cycloalkyl;

$R^3$ is H; optionally substituted $C_{1-4}$ alkyl; optionally substituted $C_{1-4}$ alkenyl; optionally substituted $C_{3-6}$ cycloalkyl; optionally substituted 6-membered aryl optionally condensed with an optionally substituted 6 membered aryl or heteroaryl; optionally substituted saturated or unsaturated 5- or 6-membered N-containing heterocyclyl optionally condensed with an optionally substituted 6-membered aryl or heteroaryl; $(CH_2)_nR^6$ in which n is an integer of 1 to 6 and $R^6$ is optionally substituted $C_{1-4}$ alkyl, optionally substituted $C_{3-6}$ cycloalkyl, optionally substituted saturated or unsaturated 5- or 6-membered N-containing heterocyclyl or optionally substituted 6-membered aryl; $NR^8R^9$ in which $R^8$ and $R^9$ are independently selected from H, optionally substituted $C_{1-4}$ alkyl, optionally substituted $C_{3-6}$ cycloalkyl, optionally substituted saturated or unsaturated 5- or 6-membered N-containing heterocyclyl and optionally substituted 6-membered aryl; $NHCOR^{10}$ in which $R^{10}$ is optionally substituted $C_{1-4}$ alkyl, optionally substituted $C_{3-6}$ cycloalkyl, optionally substituted membered saturated or unsaturated 5- or 6-N-containing heterocyclyl or optionally substituted 6-membered aryl; $CH_2CONR^{11}R^{12}$ in which $R^{11}$ and $R^{12}$ are independently selected from H, optionally substituted $C_{1-6}$ alkyl, optionally substituted $C_{2-6}$ alkynyl and optionally substituted 5 or 6-membered N-containing heterocyclyl optionally condensed with optionally substituted 6-membered aryl; and $(CH_2)_mNHR^{13}$ in which $R^3$ is selected from optionally substituted $C_{1-6}$ alkyl and $SO_2R^{14}$ in which $R^{14}$ is selected from optionally substituted $C_{1-6}$ alkyl and optionally substituted 6-membered aryl and m is 1 to 6;

$R^5$ and $R^7$ are independently selected from H and halo; and
X is O or S,
with the provisos that:
(i) at least one of $R^2$ and $R^3$ is other than H;
(ii) at least one of $R^5$ and $R^7$ is halo; and
(iii) when X is O, $R^5$ and $R^7$ are $C^1$ and $R^2$ is H, then $R^3$ is not cyclopropyl,
salts, hydrates, solvates, derivatives, pro-drugs, tautomers and/or isomers thereof.

The invention also provides use of the compound of formula I as a pharmaceutical, preferably a neurotherapeutic or neuroprotective agent, more preferably an antiamyloidogenic agent. Preferably, the neurological condition is a neurodegenerative condition, more preferably neurodegenerative amyloidosis such as Alzheimer's disease or Parkinson's disease.

The compound of formula I is advantageously administered in the form of a pharmaceutical or veterinary composition together with a pharmaceutically or veterinarily acceptable carrier.

Thus, the present invention further provides a pharmaceutical or veterinary composition comprising the compound of formula I and a pharmaceutically or veterinarily acceptable carrier.

Further according to the present invention there is provided a method for the treatment, amelioration and/or prophylaxis of a neurological condition which comprises the administration of an effective amount of the compound of formula I to a subject in need thereof.

Still further according to the present invention there is provided use of the compound of formula I in the manufacture of a medicament for the treatment, amelioration and/or prophylaxis of a neurological condition.

The invention also provides use of the compound of formula I for the treatment, amelioration and/or prophylaxis of a neurological condition.

The invention further provides the compound of formula I for use in the treatment, amelioration and/or prophylaxis of a neurological condition.

The invention still further provides a process for the preparation of the compound of formula I defined above which comprises the steps of:

(a) reacting an optionally protected compound of formula V $$\text{V}$$

[Structure: benzene ring with $R^5$, $CO_2$, $NO_2$, OH, $R^7$ substituents]

in which $R^5$ and $R^7$ are as defined above with $H_2NR^3$ in which $R^3$ is as defined above to form an optionally protected compound of formula VII $$\text{VII}$$

[Structure: benzene ring with $R^5$, $CONHR^3$, $NO_2$, OH, $R^7$ substituents]

(b) reducing the compound of formula VII to form an optionally protected compound of formula VIII $$\text{VIII}$$

[Structure: benzene ring with $R^5$, $CONHR^3$, $NH_2$, OH, $R^7$ substituents]

(c) cyclisation of the compound of formula VIII to form an optionally protected compound of formula I in which $R^2$ is H; or (d) cyclisation of the compound of formula VIII in the presence of $R^2CHO$, $R^2CO_2H$ or $R^2C(OR^X)$ in which $R^X$ is optionally substituted $C_{1-4}$ alkyl or optionally substituted 6-membered aryl.

The invention also provides a process for the preparation of the compound of formula I as defined above in which $R^2$ is H which comprises the steps of:

(a) aminating an optionally protected compound of formula VI

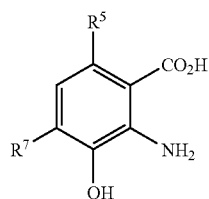

in which $R^5$ and $R^7$ are as defined above to form an optionally protected compound of formula IX

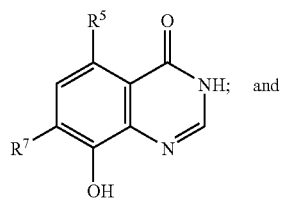

(b) reacting the compound of formula IX with $R^3$-L or $R^3OSO_2R^X$ in which L is a leaving group and $R^X$ is as defined above.

The invention also further provides a process for the preparation of the compound of formula I as defined above which $R^2$ is H which comprises the steps of:

(a) reacting the optionally protected compound of formula VI as defined above with a formulating agent to form either an optionally protected compound of formula X

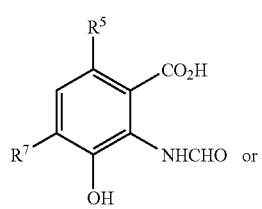

an optionally protected compound of formula XI

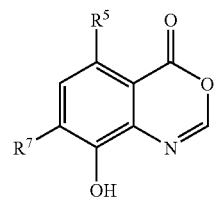

(b) reacting the compound of formula X or XI with an acylating agent containing $R^2$ to form an optionally protected compound of formula VII

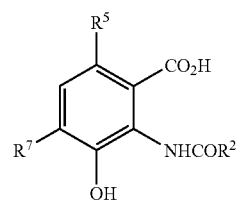

in which $R^2$ is as defined above or a compound of formula XIII

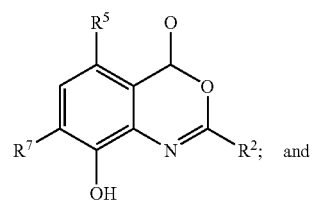

(c) reacting the compound of formula XII or XIII with $H_2NR^3$ in which $R^3$ is as defined above.

It will be appreciated that the protecting groups when present may be removed at any appropriate step of the processes described above.

We have also found a less complex process for preparing the precursor of the intermediates of formulae V and VI described hereinafter when both $R^5$ and $R^7$ are halo in a high yield.

Thus, further according to the present invention there is provided a process for the preparation of a compound of formula IV

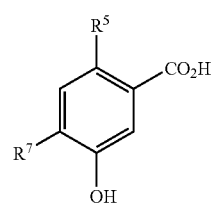

in which R⁵ and R⁷ are as defined in formula I above comprising the step of diazotisation of a compound of formula III

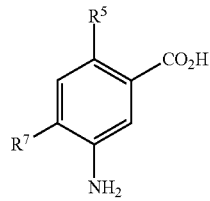

III

The compound of formula III is conveniently prepared by reducing a compound of formula II

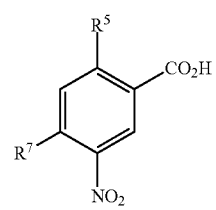

II in which R⁵ and R⁷ are as defined in formula IV above.

The compound of formula IV is a precursor in the preparation of intermediates of formulae V and VI

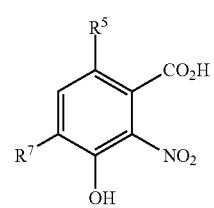

V

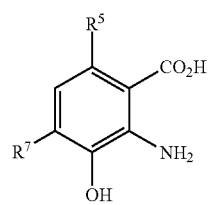

VI in which R⁵ and R⁷ are as defined in formula IV above which can be used to prepare the compounds of formula II.

Thus, the present invention also provides a process for the preparation of the compound of formula V as defined above which comprises the steps of:
(a) diazotisation of the compound of formula III as defined above to form a compound of formula IV as defined above; and
(b) nitration of the compound of formula IV.

The present invention further provides a process for the preparation of the compound of formula VI as defined above which comprises the steps of:
(a) diazotisation of the compound of formula IV as defined above to form a compound of formula V as defined above;
(b) nitration of the compound of formula VI to form the compound of formula V as defined above; and
(c) reducing the compound of formula V.

DETAILED DESCRIPTION

In the subject specification, except where the context requires otherwise due to express language or necessary implication, the words "comprise" or variations such as "comprises" or "comprising" are used in an inclusive sense, i.e. to specify the presence of the stated features but not to preclude the presence or addition of further features in various embodiments of the invention.

It must be noted that, as used in the subject specification, the singular forms "a", "an" and "the" include plural aspects unless the context clearly dictates otherwise. Thus, for example, reference to "a compound" includes a single compound, as well as two or more compounds; and so forth.

A preferred compound of formula I is a compound of formula IA:

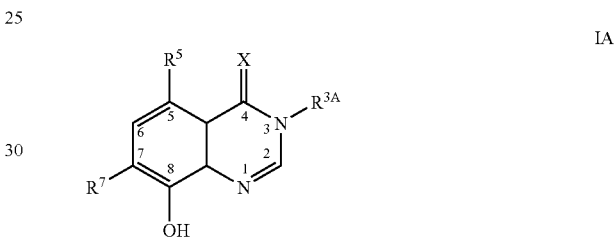

IA in which

R⁵, R⁷ and X are as defined in formula I above; and $R^{3A}$ is optionally substituted $C_{1-4}$ alkyl; optionally substituted $C_{1-4}$ alkenyl; an optionally substituted saturated or unsaturated 5- or 6-membered N-containing heterocyclyl optionally condensed with an optionally substituted 6-membered aryl or heteroaryl; $(CH_2)_n R^6$ in which n is 1 to 3 and $R^6$ is optionally substituted $C_{3-6}$ cycloalkyl or an optionally substituted saturated or unsaturated 5- or 6-membered N-containing heterocyclyl; $NR^8R^9$ in which $R^8$ is H and $R^9$ is H or optionally substituted $C_{1-4}$ alkyl or optionally substituted 6-membered aryl; $NHCOR^{10}$ in which $R^{10}$ is optionally substituted $C_{1-4}$ alkyl or optionally substituted 6-membered aryl.

Preferably R⁵ and R⁷ are both halo, more preferably chloro.

Illustrative examples of compounds of formula IA are shown below.

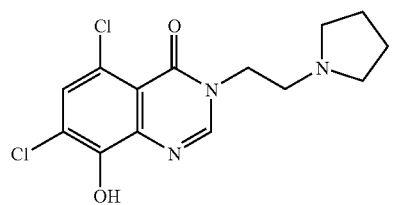

1075

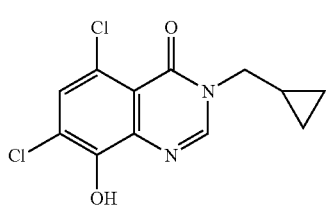 1076
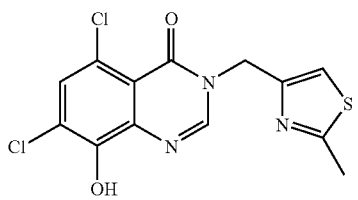 1084
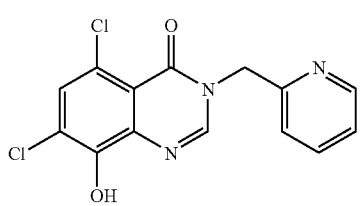 1077
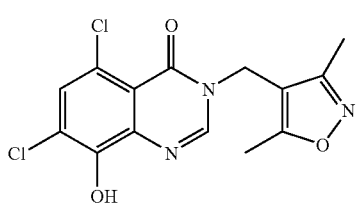 1085
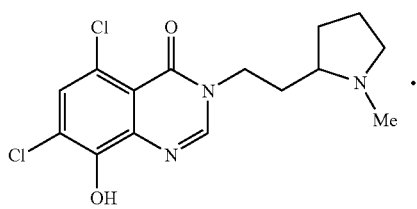 1078
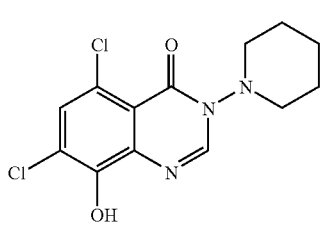 1086
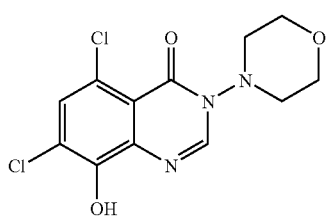 1080
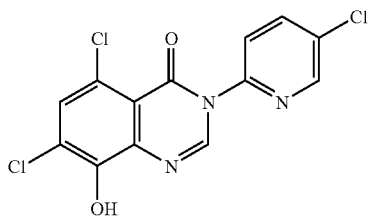 1087
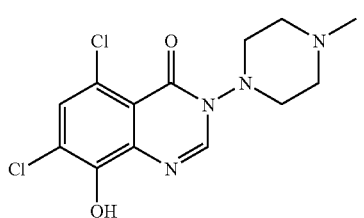 1081
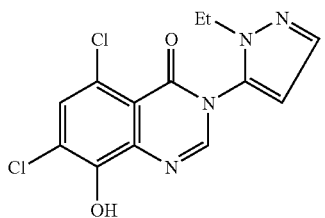 1088
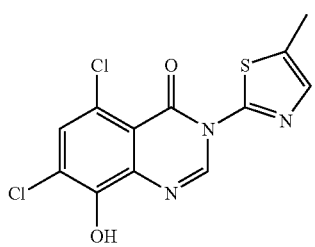 1082
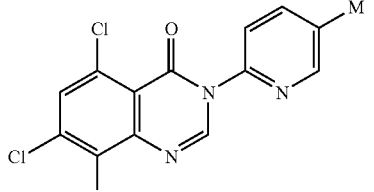 1089
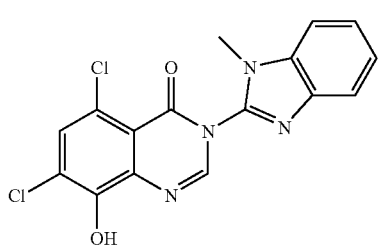 1083
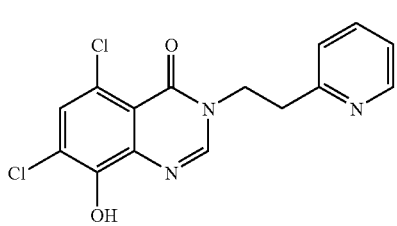 1091

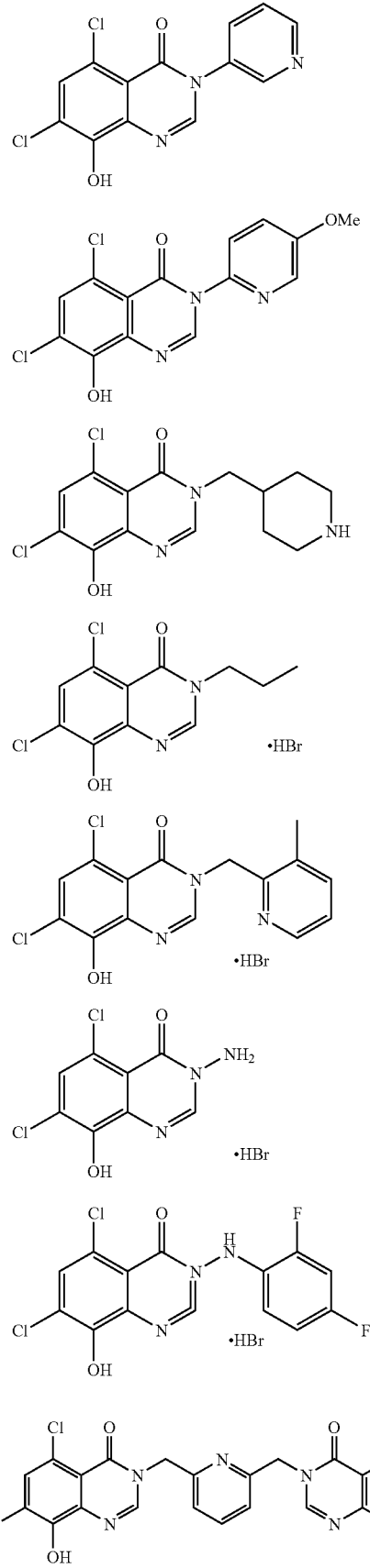
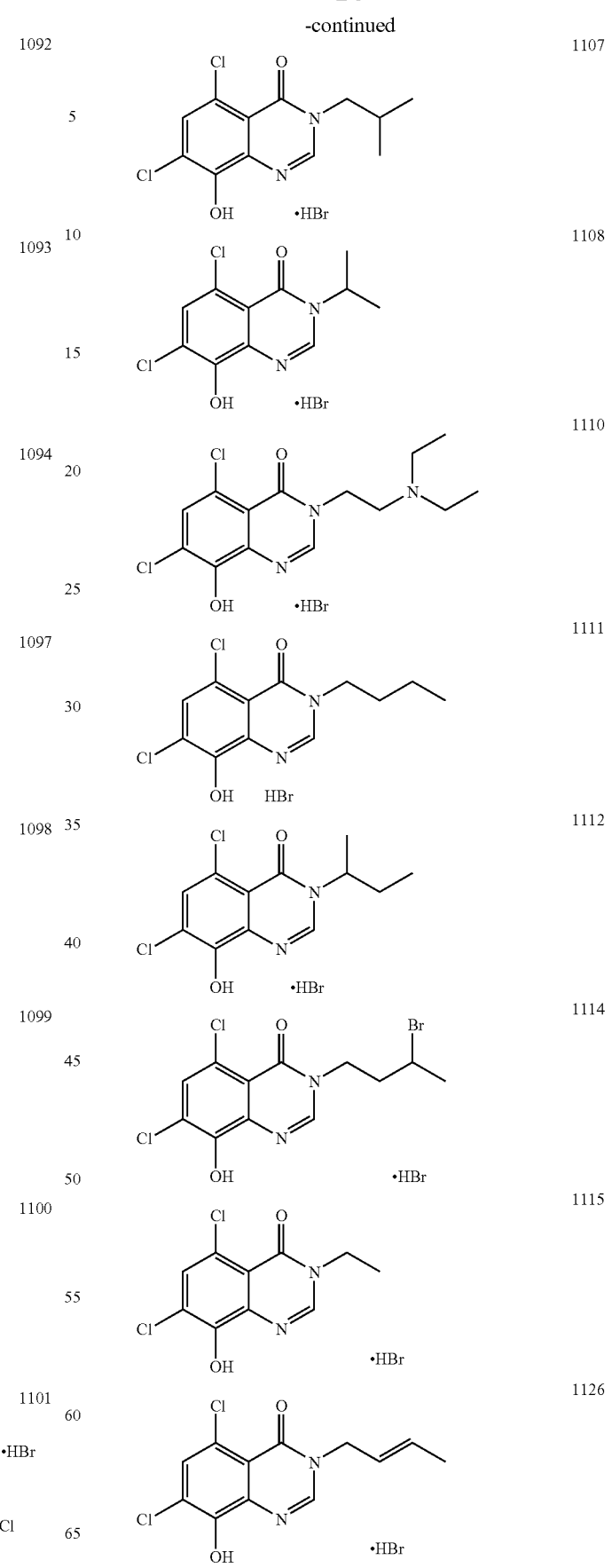

-continued

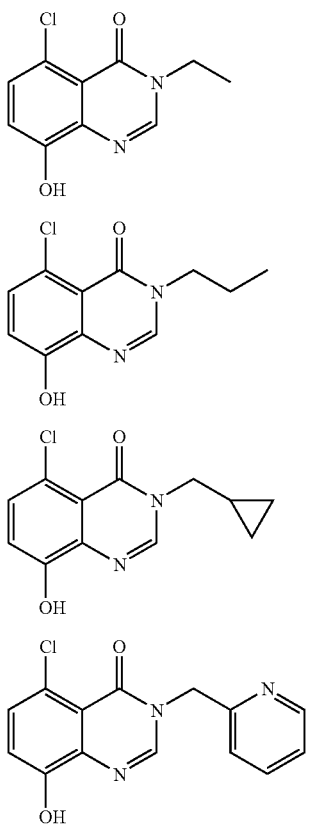

1130

1131

1132

1133

In the illustrative examples of the compounds of formula IA, compounds 1076, 1077, 1082, 1083, 1084, 1085, 1087, 1088, 1089, 1091, 1092, 1093, 1097, 1098, 1099, 1100, 1101, 1107, 1108, 1109, 1110, 1112, 1115 and 1126 possess planar substituents at position 3, such as, optionally substituted $C_{1-4}$ alkyl; optionally substituted $C_{1-4}$ alkenyl; optionally substituted saturated or unsaturated 5- or 6-membered N-containing heterocyclyl optionally condensed with an optionally substituted 6-membered aryl, $(CH_2)_nR^6$ in which n is 1 to 3 and $R^6$ is optionally substituted $C_{3-6}$ cycloalkyl or an optionally substituted saturated or unsaturated 5- or 6-membered N-containing heterocyclyl; and $NR^8R^9$ in which $R^8$ is H and $R^9$ is H or optionally substituted $C_{1-4}$ alkyl or optionally substituted 6-membered aryl. Of these planar compounds of formula IA, compounds 1100 and 1101 also possess very good disaggregation.

Another preferred compound of formula I is a compound

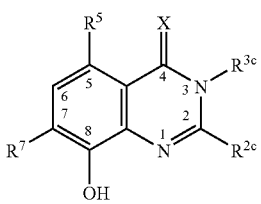

IB of formula IB:
in which $R^2$, $R^5$, $R^7$ and X are as defined in formula I above.
Preferably $R^2$ is $CH_2NR^1R^4$ in which $R^1$ and $R^4$ are independently selected from H, optionally substituted $C_{1-6}$ alkyl and optionally substituted $C_{3-6}$ cycloalkyl.

Preferably $R^5$ and $R^7$ are both halo, more preferably chloro.
Illustrative compounds of formula IB are shown below.

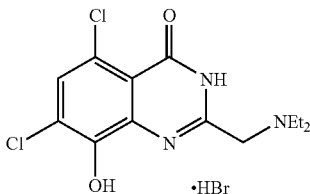

1128

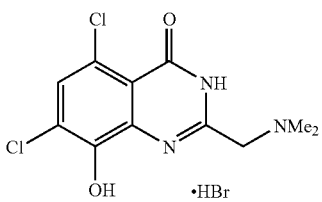

1147

Both of the illustrative examples of formula IB possess planar substituents at position 2, such as, $CH_2NR^1R^4$ in which $R^1$ and $R^4$ are independently selected from optionally substituted $C_{1-6}$ alkyl. Compound 1128 also possesses very good disaggregation.

A further subclass of the compound of formula I is a compound of formula IC:

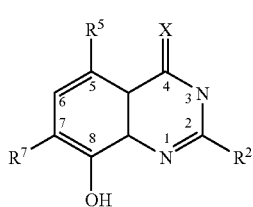

IC in which
$R^5$, $R^7$ and X are as defined in formula I above; and
$R^{1C}$ is $CH_2NR^1R^4$ in which $R^1$ and $R^4$ are independently selected from H and optionally substituted $C_{1-6}$ alkyl; and
$R^{3c}$ is optionally substituted $C_{1-4}$ alkyl.
Preferably $R^5$ and $R^7$ are both halo, more preferably chloro.
Illustrative compounds of formula IC are shown below.

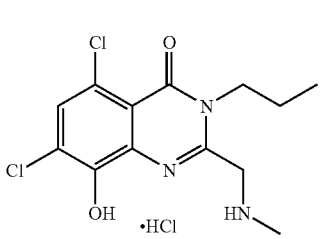

1095

-continued

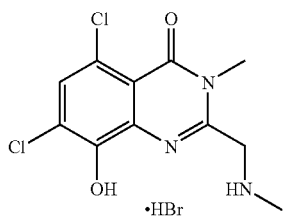

1161

The 8-hydroxyl group on the compounds of formula I may be blocked to form a prodrug, in particular an ester prodrug. The 8-hydroxy represents a principal site of metabolism for the compound of formula I: conjugation with glucuronic acid or sulphate gives a hydrophilic species ready to be excreted. Such conjugates probably do not pass the blood brain barrier. The ester prodrug may protect the compound of formula I from conjugation. Esterases integral to the blood brain barrier may then release the C8-hydroxy on passage through that barrier activating the compound for its role in the CNS.

While not wishing to be bound by theory, it is believed that substituents $R^3$ and $R^5$ generally have a limited effect, electronically or sterically, in the chelating properties of the compounds of the present invention. Substitution can therefore be used to modulate other parameters such as cytotoxicity and physicochemical properties including the number of hydrogen bond donors and acceptors, lipophilicity (ClogP, ElogP and LogD), solubility and polar surface area. Modulation of these parameters contribute to the optimisation of the pharmacokinetic profile of the compounds. It is also postulated that when substituents $R^2$ and $R^7$ in addition to modulating cytotoxicity and physicochemical properties could also affect activity if the substituent provides chelating properties.

The terms "$C_{1-6}$ alkyl" or "$C_{1-4}$ alkyl" used either alone or in compound words such as "optionally substituted $C_{1-4}$ alkyl" refers to straight chain or branched chain hydrocarbon groups having from 1 to 6 and 1 to 4 carbon atoms, respectively. Illustrative of such alkyl groups are methyl, ethyl, propyl, isopropyl, butyl, isobutyl, sec-butyl, tert-butyl, pentyl, neopentyl or hexyl, preferably methyl, ethyl or propyl.

The terms "$CH_2)_n$" or "$(CH_2)_m$" as used herein include both linear and branched chains.

The term "$C_{1-6}$ alkynyl" used either alone or in compound words such as "optionally substituted $C_{2-6}$ alkynyl" refers to straight chain or branched chain hydrocarbon groups having from 2 to 6 carbon atoms and having in addition one triple bond. Illustrative of such groups are ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

The term "$C_{3-6}$ cycloalkyl" used either alone or in compound words such as "optionally substituted $C_{3-6}$ cycloalkyl" refers to saturated carbocyclic groups having 3 to 6 carbon atoms. Illustrative of such groups are cyclopropyl, cyclobutyl, cyclopentyl and cyclohexyl, preferably cyclopropyl.

The term "unsaturated or saturated 5- or 6-membered N-containing heterocyclyl group optionally condensed with an optionally substituted 6-membered aryl" used either alone or in compound words such as "optionally substituted unsaturated or saturated 5- or 6-membered N-containing heterocyclyl group optionally condensed with an optionally substituted 6-membered aryl" refers to monocyclic or polycyclic heterocyclic groups containing at least one nitrogen atom and optionally other heteroatoms selected from sulphur and oxygen.

Suitable heterocyclic groups include N-containing heterocyclic groups, such as, unsaturated 5- or 6-membered heteromonocyclic groups containing 1 to 4 nitrogen atoms, for example, pyrrolyl, pyrrolinyl, imidazolyl, pyrazolyl, pyridyl, pyridinyl, pyrimidinyl, pyrazinyl, pyridazinyl, triazolyl or tetrazolyl;

saturated 5- or 6-membered heteromonocyclic groups containing 1 to 4 nitrogen atoms, such as, pyrrolidinyl, imidazolidinyl, piperidino or piperazinyl;

unsaturated condensed heterocyclic groups containing 1 to 5 nitrogen atoms, such as indolyl, isoindolyl, indolizinyl, benzimidazolyl, quinolyl, isoquinolyl, indazolyl, benzotriazolyl or tetrazolopyridazinyl;

unsaturated 5- or 6-membered heteromonocyclic group containing 1 to 2 oxygen atoms and 1 to 3 nitrogen atoms, such as, oxazolyl, isoxazolyl or oxadiazolyl;

saturated 5- or 6-membered heteromonocyclic group containing 1 to 2 oxygen atoms and 1 to 3 nitrogen atoms, such as, morpholinyl;

unsaturated 5- or 6-membered heteromonocyclic group containing 1 to 2 sulphur atoms and 1 to 3 nitrogen atoms, such as, thiazolyl or thiadiazolyl; and saturated 3 to 6-membered heteromonocyclic group containing 1 to 2 sulphur atoms and 1 to 3 nitrogen atoms, such as, thiazolidinyl.

Preferably the heterocyclyl is an unsaturated 5 or 6-membered heteromonocyclic group containing 1 to 3 nitrogen atoms such as pyrazolyl, pyridinyl or pyrimidinyl; a saturated 5 or 6-membered heteromonocyclic group containing 1 to 4 nitrogen atoms such as pyrrolidinyl or piperazinyl; an unsaturated condensed heterocyclic group containing 1 to 5 nitrogen atoms such as benzimidazolyl; a saturated 5 or 6-membered heteromonocyclic group containing 1 to 2 oxygen atoms and 1 to 3 nitrogen atoms such as morpholinyl; or an unsaturated 5- or 6-membered heteromonocyclic group containing 1 to 2 sulphur atoms and 1 to 3 oxygen atoms, such as thiazolyl.

The term "6-membered aryl" used either alone or in compound words such as "optionally substituted 6-membered aryl" denotes a 6-membered carbocyclic aromatic group. Illustrative of such aryl groups are phenyl. Preferably, the aryl is optionally substituted phenyl such as 4-halophenyl, more preferably 4-fluorophenyl.

The term "6-membered hetroaryl" used either alone or in compound words such as "optionally substituted 6-membered hetroaryl" denotes a 6-membered aromatic heterocycle containing one or more heteroatoms. Examples include pyridyl pyrazinyl, pyrimidinyl and pyridazinyl, each of which may be optionally substituted by methyl or methoxy.

The term "halo" refers to fluorine, chlorine, bromine or iodine, preferably fluorine, iodine or chlorine, more preferably chlorine.

The term "optionally substituted" refers to a group which may or may not be further substituted with one or more groups selected from alkyl, alkenyl, alkynyl, aryl, aldehyde, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocyloxy, heterocyclamino, haloheterocyclyl, alkylsulphenyl, arylsulphenyl, carboalkoxy, carboaryloxy, mercapto, alkylthio, benzylthio, acylthio, phosphorus-containing groups and the like. Preferably, the optional substituent is $C_{1-4}$ alkyl, hydroxy, fluorine, $C_{1-4}$ alkoxy or $C_{1-4}$ acyl.

The term "protecting group" refers to an introduced functionality which renders a particular functional groups, such as a hydroxy, amino, carbonyl or carboxy group, unreactive under selected conditions and which may later be optionally removed to unmask the functional group. A hydroxy protecting group is one which can temporarily render a hydroxy group unreactive. A hydroxy protecting group refers to a hydroxy group which has temporarily been rendered unreactive by a hydroxy protecting group. A protected phenyl group is taken to be one in which attached reactive substituents, such as OH, $NH_2$, are protected by a protecting group. Suitable protecting groups are known in the art and are described in Protective Groups in Organic Synthesis, Third Edition, T. W. Greene and P. G. White, John Wiley & Sons, Inc., 1999, (the contents of which are incorporated herein by reference) as are methods for their installation and to protect a hydroxy group include, but are not limited to, silyl groups (eg trimethylsilyl, t-butyldimethylsilyl, t-butyldiphenylsilyl), benzyl groups (eg benzyl, methoxybenzyl, nitrobenzyl), alkyl groups (eg methyl, ethyl, n- and i-propyl, and n-, sec- and t-butyl) and acyl groups (eg acetyl and benzoyl).

The leaving group may be of any suitable known type, such as, for example, those leaving groups disclosed in J. March, "Advanced Organic Chemistry: Reactions, Mechanisms and Structure" $4^{th}$ Edition, pp 352-357, John Wiley & Sons, New York, 1992 which is incorporated herein by reference. Preferably, the leaving group is halogen.

The term "metal chelator" is used herein in its broadest sense and refers to compounds having two or more donor atoms capable of binding to a metal atom, preferably Cu, Zn or Fe wherein at least two of the donor atoms are capable of simultaneous binding to the metal atom and the resultant metal complex has a thermodynamic stability greater than or equal to that of the metal ion: biological ligand complex. The use of metal chelators as treatments for neurological disorders in the present invention is distinguished from the previously known concept of "chelation therapy". "Chelation therapy" is a term associated clinically with the removal of bulk metals such as in Wilson's disease, -thallesemia and haemochromatosis. The break down in metal homeostasis in these diseases can be described as a catastrophic event much like a dam bursting leading to overwhelming flooding of the problem metal. The mechanism of action of such compounds is that bulk metal is sequestered by the chelators and cleared by excretion. By way of comparison the breakdown in metal homeostasis associated with neurological conditions of the present invention is more akin to the constant drip of a leaky tap, which if left long enough will eventually cause local damage over a long period of time. The intention of the "metal chelator" of the present invention is to disrupt an abnormal metal-protein interaction to achieve a subtle repartitioning of metals and a subsequent normalization of metal distribution with the aim that once the toxic cycle is short-circuited, endogenous clearance processes can cope more effectively with the accumulating amyloidogenic protein.

The salts of the compound of formula I are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

In addition, some of the compounds of the present invention may form solvates with water or common organic solvents. Such solvates are encompassed within the scope of the invention.

Preferably the derivative is a "pharmaceutically acceptable derivative". By "pharmaceutically acceptable derivative" is meant any pharmaceutically acceptable salt, hydrate, ester, ether, amide, active metabolite, analogue, residue or any other compound which is not biologically or otherwise undesirable and induces the desired pharmacological and/or physiological effect.

The term "pro-drug" is used herein in its broadest sense to include those compounds which are converted in vivo to the compound of formula I. Use of the pro-drug strategy optimises the delivery of the drug to its site of action, for example, the brain. In one aspect, the term refers to the presence of a $C_{1-6}$ alkyl or arylester moiety which is designed to resist hydrolysis until the pro-drug has crossed the BBB, where esterases on the inner surface of the BBB act to hydrolyse the ester and liberate the C8 hydroxyl of the compound of formula I. In a second aspect, the term refers to the attachment at position 2 of an antioxidant group, in particular the 3,4,5-trimethoxyphenyl moiety or derivatives thereof. Exposure to the prooxidative environment of the brain will then lead to hydroxylation of the 3,4,5-trimethoxyphenyl group to give a 2-hydroxy-3,4,5-trimethoxyphenyl substituent, the hydroxyl group of which acts to enhance the chelation properties of the compound of formula I.

The term "antioxidant" is used herein in its broadest sense and refers to a group which has the capacity to react with a reactive oxygen species such as a hydroxyl radical in such a way as to generate a non toxic product.

Examples include phenols such as 3,4,5-trimethoxyphenyl and 3,5-di-t-butyl-4-hydroxyphenyl, indole amines such as melatonin and flavonoids. Other examples may be found the literature (Wright, 2001; Karbownik, 2001; Gilgun-Sherki, 2001).

The term "tautomer" is used herein in its broadest sense to include compounds of formula I which are capable of existing in a state of equilibrium between two isomeric forms. Such compounds may differ in the bond connecting two atoms or groups and the position of these atoms or groups in the compound.

The term "isomer" is used herein in its broadest sense and includes structural, geometric and stereo isomers. As the compound of formula I may have one or more chiral centres, it is capable of existing in enantiomeric forms.

The compositions of the present invention comprise at least one compound of formula I together with one or more pharmaceutically acceptable carriers and optionally other therapeutic agents. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product.

The term "neurological condition" is used herein in its broadest sense and refers to conditions in which various cell types of the nervous system are degenerated and/or have been damaged as a result of neurodegenerative disorders or injuries or exposures. In particular, compound of formula I can be used for the treatment of resulting conditions, in which damage to cells of the nervous system has occurred due to surgical interventions, infections, exposure to toxic agents, tumours, nutritional deficits or metabolic disorders. In addition, the compound of formula I can be used for the treatment of the sequelae of neurodegenerative disorders, such as Alzheimer's disease, Parkinson's disease, multiple sclerosis, amylotrophic lateral sclerosis, epilepsy, drug abuse or drug addiction (alcohol, cocaine, heroin, amphetamine or the like), spinal cord disorders and/or injuries, dystrophy or degeneration of the neural retina (retinopathies) and peripheral neuropathies, such as diabetic neuropathy and/or the peripheral neuropathies induced by toxins.

The term "neurodegenerative disorder" as used herein refers to an abnormality in which neuronal integrity is threatened. Neuronal integrity can be threatened when neuronal cells display decreased survival or when the neurons can no longer propagate a signal.

Neurological disorders that can be treated with the compound of the present invention include acute intermittent porphyria; adriamycin-induced cardiomyopathy; AIDS dementia and HIV-1 induced neurotoxicity; Alzheimer's disease; amylotrophic lateral sclerosis; atherosclerosis; cateract; cerebral ischaemia; cerebral palsy; cerebral tumour; chemotherapy-induced organ damage; cisplatin-induced nephrotoxicity; coronary artery bypass surgery; Creutzfeldt-Jacob disease and its new variant associated with "mad cow" disease; diabetic neuropathy; Down's syndrome; drowning; epilepsy and post-traumatic epilepsy; Friedrich's ataxia; frontotemporal dementia; glaucoma; glomerulopathy; haemochromatosis; haemodialysis; haemolysis; haemolytic uraemic syndrome (Weil's disease); haemorrhagic stroke; Hallerboden-Spatz disease; heart attack and reperfusion injury; Huntington's disease; Lewy body disease; intermittent claudication; ischaemic stroke; inflammatory bowel disease; macular degeneration; malaria; methanol-induced toxicity; meningitis (aseptic and tuberculous); motor neuron disease; multiple sclerosis; multiple system atrophy; myocardial ischaemia; neoplasia; Parkinson's disease; peri-natal asphyxia; Pick's disease; progressive supra-nuclear palsy; radiotherapy-induced organ damage; restenosis after angioplasty; retinopathy; senile dementia; schizophrenia; sepsis; septic shock; spongiform encephalopathies; subharrachnoid haemorrage/cerebral vasospasm; subdural haematoma; surgical trauma, including neurosurgery; thalassemia; transient ischaemic attack (TIA); traumatic brain injury (TBI); traumatic spinal injury; transplantation; vascular dementia; viral meningitis; and viral encephalitis.

Additionally, the compound of the present invention may also be used to potentiate the effects of other treatments, for example to potentiate the neuroprotective effects of brain derived nerve growth factor.

The invention is particularly directed to conditions which induce oxidative damage of the central nervous system, including acute and chronic neurological disorders such as traumatic brain injury, spinal cord injury, cerebral ischaemia, stroke (ischaemic and haemorragic), subharrachnoid haemorrage/cerebral vasospasm, cerebral tumour, Alzheimer's disease, Creutzfeldt-Jacob disease and its new variant associated with "mad cow" disease, Huntington's disease, Parkinson's disease, Friedrich's ataxia, cataract, dementia with Lewy body formation, multiple system atrophy, Hallerboden-Spatz disease, diffuse Lewy body disease, amylotrophic lateral sclerosis, motor neuron disease, multiple sclerosis, fatal familial insomnia, Gertsmann Straussler Sheinker disease and hereditary cerebral haemorrhage with amyoidoisis-Dutch type.

More particularly, the invention is directed to the treatment of neurodegenerative amyloidosis. The neurodegenerative amyloidosis may be any condition in which neurological damage results from the deposition of amyloid. The amyloid may be formed from a variety of protein or polypeptide precursors, including but not limited to $A\beta$, synuclein, huntingtin, or prion protein.

Thus the condition is preferably selected from the group consisting of sporadic or familial Alzheimer's disease, amyotrophic lateral sclerosis, motor neuron disease, cataract, Parkinson's disease, Creutzfeldt-Jacob disease and its new variant associated with "mad cow" disease, Huntington's disease, dementia with Lewy body formation, multiple system atrophy, Hallerboden-Spatz disease, and diffuse Lewy body disease.

More preferably the neurodegenerative amyloidosis is an $A\beta$-related condition, such as Alzheimer's disease or dementia associated with Down syndrome or one of several forms of autosomal dominant forms of familial Alzheimer's disease (reviewed in St George-Hyslop, 2000). Most preferably the $A\beta$-related condition is Alzheimer's disease.

In a particularly preferred embodiment of all aspects of the invention, prior to treatment the subject has moderately or severely impaired cognitive function, as assessed by the Alzheimer's Disease Assessment Scale (ADAS)-cog test, for example an ADAS-cog value of 25 or greater.

In addition to slowing or arresting the cognitive decline of a subject, the compound and methods of the invention may also be suitable for use in the treatment or prevention of neurodegenerative conditions, or may be suitable for use in alleviating the symptoms of neurodegenerative conditions. The compound may be able to provide at least a partial reversal of the cognitive decline experienced by patients. If administered to a subject who has been identified as having an increased risk of a predisposition to neurodegenerative conditions, or to a subject exhibiting pre-clinical manifestations of cognitive decline, such as Mild Cognitive Impairment or minimal progressive cognitive impairment, these methods and compounds may be able to prevent or delay the onset of clinical symptoms, in addition to the effect of slowing or reducing the rate of cognitive decline.

Currently Alzheimer's disease and other dementias are usually not diagnosed until one or more warning symptoms have appeared. These symptoms constitute a syndrome known as Mild Cognitive Impairment (MC1), which was recently defined by the American Academy of Neurology, and refers to the clinical state of individuals who have memory impairment, but who are otherwise functioning well, and who do not meet clinical criteria for dementia (Petersen et al., 2001). Symptoms of MC1 include:

(1) Memory loss which affects job skills
(2) Difficulty performing familiar tasks
(3) Problems with language
(4) Disorientation as to time and place (getting lost)
(5) Poor or decreased judgement
(6) Problems with abstract thinking
(7) Misplacing things
(8) Changes in mood or behaviour
(9) Changes in personality
(10) Loss of initiative MCI can be detected using conventional cognitive screening tests, such as the Mini Mental Status Exam, and the Memory Impairment Screen, and neuropsychological screening batteries.

The term "subject" as used herein refers to any animal having a disease or condition which requires treatment with a pharmaceutically-active agent. The subject may be a mammal, preferably a human, or may be a domestic or companion animal. While it is particularly contemplated that the compound of the invention is suitable for use in medical treatment of humans, it is also applicable to veterinary treatment, including treatment of companion animals such as dogs and cats, and domestic animals such as horses, ponies, donkeys, mules, llama, alpaca, pigs, cattle and sheep, or zoo animals such as primates, fields, canids, bovids, and ungulates.

Suitable mammals include members of the Orders Primates, Rodentia, Lagomorpha, Cetacea, Carnivora, Perissodactyla and Artiodactyla. Members of the Orders Perissodactyla and Artiodactyla are particularly preferred because of their similar biology and economic importance.

For example, Artiodactyla comprises approximately 150 living species distributed through nine families: pigs (Suidae), peccaries (Tayassuidae), hippopotamuses (Hippopotamidae), camels (Camelidae), chevrotains (Tragulidae), giraffes and okapi (Giraffidae), deer (Cervidae), pronghorn (Antilocapridae), and cattle, sheep, goats and antelope (Bovidae). Many of these animals are used as feed animals in various countries. More importantly, many of the economically important animals such as goats, sheep, cattle and pigs have very similar biology and share high degrees of genomic homology.

The Order Perissodactyla comprises horses and donkeys, which are both economically important and closely related. Indeed, it is well known that horses and donkeys interbreed.

As used herein, the term "therapeutically effective amount" is meant an amount of a compound of the present invention effective to yield a desired therapeutic response, for example, to treat, ameliorate or prevent a neurological condition.

The specific "therapeutically effective amount" will, obviously, vary with such factors as the particular condition being treated, the physical condition of the subject, the type of subject being treated, the duration of the treatment, the nature of concurrent therapy (if any), and the specific formulations employed and the structure of the compound or its derivatives.

The compound of the present invention may additionally be combined with other medicaments to provide an operative combination. It is intended to include any chemically compatible combination of pharmaceutically-active agents, as long as the combination does not eliminate the activity of the compound of formula I or II. It will be appreciated that the compound of the invention and the other medicament may be administered separately, sequentially or simultaneously.

Other medicaments may include, for example, where the condition is a β-amyloid related condition, particularly Alzheimer's disease, an inhibitor of the acetylcholinesterase active site, for example phenserine, galantamine, or tacrine; an antioxidant, such as Vitamin E or Vitamin C; an anti-inflammatory agent such as flurbiprofen or ibuprofen optionally modified to release nitric oxide (for example NCX-2216, produced by NicOx) or an oestrogenic agent such as 17-β-oestradiol.

Methods and pharmaceutical carriers for preparation of pharmaceutical compositions are well known in the art, as set out in textbooks such as Remington's Pharmaceutical Sciences, 20th Edition, Williams & Wilkins, Pennsylvania, USA.

As used herein, a "pharmaceutical carrier" is a pharmaceutically acceptable solvent, suspending agent or vehicle for delivering the compound of formula I or II to the subject. The carrier may be liquid or solid and is selected with the planned manner of administration in mind. Each carrier must be pharmaceutically "acceptable" in the sense of being compatible with other ingredients of the composition and non injurious to the subject.

The compound of formula I may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection or infusion techniques. he present invention also provides suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc: Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The compound of formula I as well as the pharmaceutically-active agent useful in the method of the invention can be administered, for in vivo application, parenterally by injection or by gradual perfusion over time independently or together. Administration may be intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, anti-microbials, anti-oxidants, chelating agents, growth factors and inert gases and the like.

Generally, the terms "treating", "treatment" and the like are used herein to mean affecting a subject, tissue or cell to obtain a desired pharmacologic and/or physiologic effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes: (a) preventing the disease from occurring in a subject that may be predisposed to the disease, but has not yet been diagnosed as having it; (b) inhibiting the disease, i.e., arresting its development; or (c) relieving or ameliorating the effects of the disease, i.e., cause regression of the effects of the disease.

The invention includes various pharmaceutical compositions useful for ameliorating disease. The pharmaceutical compositions according to one embodiment of the invention are prepared by bringing the compound of formula I, analogues, derivatives or salts thereof, or combinations of the compound of formula I and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in *Remington's Pharmaceutical Sciences,* 20th ed. Williams and Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethyl cellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds of formula I may also be presented for use in the form of veterinary compositions, which may be prepared, for example, by methods that are conventional in the art. Examples of such veterinary compositions include those adapted for:

(a) oral administration, external application, for example drenches (e.g. aqueous or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin; or (d) intravaginally, e.g. as a pessary, cream or foam.

Dosage levels of the compound of formula I of the present invention are of the order of about 0.5 mg to about 20 mg per kilogram body weight, with a preferred dosage range between about 0.5 mg to about 10 mg per kilogram body weight per day (from about 0.5 gms to about 3 gms per patient per day). The amount of active ingredient that may be combined with the carrier materials to produce a single dosage will vary depending upon the host treated and the particular mode of administration. For example, a formulation intended for oral administration to humans may contain about 5 mg to 1 g of an active compound with an appropriate and convenient amount of carrier material which may vary from about 5 to 95 percent of the total composition. Dosage unit forms will generally contain between from about 5 mg to 500 mg of active ingredient.

Optionally the compounds of the invention are administered in a divided dose schedule, such that there are at least two administrations in total in the schedule. Administrations are given preferably at least every two hours for up to four hours or longer; for example the compound may be administered every hour or every half hour. In one preferred embodiment, the divided-dose regimen comprises a second administration of the compound of the invention after an interval from the first administration sufficiently long that the level of active compound in the blood has decreased to approximately from 5-30% of the maximum plasma level reached after the first administration, so as to maintain an effective content of active agent in the blood. Optionally one or more subsequent administrations may be given at a corresponding interval from each preceding administration, preferably when the plasma level has decreased to approximately from 10-50% of the immediately-preceding maximum.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

EXAMPLES

The invention will now be described in detail by way of reference only to the following non-limiting examples.

For clarity, compounds of this invention are referred to by number, for example 1-4 and 2-3. The structures of the example compounds so referred to are given in Tables 1-10.

In Examples 1 to 6, the following references are cited:

1. Dondoni, A. et al, *Synthesis,* 1996, 641 and 1987, 998.

2. Goldstein, H. and Schaaf, E., *Helv. Chim. Acta,* 1957, 57(23), 132.

3. March, J. in "*Advanced Organic Chemistry, reactions, mechanisms and structure*", 3$^{rd}$ edition, John Wiley & Sons, 1985, pg. 601, and references cited therein; for more specific reaction conditions, see for example: Giencke, A. and Lackner, H. *Liebigs Ann. Chem.,* 1990, 569; Brown, L. L. et al, *J. Med. Chem.,* 2002, 45, 2841; Koch, V. and Schnatterer, S. *Synthesis,* 1990, 499;

4. Linderberg, M. et al, *Eur. J. Med. Chem.,* 1999, 34, 729.

5. T. W. Greene and P. G. M. Wuts (Eds) in "Protective Groups in Organic Synthesis", John Wiley & Sons, U.S.A. (1999).

6. Follope, M. P. et al, *Eur. J. Med. Chem.,* 1992, 27, 291; Giencke, A. et al, *Liebigs Ann. Chem.,* 1990, 569.

7. Bavetsias, V. et al, *J. Med. Chem.,* 2002, 45, 3692.

General Experimental Details 2,4-Dichlorobenzoic acid (1-1) and 2,4-dichloro-6-nitrophenol (2-1B) were purchased from Aldrich. All reagents/reactants, unless otherwise stated, were sourced from Aldrich. 4-Amino-1,3,5-trimethylpyrazole, 2-amino-4,6-dihydroxypyrimidine, 4-chloromethyl-3,5-dimethylisoxazole and 2-chloromethyl-4-methylthiazole hydrochloride were purchased from Lancaster. (2-Aminomethyl)thiazole was prepared according to the literature.[1] Solvents were analytical grade and used as supplied. THF was distilled from sodium and benzophenone under argon. $^1$H NMR spectra (δ, relative to TMS) were recorded on a Varian Inova 400 spectrometer unless otherwise indicated; J-Values are given in Hertz. Mass spectral data were recorded on a Micromass Quattro II mass spectrometer.

A practical and concise synthesis of 4,6-dichloro-3-hydroxy-2-nitrobenzoic acid (1-6), a key intermediate used for the preparation of a range of 8-hydroxy-3H-quinazolin-4-ones and, specifically, for the synthesis of 5,7-dichloro-substituted derivatives, is shown in Scheme 1A. Hence, according to Goldstein and Schaaf,[2]

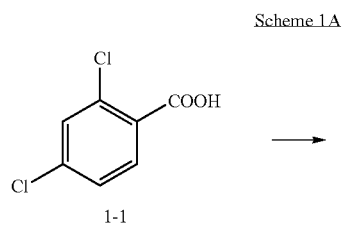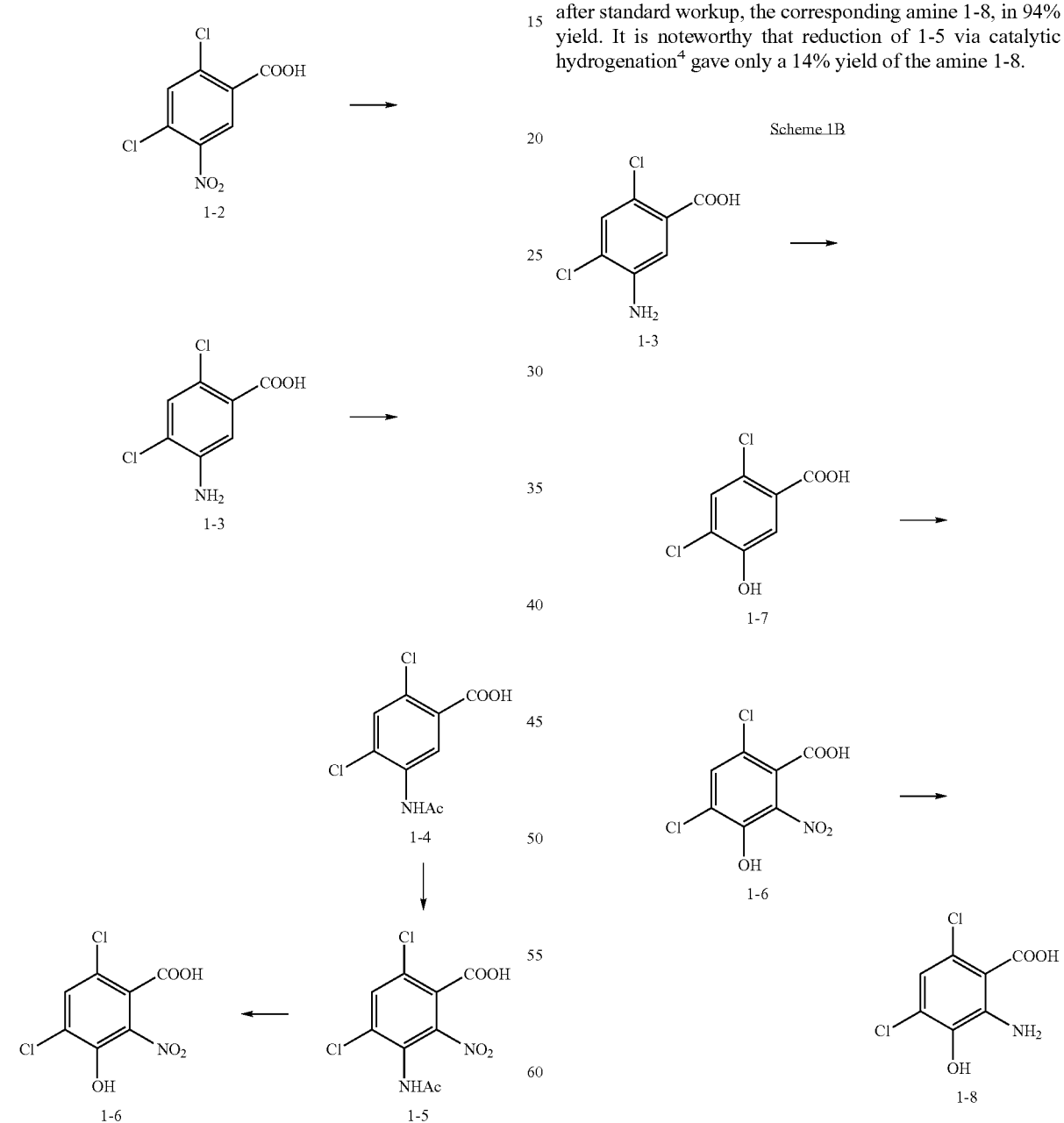

1-4, into 3-acetamido-4,6-dichloro-2-nitrobenzoic acid (1-5). Subsequent base hydrolysis of 1-5 gives, following workup with acid, the 2-nitrobenzoic acid 1-6. All steps proceed in high yields (about 90%) and are amendable to scale-up. Compound 1-6 can also be produced according to the route shown in Scheme 1B. Thus, diazotisation of 1-3 via standard or routine conditions[3] gives the alcohol 1-7. Compound 1-7 is then nitrated according to the conditions previously described in the literature[4] to provide 1-6. The synthetic routes shown in both Schemes 1A and 1B for the preparation of 1-6 represent improvements on the literature[4] method, with all steps shown proceeding in good yields. Reduction of 1-6 with iron powder in HOAc at 80° C. for 45-50 minutes gives, after standard workup, the corresponding amine 1-8, in 94% yield. It is noteworthy that reduction of 1-5 via catalytic hydrogenation[4] gave only a 14% yield of the amine 1-8.

commercially available 2,4-dichlorobenzoic acid (1-1) is nitrated to give 2,4-dichloro-5-nitrobenzoic acid (1-2). Compound 1-2 is converted, via the amine 1-3 and the acetamide A range of novel 8-hydroxy-3N-substituted quinazolin-4-ones of this invention can be synthesised according to the routes shown schematically in Scheme 2A.

Scheme 2A
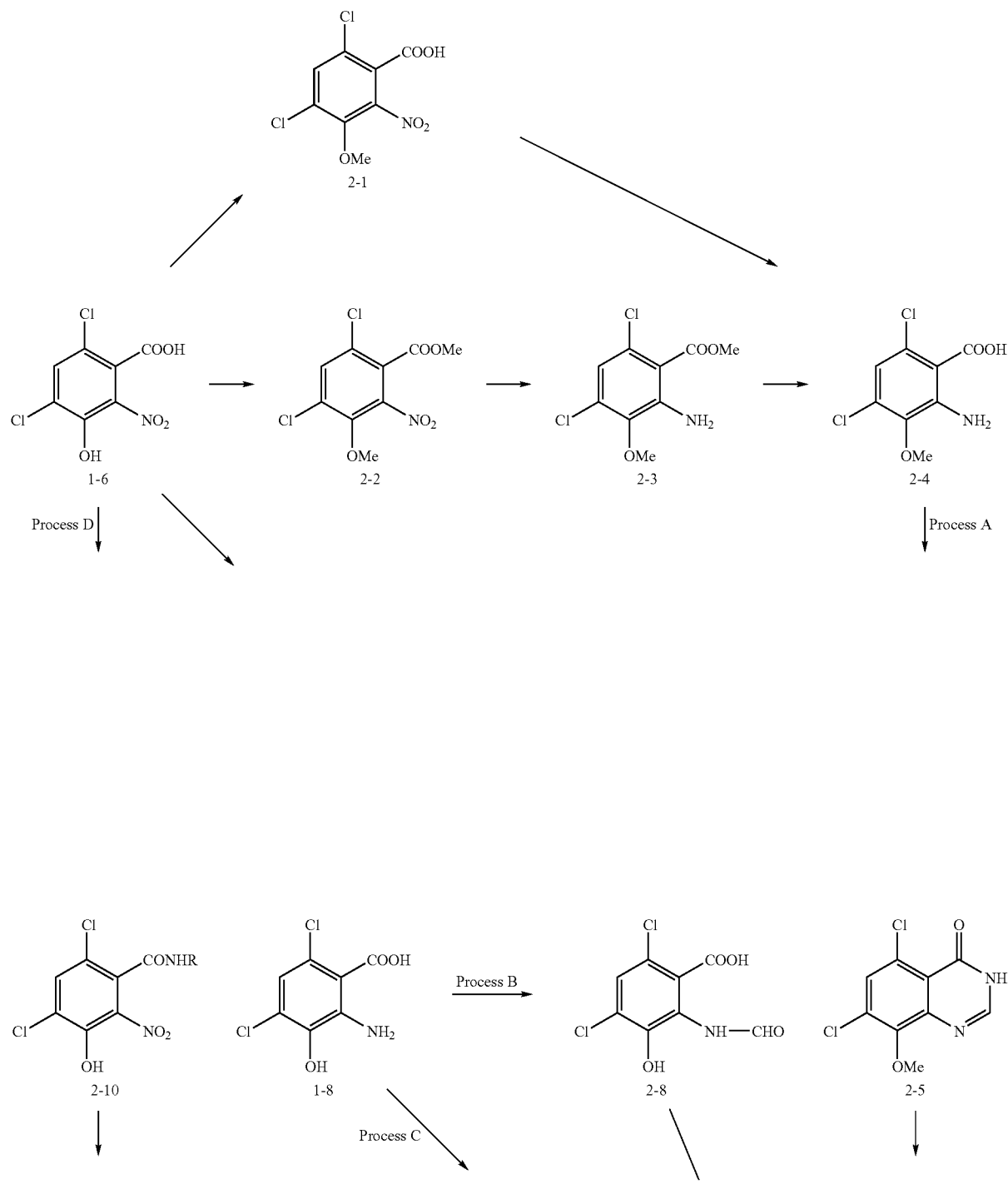

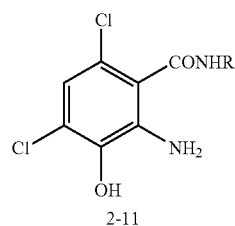

2-11

-continued

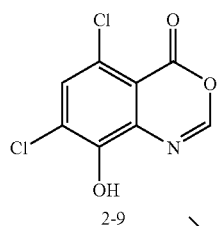

2-9

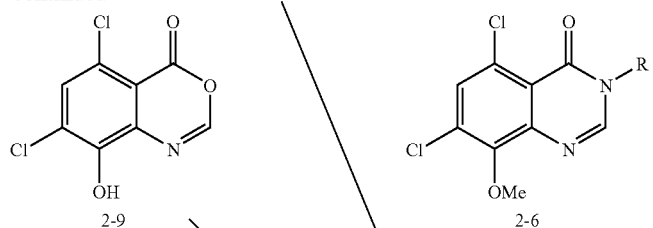

2-6

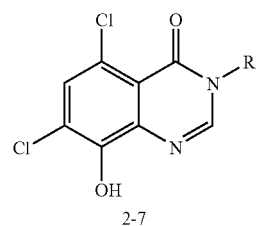

2-7

In process A (Scheme 2A), the 2-nitrobenzoic acid 1-6 can be first converted, via either 2-1 or 2-2 and 2-3, into the anthranilic acid 2-4.

An alternate synthesis of 2-4 using standard procedures is shown in Scheme 2B. Thus, treatment of 2,4-dichloro-6-nitrobenzoic acid (2-1B) with dimethyl sulphate according to conditions previously described for the preparation of 2-2 from 1-6, gives 2-2B. Reduction of the nitro compound 2-2B under standard conditions, typically using tin(II) chloride or iron powder and glacial acetic acid/hydrochloric acid, gives the anisidine 2-3B. Treatment of the anisidine 2-3B with chloral hydrate in the presence of hydroxylamine hydrochloride followed by acid hydrolysis gives the isatin intermediate 2-4B. Subsequent treatment of 2-4B with hydrogen peroxide under basic conditions gives the anthranilic acid 2-4.

Scheme 2B

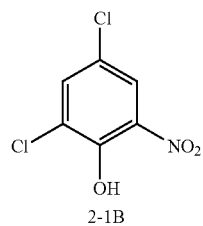 

2-1B

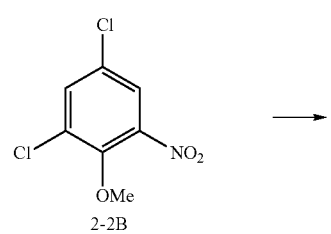 

2-2B

-continued

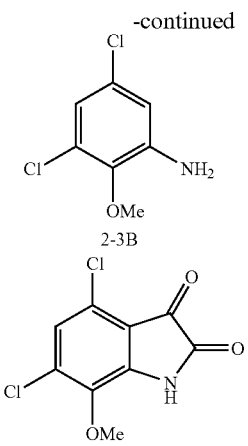 

2-3B

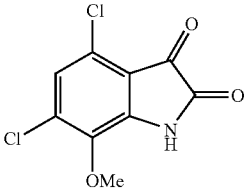 

2-4B

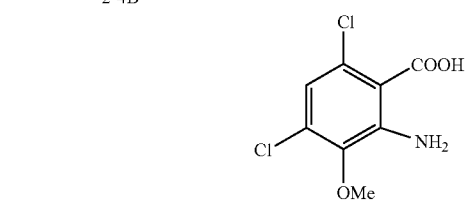

2-4

Treatment of 2-4 with formamide at an elevated temperature, typically at 150° C., provides the 3H-quinazolin-4-one 2-5. Compound 2-5 is then reacted with the appropriate alkyl halide in the presence of a base, for example potassium carbonate, to give 2-6. Examples of alkyl halides that can be employed in process C include, but are not limited to, 2-(chloromethyl)pyridine, (chloromethyl)cyclopropane, 1-(2-chloroethyl)pyrrolidine, 2-(2-chloroethyl)-1-methylpyrrolidine, 4-(2-chloroethyl)morpholine, 2-chloromethyl-4-methylthiazole hydrochloride, 2,6-bis(chloromethyl)pyridine, 2-bromopropane, 1-chloropropane, 1-chloro-2-methylpropane, 2-chloroethyl ethyl ether, (2-diethylamino)ethyl chloride hydrochloride, 1-chlorobutane, 2-chlorobutane, crotyl chloride and 4-chloromethyl-3,5-dimethylisoxazole. Results are tabulated (Table 1). Subsequent removal of the protecting group from 2-6, suitably using BBr$_3$ or with aqueous HBr at an elevated temperature, provides the corresponding 3-N-(substituted)-8-hydroxy-3H-quinazolin-4-one 2-7. In the case of the ethyl ether derivative 2-6M, the hydrobromide salt of the alcohol 2-7M1 was obtained (Table 2). Treatment of the alkene 2-6P with aqueous HBr resulted in hydrobromination of the alkenic double bond with concomitant removal of the methoxy protecting group giving compound 2-7P1.

In processes B and C (Scheme 2A), the anthranilic acid 1-8 can be treated with acetic formic anhydride to give the formylamino compound 2-8 or the benzo[d][1,3]oxazin-4-one 2-9. Compound 2-8 (or 2-9) is then reacted with a suitable amine in the presence of a condensing agent such as phosphorus trichloride or triethyl orthoformate at an elevated temperature, typically using toluene or xylene at near reflux temperature, to yield the 8-hydroxy-3H-quinazolin-4-ones 2-7. Examples of amines that can be employed in processes B and C include, but are not limited to, 2-amino-5-methylthiazole, 2-(2-aminoethyl)pyridine, 3-aminopyridine, 4-aminomorpholine, 1-amino-4-methylpiperazine, 1-aminopyrrolidine, 4-(aminomethyl)piperidine, 1-aminopiperazine, 5-amino-1-ethylpyrazole, 5-amino-2-methoxypyridine, 4-amino-1,3,5-trimethylpyrazole, 2-amino-1-methylbenzamide, 2-amino-5-methylpyridine, 2-amino-5-chloropyridine and 4-aminopiperidine. Results are tabulated (Table 3). Other 8-hydroxy-3H-quinazolin-4-ones that can be prepared according to these processes are shown in Table 4.

In process D (Scheme 2A), the 2-nitrobenzoic acid 1-6 can first be treated with a suitable amine in the presence of an activating agent such as CDI to produce the appropriate N-(substituted)benzamide 2-10. Subsequent reduction of the nitro group and coupling of the resultant amine 2-11, typically with formic acid in the presence of a condensing agent such as CDI or triethyl orthoformate or with formamide provides the corresponding 3-N-substituted derivative 2-7.

Processes B and C (Scheme 2A) can be repeated utilizing a suitably O-protected anthranilic acid such as 2-4 (Scheme 3). In these cases, the 8-hydroxy-3H-quinazolin-4-ones 2-7 are obtained following removal of the O-protecting group.

Scheme 3

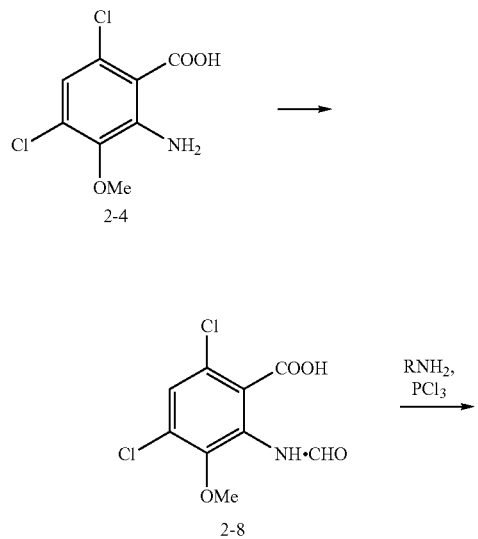

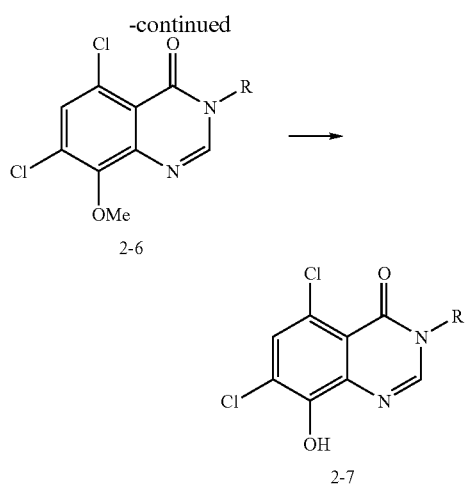

2-Substituted 8-hydroxy-3H-quinazolin-4-ones can be prepared according to the routes depicted in Scheme 4. Hence, according to process E, treatment of the anthranilic acid 1-6 with an activating agent such as thionyl chloride and subsequent reaction of the intermediate acid chloride with ammonia gives the corresponding benzamide 4-1. Reduction of the nitro compound 4-1, typically with either SnCl$_2$ or iron powder/HOAc, gives the corresponding amine 4-2. The amine 4-2, in turn, can be treated with either chloroacetyl acetic acid or 2-chloro-1,1,1-trimethoxyethane to provide 5,7-dichloro-2-chloromethyl-8-hydroxy-3H-quinazolin-4-one (4-3A). The 2-chloromethyl compound can also be prepared from the methoxy anthranilic acid derivative 2-4 via process F. Thus, treatment 7 of 2-4 with chloroacetonitrile in the presence of base, typically sodium methoxide, gives 4-3B. Further elaboration of the 2-chloromethyl derivative 4-3A (or 4-3B) with a range of amines such as, but not limited to, dimethylamine, methylamine and ethylamine, provides a number of novel 2-substituted derivatives 4-16A -4-16D.

A number of 2,3-disubstituted 8-hydroxy-3H-quinazolin-4-ones 4-9 can be prepared via the acid 2-1 according to process G, as shown in Scheme 4. Hence, 2-1 can be treated with a suitable amine in the presence of an activating agent to afford the corresponding benzamide 4-5 which is then reduced, typically using SnCl$_2$ or iron powder/HOAc, into 4-6. Compound 4-6 is subsequently transformed into the 2-chloromethyl derivative 4-7 and this, in turn, into 4-8 employing reaction conditions similar to those previously described in processes E and F. Following deprotection, typically employing aqueous HBr at near refluxing temperature, 4-8 provides the corresponding 2,3-disubstituted derivatives 4-9.

2,3-Disubstituted 8-hydroxy-3H-quinazolin-4-ones 4-9 can also be accessed via processes H and I (Scheme 4). In process H, the anthranilic acid 1-8 is suitably acylated with a NP-containing acylating agent such as 2-azidoacetyl chloride, phthalyl-glycyl chloride and [(phenylmethyl)amino]acetyl chloride. Accordingly, examples of NP groups are azido, phthalimido and benzylamino. Subsequent condensation of the intermediate 4-10 the presence of acetic anhydride at an elevated temperature, typically at near reflux temperature, furnishes the benzo[d][1,3]oxazin-4-one 4-11. In the presence of an appropriate amine (R$_1$NH$_2$), 4-11 gives 4-12; 4-12, in turn, gives 4-13 via a condensation. Suitable condensing agents include PCl$_3$, triethyl orthoformate, CDI and Ac$_2$O. Conditions for the transformation of the —NP moiety into the amino group will depend on the particular NP group; for the abovementioned groups, these are respectively reduction, dimethylamine and catalytic hydrogenolysis (more examples of conditions[5] for the latter two transformations can be found elsewhere). In process I, condensation of the anthranilic acid 1-8 with a suitable amine (NR$_1$R$_2$) affords the amide 4-14. Subsequent successive treatment of 4-14 with chloroacetyl chloride and an amine gives 4-9.

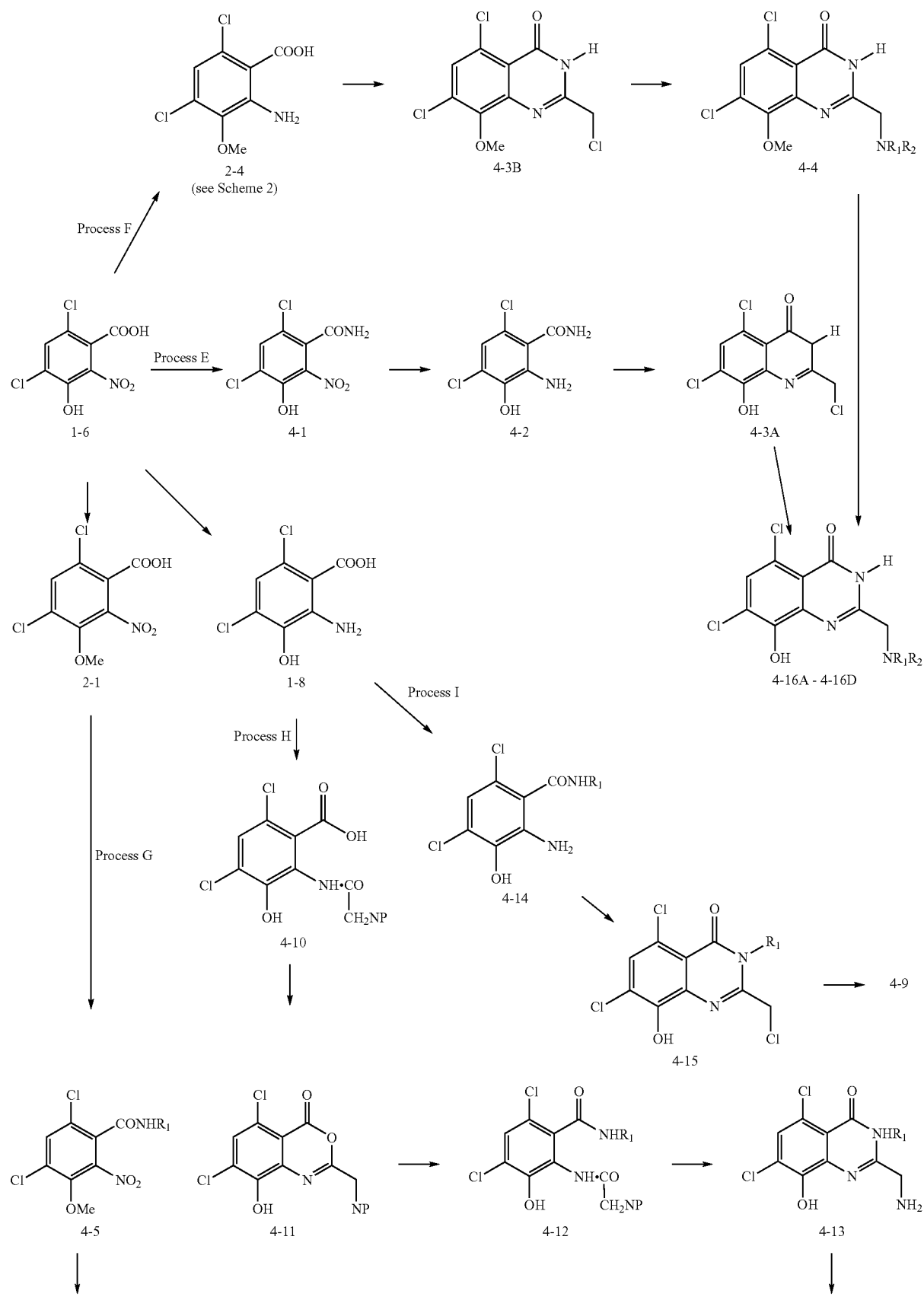
Scheme 4

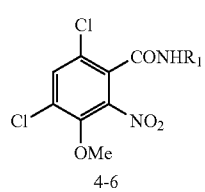 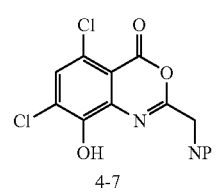 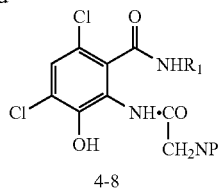 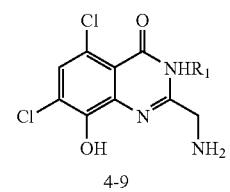

| 4-6 | 4-7 | 4-8 | 4-9 |

3-Amino-5,7-dichloro-8-hydroxy-3H-quinazolin-4-one (5-4) and certain 3-(substituted)amino-3H-quinazolin-4-ones can be prepared according to routes shown in Scheme 5. N-Formylation of the methyl ester 2-3, typically using acetic formic anhydride, provides 5-1. Alternatively, treatment of 2-3 with an orthoester such as triethyl orthoformate provides the imidate ester 5-2. Upon treatment with hydrazine, 5-1 or 5-2 yields the 3-amino-3H-quinazolin-4-one 5-3. Removal of the protecting group in 5-3, typically with aqueous HBr at 120° C., gives 5-4. Further elaboration of the 3-amino compound 5-4 using suitable acid halides provides the corresponding 3-substituted acylated derivatives, 5-5A-5-5C. Derivatives such as 5-7A-5-7C can be obtained from 5-2 via substitution of hydrazine hydrate for the appropriately substituted hydrazine such as 4-fluorophenylhydrazine, 4-methoxyphenylhydrazine or 2,4-difluorophenylhydrazine, followed by deprotection. With alkyl halides in a suitable solvent, typically ethanol, followed by deprotection, 5-3 provides compounds 5-7D-5-7G. Alternatively, compounds 5-7D-5-7G can also be prepared via treatment of 5-2 with the appropriate alkylated hydrazine such as ethylhydrazine, propylhydrazine and (cyclopropyl)methylhydrazine.

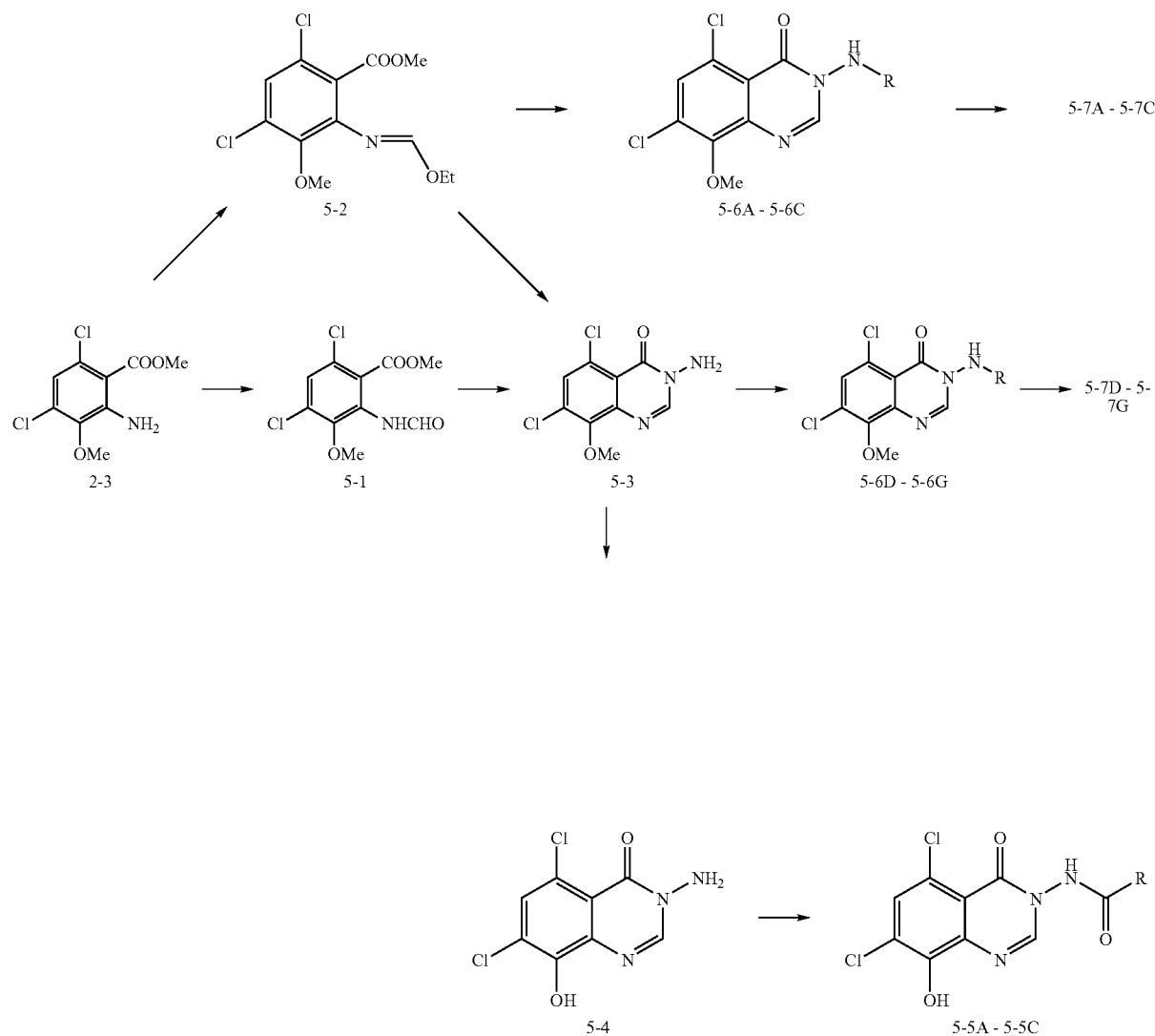

Scheme 5

The amines 2-7F2, 2-7Q2, 2-7R2, 2-7S2 and 2-7X2 can be elaborated into a range of derivatives such as 6-1-6-6 via treatment with alkyl halides or acylating reagents. Data for 6-1-6-6 are tabulated (Table 9).

A number of 3-substituted-3H-quinazolin-4-thiones 7-2 can be prepared from the corresponding 3H-quinazolin-4-ones 2-6 according to the process shown in Scheme 6. Thus, treatment of 2-6 with either $P_4S_{10}$ or Lawesson's Reagent provides the thioketone 7-1. Subsequent removal of the protecting group, suitably using $BBr_3$, gives the desired 3-substituted-3H-quinazolin-4-thione 7-2.

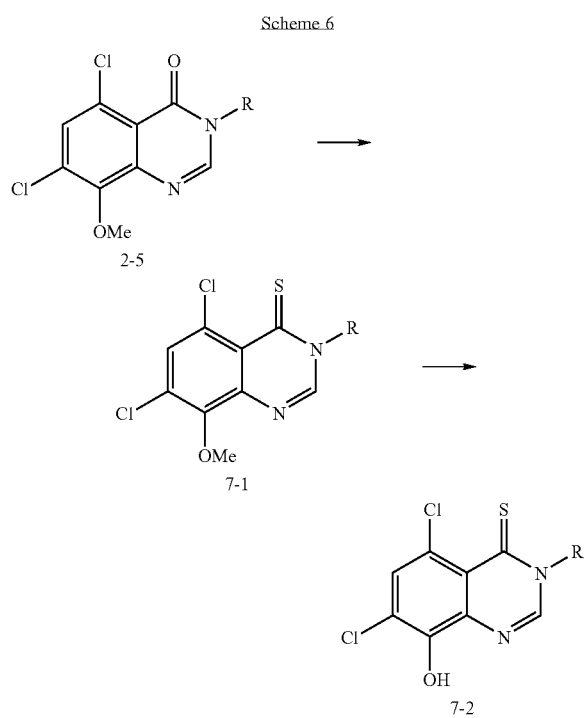

Scheme 6

Preparation of 4,6-Dichloro-3-hydroxy-2-nitrobenzoic acid (1-6)

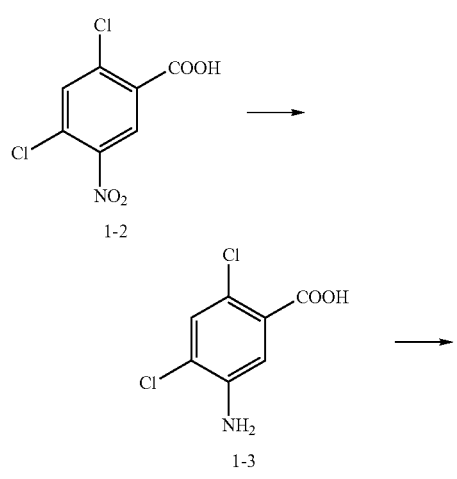

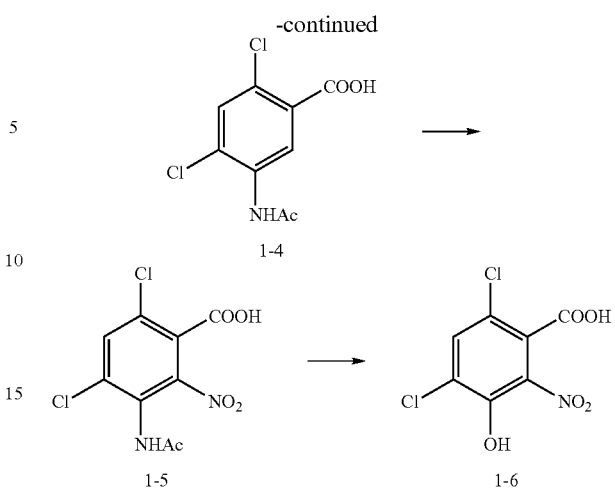

Tin(II) chloride hydrate (50 g, 0.29 mol) was added to a solution of 2,4-dichloro-5-nitrobenzoic acid (1-2)[2] (10.0 g, 0.045 mol) in EtOH (200 mL). The mixture was stirred at 70° C. for 0.5 h, cooled and poured onto ice. The pH of the mixture was adjusted to 8 (sat'd $NaHCO_3$). The suspension was left to stir at room temperature for 5 h and re-acidified to pH 5 (glacial HOAc). The resulting white suspension was continuously extracted with ethyl acetate, the extracts combined, washed with brine, dried and concentrated to yield the desired amine (1-3) as an off-white solid (8.8 g, 96%).

5-Amino-2,4-dichlorobenzoic acid (1-3): $^1$H NMR ($CD_3OD$): δ 7.30 (s, 1H), 7.27 (s, 1H).

Acetic anhydride (27 mL) was added to 5-amino-2,4-dichlorobenzoic acid (1-3) (8.0 g, 0.041 mol) in glacial HOAc (150 mL). The solution was stirred at room temperature for 0.5 h and concentrated to yield the desired acetamide (1-4) as a white solid (9.6 g, 96%).

5-Acetamido-2,4-dichlorobenzoic acid (1-4): $^1$H NMR ($CD_3OD$): δ 8.32 (s, 1H), 7.62 (s, 1H), 2.19 (s, 3H).

5-Acetamido-2,4-dichlorobenzoic acid (1-4) (9.6 g, 0.039 mol) was added in small portions over 30 min to a stirred ice-cooled solution of fuming nitric acid (1.8 mL, 0.043 mol) and conc sulfuric acid (120 mL). After the addition was complete, more fuming nitric acid (17 mL) and conc sulfuric acid (80 mL) were added at 30 min and 60 min intervals. The reaction mixture was then left to stir for an additional 2.5 h at 0° C., allowed to warm to 12-16° C. and left to stir at this temperature until all starting material was consumed (about 3 h). The solution was poured onto ice and extracted with ethyl acetate (3×). The organic extracts were combined, washed with brine, dried, and concentrated to give 3-acetamido-4,6-dichloro-2-nitrobenzoic acid (1-5) as an orange solid (9.8 g, 86%).

3-Acetamido-4,6-dichloro-2-nitrobenzoic acid (1-5): $^1$H NMR ($CD_3OD$): δ 8.01 (s, 1H), 2.13 (s, 3H).

3-Acetamido-4,6-dichloro-2-nitrobenzoic acid (1-5) (9.7 g, 0.033 mol) was added to a solution of KOH (18.7 g, 0.034 mol) in $H_2O$ (85 mL). The solution was heated under reflux for 18 h and cool to room temperature. Conc HCl was added to adjust the pH to 0. The mixture was diluted with ethyl acetate and $H_2O$ and left to stir at room temperature for 30 min. The layers were separated; the aqueous layer was extracted with ethyl acetate (3×), the extracts combined with the original organic layer, washed with brine, dried and concentrated to yield 4,6-dichloro-3-hydroxy-2-nitrobenzoic acid (1-6) as a dark red solid (7.4 g, 89%); m.p. 188-189° C. (lit.[4] m.p. 186° C. (dec)).

4,6-Dichloro-3-hydroxy-2-nitrobenzoic acid (1-6): $^1$H NMR (CD$_3$OD): δ 7.79 (s, 1H); mass spectrum: m/z 250, 252, 254 (M$^+$−1, 100%, 66%, 11%).

Preparation of 5,7-dichloro-8-methoxy-3H-quinazolin-4-one (2-5)

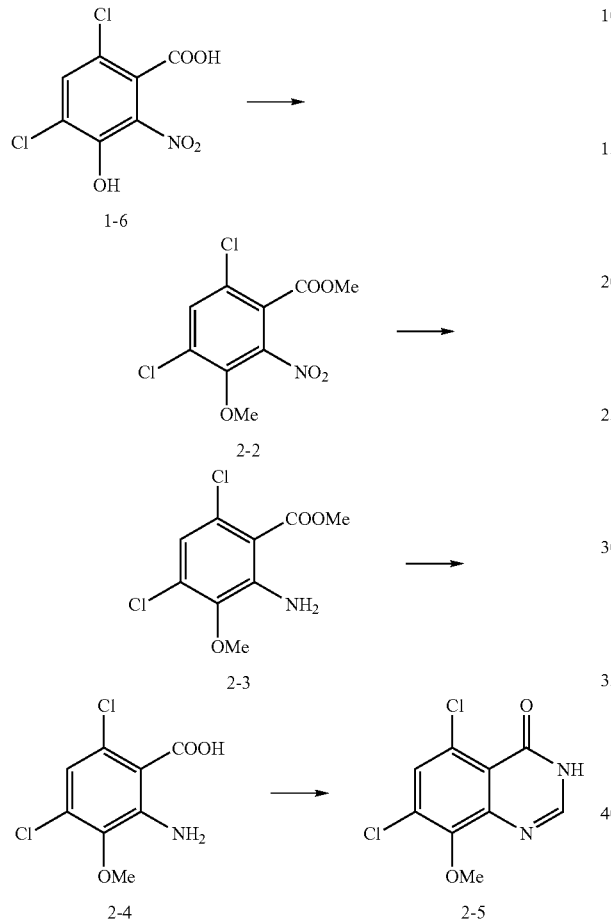

Dimethyl sulfate (40 mL) was added to a stirring mixture of 1-6 (15.0 g, 0.059 mol), potassium carbonate (66 g, 0.5 mol) and DMF (300 mL). The resulting mixture was left to stir at 60° C. overnight and then at 120° C. for 2 hours. The reaction mixture was concentrated in vacuo. The resulting reddish brown residue was washed water and dried. This gave 2-2 as a a orange solid (14.6 g, 88%). —$^1$H NMR (CDCl$_3$): δ 7.65 (s, 1H), 4.01 (s, 3H), 3.92 (s, 3H).

Iron powder (18.2 g, 0.33 mol) was added to a solution of 2-2 (13.3 g, 0.048 mol) in acetic acid (120 mL). The mixture was stirred at 55° C. for 1.5 hours and then filtered whilst hot through celite (ethyl acetate). The filtrate was concentrated, ethyl acetate and saturated sodium carbonate was added, and the mixture filtered (celite). The organic layer was isolated, washed with water, dried (K$_2$CO$_3$), and concentrated to give 2-3 as an off-white solid (11.6 g, 97%). —$^1$H NMR (CDCl$_3$): δ 6.71 (s, 1H), 3.89 (s, 3H), 3.79 (s, 3H).

To a stirred solution of 2-3 (11.5 g, 0.046 mol) in methanol (250 mL) and water (70 mL) was added 2M NaOH (25 mL). The reaction mixture was heated under reflux for 1 hour, more 2M NaOH was added (25 mL) and the mixture was heated under reflux for a further 1 hour. The solution was cooled and concentrated to remove the methanol. The concentrate was dissolved in water, extracted with ethyl acetate, and the pH adjusted to 1-2 (conc HCl). The milky suspension was extracted with ethyl acetate (3×). The combined extracts were washed with brine, dried and concentrated to give 2-4 as a beige solid (10.4 g, 95%). —$^1$H NMR (CD$_3$OD): δ 6.70 (s, 1H), 3.80 (s, 3H).

A stirred suspension of 2-4 (16.9 g, 0.072 mol) and formamide (150 mL) was heated at 150° C. for 8 hours and then allowed to cool to room temperature. Water was added, the resulting precipitate isolated via filtration, washed with water and dried under vacuum to give 2-5 as a light brown solid (13.0 g, 73%). —$^1$H NMR (CD$_3$OD): δ 8.08 (s, 1H), 7.60 (s, 1H), 3.98 (s, 3H).

Example 1

Preparation of Compounds 2-7A2-2-7R2 via alkylation of 5,7-dichloro-8-methoxy-3H-quinazolin-4-one (2-5) and subsequent deprotection

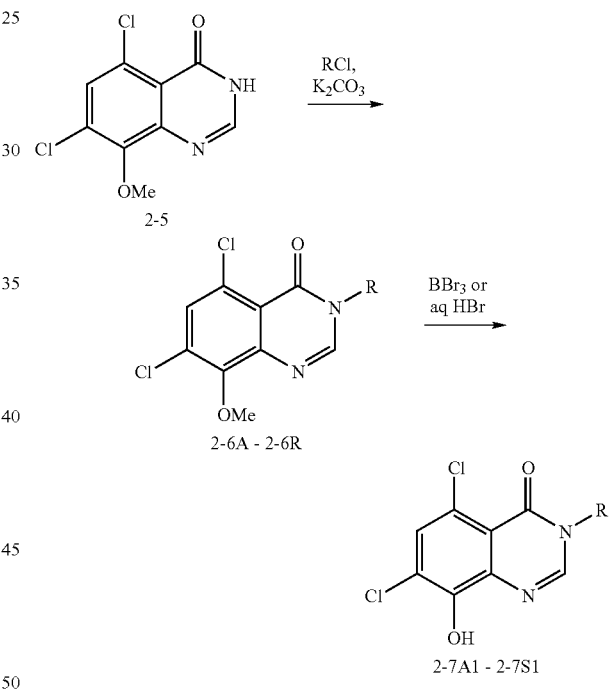

To a stirred solution of 2-5 (1.5 g, 6.1 mmol) and the chloride (7.3 mmol) in anhydrous DMF (30 mL) was added K$_2$CO$_3$ (9.3 mmol) and the resulting mixture heated at 95° C. for 16 hours, cooled, and concentrated. The residue was extracted with ethyl acetate or dichloromethane (3×), the extracts combined and washed successively with water and brine, and dried. Subsequent purification either by trituration with an appropriate solvent, recrystallisation or SiO$_2$-gel chromatography, gave the corresponding 3-substituted-8-methoxy-3H-quinazolin-4-one (2-6).

Examples of chlorides used: 1-(2-chloroethyl)pyrrolidine gives 2-6A, 2 (chloromethyl)cyclopropane gives 2-6B, 2-(2-chloroethyl)-1-methylpyrrolidine gives 2-6C, 2-(chloromethyl)pyridine gives 2-6D, 4-(2-chloroethyl)morpholine gives 2-6E, 2-chloromethyl-4-methylthiazole hydrochloride gives 2-6F, 4-chloromethyl-3,5-dimethylisoxazole gives 2-6G, 2-bromopropane gives 2-6H, 1-chloropropane gives 2-6I, 1-chloro-2-methylpropane gives 2-6J, 1-chlorobutane gives 2-6K, 2-chlorobutane gives 2-6L, 2-chloroethyl ethyl ether gives 2-6M, (2-diethylamino)ethyl chloride hydrochloride gives 2-6N, 2-chloromethyl-3-methylpyridine hydrochloride gives 2-6O, crotyl chloride gives 2-6P, 2,6-bis(chloromethyl)pyridine gives 2-6Q and 1-chloroethane gives 2-6R. In the cases of 1-(2-chloroethyl)pyrrolidine hydrochloride, 2-chloromethyl-3-methylpyridine hydrochloride and 2-chloromethyl-4-methylthiazole hydrochloride, 2.2 equivalents of $K_2CO_3$ were employed.

Preparation of (2-chloromethyl)-3-methylpyridine hydrochloride

To a stirred solution of 2,3-lutidine (5.00 g, 46.7 mmol) in chloroform (100 mL) at 0° C. was added m-chloroperbenzoic acid (12.0 g of a 77% max reagent) portionwise over 5 min. The reaction mixture was stirred for an additional 30 min at 0° C. and then allowed to warm to room temperature. After 16 h, the reaction mixture was concentrated to dryness, water (20 mL) was added and the pH of the mixture was adjusted to 8 (saturated $NaHCO_3$). The mixture was concentrated and the residue was extracted with dichloromethane/methanol (4:1). The extracts were concentrated to a white solid. Subsequent column purification ($SiO_2$; dichloromethane/methanol, 9:1) gave 2,3-lutidine-N-oxide as a white solid (4.80 g, 83%).

A stirred solution of 2,3-lutidine-N-oxide (4.80 g, 39.0 mmol) in acetic anhydride (50 mL) was heated under reflux overnight, cooled and then concentrated to dryness providing (2-acetoxymethyl)-3-methylpyridine as a brown oil (6.34 g). A mixture of the crude (2-acetoxymethyl)-3-methylpyridine and $K_2CO_3$ (10.0 g, 72.4 mmol), methanol (60 mL) and water (30 mL) was stirred at room temperature overnight. The solid was filtered off and the filtrate was concentrated to dryness. The residue, after column chromatography ($SiO_2$; dichloromethane/methanol, 9:1), gave (2-hydroxymethyl)-3-methylpyridine as a light brown oil (2.86 g, 59% over 2 steps).

(2-Hydroxymethyl)-3-methylpyridine: $^1H$ NMR ($CDCl_3$): δ 8.41 (d, J=4.9, 1H), 7.48 (d, J=7.5, 1H), 7.16 (dd, J=4.9 and 7.5, 1H), 4.69 (s, 2H), 4.00 (br, 1H), 2.22 (s, 3H).

To an ice-cooled solution of (2-hydroxymethyl)-3-methylpyridine (1.00 g, 8.1 mmol) in dichloromethane (30 mL) was added a solution of thionyl chloride (2.5 mL) in dichloromethane (6 mL) dropwise over 10 min. The ice bath was removed, the reaction mixture was left to stir at room temperature for 2 h, concentrated, and then washed with diethyl ether. This provided (2-chloromethyl)-3-methylpyridine hydrochloride as a pale straw-coloured solid (1.44 g, 99%).

(2-Chloromethyl)-3-methylpyridine hydrochloride: $^1H$ NMR ($CD_3OD$): δ 8.72 (d, J=5.9, 1H), 8.54 (d, J=8.1, 1H), 8.00 (dd, J=5.9 and 8.1, 1H), 5.05 (s, 2H), 2.64 (s, 3H).

Yields and spectral data for the compounds 2-6A-2-6R prepared are given in Table 1.

Deprotection

Method A: To a stirred ice-cooled solution of the 8-methoxy derivative 2-6 (1.9 g, 5.6 mmol) in dichloromethane (15 mL) was added $BBr_3$ (12 mL of a 1M solution in dichloromethane, 12 mmol). The solution was then stirred at 45° C. for 18 hours, cooled, and methanol (20 mL) was added. The mixture was concentrated. Excess borate was removed by repeatedly adding methanol and evaporation. The crude hydrobromide salt of the product was washed with ether (3×). Some compounds were isolated as the free base: thus, saturated $Na_2CO_3$ (20 mL) was added and the mixture extracted with dichloromethane (5×). The combined extracts were washed with water, dried, and concentrated. The residue was purified either by simply washing with an appropriate solvent, recrystallisation, or $SiO_2$-column chromatography to give the corresponding 8-hydroxy derivative 2-7.

Method B: A solution of 3-substituted-8-methoxy-3H-quinazolin-4-one (2-6) (5.0 mmol) in 48% hydrobromic acid (25 mL) was heated under reflux in an argon atmosphere for 16-18 hours, and left to cool to room temperature. The reaction mixture was either concentrated to dryness or the precipitate which formed was isolated via filtration. The crude solid was then successively washed with diethyl ether, dichloromethane and acetonitrile, affording the corresponding 8-hydroxy compound (2-7) as the hydrobromide salt. Some compounds were isolated as the free base (see Method A above for conditions).

Method C: A solution of the 8-methoxy compound 2-6 (4.46 mmol) and 48% hydrobromic acid (23 mL) was heated at 120° C. for 2-10 hours and left to cool to room temperature. Water (30 mL) was added and the pH was adjusted to 5 (NaOH pellets). The resulting precipitate was isolated via filtration, washed with water and dried in vacuo.

In the case of the ethyl ether derivative 2-6M, the hydrobromide salt of the alcohol 2-7M1 was obtained (Table 2). Treatment of the alkene 2-6P with $BBr_3$ according to Method A gave 2-7S1. The bromide 2-7P1 was obtained via treatment of 2-6P with aqueous HBr according to Method B.

Yields and spectral data for 2-7A1-2-7S1 are given in Table 2.

TABLE 1

Compounds 2-6A-2-6R prepared according to Example 1

| Compound | Structure | Yield (%) | $^1H$ NMR data | Mass spectral data |
|---|---|---|---|---|
| 2-6A | 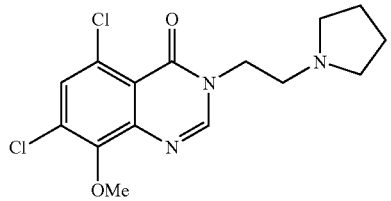 | 94 | ($CDCl_3$): δ 8.12 (s, 1 H), 7.51 (s, 1 H), 4.06 (t, J = 5.5, 1 H), 4.04 (s, 3 H), 2.84 (t, J = 5.5, 1 H), 2.56 (m, 4 H), 1.77 (m, 4 H) | |

TABLE 1-continued

Compounds 2-6A-2-6R prepared according to Example 1

| Compound | Structure | Yield (%) | ¹H NMR data | Mass spectral data |
|---|---|---|---|---|
| 2-6B | 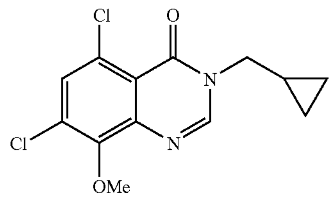 | 96 | (CDCl$_3$): δ 8.15 (s, 1 H), 7.52 (s, 1 H), 4.05 (s, 3 H), 3.83 (d, J = 7.2, 2 H), 1.31 (m, 1 H), 0.66 (m, 2 H), 0.42 (m, 2 H) | |
| 2-6C | 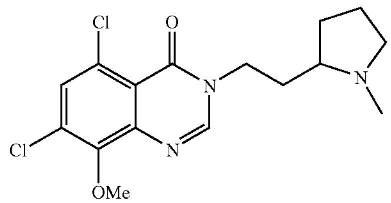 | 99 | (CDCl$_3$): δ 8.12 (s, 1 H), 7.52 (s, 1 H), 4.04 (s, 3 H), 4.00 (m, 2 H), 3.08 (m, 1 H), 2.30 (s, 3 H), 2.25-1.55 (m, 8 H) | m/z 356, 358, 360 (M$^+$ + 1, 100%, 66%, 11%) |
| 2-6D | 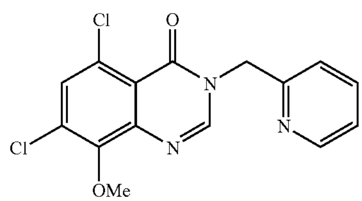 | 99 | (DMSO-d$_6$): δ 8.62 (s, 1 H), 8.47 (m, 1 H), 7.80 (m, 1 H), 7.72 (s, 1 H), 7.45 (d, J = 8.0, 1 H), 7.30 (m, 1 H), 5.25 (s, 2 H), 3.98 (s, 3 H) | |
| 2-6E | 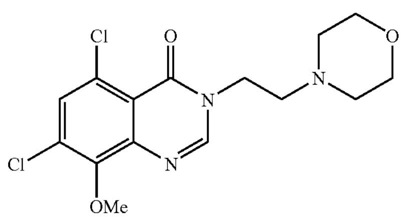 | 95 | (CDCl$_3$): δ 8.06 (s, 1 H), 7.47 (s, 1 H), 4.05 (t, J = 5.8, 2 H), 3.99 (s, 3 H), 3.61 (m, 4 H), 2.66 (t, J = 5.8, 2 H), 2.46 (m, 4 H) | |
| 2-6F | 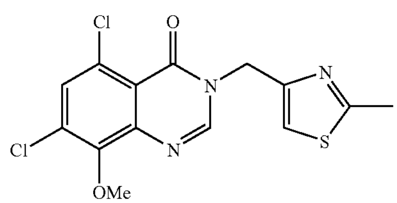 | 98 | (CDCl$_3$): δ 8.42 (s, 1 H), 7.50 (s, 1 H), 7.26 (s, 1 H), 5.17 (s, 2 H), 4.04 (s, 3 H), 2.67 (s, 3 H) | m/z 356, 358, 360 (M$^+$ + 1, 100%, 66%, 11%) |
| 2-6G | 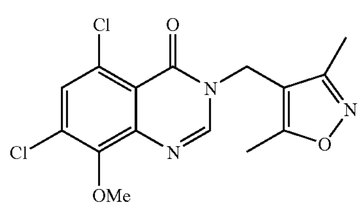 | 94 | (CDCl$_3$): δ 8.23 (s, 1 H), 7.56 (s, 1 H), 4.92 (s, 2 H), 4.04 (s, 3 H), 2.54 (s, 3 H), 2.30 (s, 3 H) | m/z 354, 356, 358 (M$^+$ + 1, 100%, 66%, 11%) |
| 2-6H | 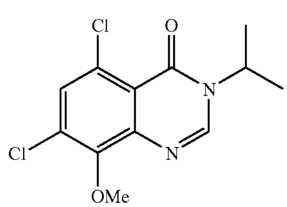 | 56 | (DMSO-d$_6$): δ 8.56 (s, 1 H), 7.72 (s, 1 H), 4.91 (quin, J = 6.8, 1 H), 3.34 (s, 3 H), 1.40 (d, J = 6.8, 6 H), | m/z 287, 289, 291 (M$^+$ + 1, 100%, 66%, 11%) |

TABLE 1-continued

Compounds 2-6A-2-6R prepared according to Example 1

| Compound | Structure | Yield (%) | $^1$H NMR data | Mass spectral data |
|---|---|---|---|---|
| 2-6I | 5,7-dichloro-8-methoxy-3-propylquinazolin-4(3H)-one | 99 | (DMSO-d$_6$): δ 8.49 (s, 1 H), 7.72 (s, 1 H), 3.95 (s, 3 H), 3.89 (m, 2 H), 1.68 (m, 2 H), 0.89 (t, J = 7.3, 3 H) | |
| 2-6J | 5,7-dichloro-3-isobutyl-8-methoxyquinazolin-4(3H)-one | 53 | (DMSO-d$_6$): δ 8.45 (s, 1 H), 7.72 (s, 1 H), 3.95 (s, 3 H), 3.75 (d, J = 7.2, 2 H), 2.10 (m, 1 H), 0.88 (d, J = 6.4, 6 H). | m/z 301, 303, 305 (M$^+$ + 1, 100%, 66%, 11%) |
| 2-6K | 3-butyl-5,7-dichloro-8-methoxyquinazolin-4(3H)-one | 46 | (DMSO-d$_6$): δ 8.48 (s, 1 H), 7.71 (s, 1 H), 3.95 (s, 3 H), 3.92 (t, J = 7.2, 2 H), 1.65 (m, 2 H), 1.31 (m, 2 H), 0.91 (m, 3 H). | m/z 301, 303, 305 (M$^+$ + 1, 100%, 66%, 11%) |
| 2-6L | 3-sec-butyl-5,7-dichloro-8-methoxyquinazolin-4(3H)-one | 28 | (DMSO-d$_6$): δ 8.51 (s, 1 H), 7.72 (s, 1 H), 4.71 (quin, J = 7.2, 1 H), 3.95 (s, 3 H), 1.80 (m, 2 H), 1.39 (d, J = 6.8, 3 H), 0.80 (t, J = 7.2, 3 H). | m/z 301, 303, 305 (M$^+$ + 1, 100%, 66%, 11%) |
| 2-6M | 5,7-dichloro-3-(2-ethoxyethyl)-8-methoxyquinazolin-4(3H)-one | 78 | (DMSO-d$_6$): δ 8.37 (s, 1 H), 7.73 (s, 1 H), 4.10 (t, J = 5.2, 2 H), 3.94 (s, 3 H), 3.62 (d, J = 5.2, 2 H), 3.43 (q, J = 6.8, 2 H), 1.05 (t, J = 6.8, 3 H). | m/z 317, 319, 321 (M$^+$ + 1, 100%, 66%, 11%) |
| 2-6N | 5,7-dichloro-3-(2-(diethylamino)ethyl)-8-methoxyquinazolin-4(3H)-one | 69 | (DMSO-d$_6$): δ 8.35 (s, 1 H), 7.71 (s, 1 H), 3.94 (s, 3 H), 2.62 (m, 4 H), 2.47 (m, 4 H), 0.82 (m, 6 H) | m/z 344, 346, 348 (M$^+$ + 1, 100%, 66%, 11%) |
| 2-6O | 5,7-dichloro-8-methoxy-3-((3-methylpyridin-2-yl)methyl)quinazolin-4(3H)-one | 90 | (DMSO-d$_6$): δ 8.55 (s, 1 H), 8.24 (d, J = 3.7, 1 H), 7.74 (s, 1 H), 7.65 (d, J = 7.5, 1 H), 7.22 (dd, J = 3.7 and 7.5, 1 H), 5.26 (s, 2 H), 3.99 (s, 3 H), 2.43 (s, 3 H) | m/z 336, 338, 340 (M$^+$ + 1, 100%, 66%, 11%) |

TABLE 1-continued

Compounds 2-6A-2-6R prepared according to Example 1

| Compound | Structure | Yield (%) | ¹H NMR data | Mass spectral data |
|---|---|---|---|---|
| 2-6P | 5,7-dichloro-8-methoxy-3-(but-2-enyl)quinazolin-4(3H)-one | 79 | (DMSO-$d_6$): δ 8.45 (s, 1 H), 7.72 (s, 1 H), 5.70 (m, 2 H), 4.47 (d, J = 6.4, 2 H), 3.94 (s, 3 H), 1.65 (d, J = 6.4, 3 H) | m/z 299, 301, 303 (M$^+$ + 1, 100%, 66%, 11%) |
| 2-6Q | bis-quinazolinone linked by pyridine-2,6-diylbis(methylene) | 92 | (DMSO-$d_6$): δ 8.33 (s, 2 H), 7.84 (t, J = 8, 1 H), 7.51 (s, 2 H), 7.39 (d, J = 8.0, 2 H), 5.16 (s, 4 H), 3.95 (s, 3 H), 3.93 (s, 3 H). | m/z 287, 289, 291 (M$^+$ + 1, 82%, 100%, 66%) |
| 2-6R | 5,7-dichloro-8-methoxy-3-ethylquinazolin-4(3H)-one | 26 | (DMSO-$d_6$): δ 8.50 (s, 1 H), 7.71 (s, 1 H), 3.95 (q, J = 7.2, 2 H), 3.94 (s, 3 H), 1.26 (t, J = 7.2, 3 H) | m/z 273, 275, 277 (M$^+$ + 1, 100%, 66%, 11%) |

TABLE 2

Compounds 2-7A1-2-7R1 prepared from 2-6 according to Example 1

| Compound | Structure | Yield (%) and deprotection method in parentheses | ¹H NMR data[#] | Mass spectral data |
|---|---|---|---|---|
| 2-7A1 (1075) | 5,7-dichloro-8-hydroxy-3-(2-(pyrrolidin-1-yl)ethyl)quinazolin-4(3H)-one | 56 (Method A) | (CD$_3$OD): δ 8.12 (s, 1 H), 7.51 (s, 1 H), 4.06 (t, J = 5.5, 2 H), 4.04 (s, 3 H), 2.84 (t, J = 5.5, 2 H), 2.56 (m, 4 H), 1.77 (m, 4 H). | |
| 2-7B1 (1076) | 5,7-dichloro-8-hydroxy-3-(cyclopropylmethyl)quinazolin-4(3H)-one · HBr | 98 (Method A) | (DMSO-$d_6$): δ 8.51 (s, 1 H), 7.59 (s, 1 H), 3.80 (d, J = 6.8, 2 H), 1.28 (m, 1 H), 0.50 (m, 2 H), 0.41 (m, 2 H) | m/z 283, 285, 287 (M$^+$ − 1, 100%, 66%, 11%) |
| 2-7C1 (1078) | 5,7-dichloro-8-hydroxy-3-(2-(1-methylpyrrolidin-2-yl)ethyl)quinazolin-4(3H)-one · 2HBr | 89 (Method B) | (DMSO-$d_6$): δ 8.54 (s, 1 H), 7.61 (s, 1 H), 4.05 (m, 2 H), 3.32 (m, 1 H), 3.05 (m, 1 H), 2.81 (m, 3 H), 2.39–1.68 (m, 7 H) | m/z 342, 344, 346 (M$^+$ + 1, 100%, 66%, 11%) |

TABLE 2-continued

Compounds 2-7A1-2-7R1 prepared from 2-6 according to Example 1

| Compound | Structure | Yield (%) and deprotection method in parentheses | $^1$H NMR data# | Mass spectral data |
|---|---|---|---|---|
| 2-7D1 (1077) | 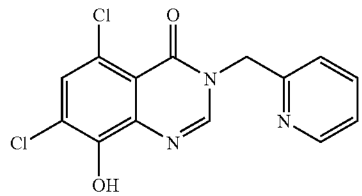 | 75 (Method A) | (DMSO-d$_6$): δ 8.62 (s, 1 H), 8.46 (m, 1 H), 7.80 (m, 1 H), 7.59 (s, 1 H), 7.44 (d, J = 7.9, 1 H), 7.29 (m, 1 H), 5.26 (s, 2 H) | m/z 322, 324, 326 (M$^+$ + 1, 100%, 66%, 11%) |
| 2-7E1 (1079) | 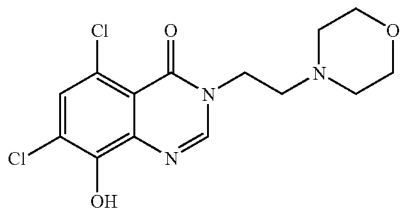 | 69 (Method B) | (CD$_3$OD): δ 8.25 (s, 1 H), 7.48 (s, 1 H), 4.12 (t, J = 6.0, 2 H), 3.65 (t, J = 4.8, 4 H), 2.70 (t, J = 6.0, 2 H), 2.53 (m, 2 H), | m/z 344, 346, 348 (M$^+$ + 1, 100%, 66%, 11%) |
| 2-7F1 (1084) | 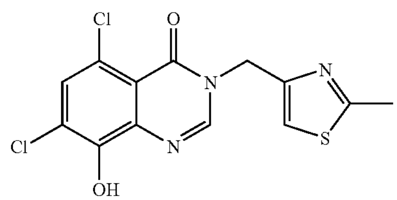 | 74 (Method C) | (CD$_3$OD): δ 8.44 (s, 1 H), 7.48 (s, 1 H), 7.36 (s, 1 H), 5.21 (s, 2 H), 2.66 (s, 3 H) | m/z 342, 344, 346 (M$^+$ + 1, 100%, 66%, 11%) |
| 2-7G1 (1085) | 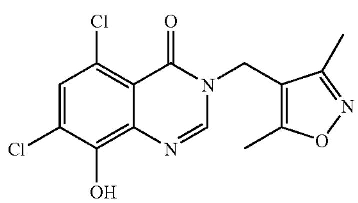 | 38 (Method C) | (DMSO-d$_6$): δ 8.66 (s, 1 H), 7.57 (s, 1 H), 4.91 (s, 2 H), 2.22 (s, 6 H) | m/z 340, 342, 344 (M$^+$ + 1, 100%, 66% 11%) |
| 2-7H1 (1108) | 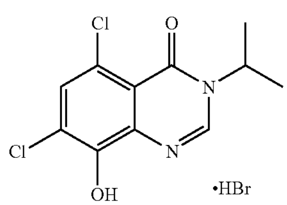 | 68 (Method B) | (DMSO-d$_6$): δ 8.46 (s, 1 H), 7.58 (s, 1 H), 4.92 (quin, J = 6.8, 1 H), 1.43 (d, J = 6.8, 6 H) | m/z 271, 273, 275 (M$^+$ − 1, 100%, 66%, 11%) |
| 2-7I1 (1097) | 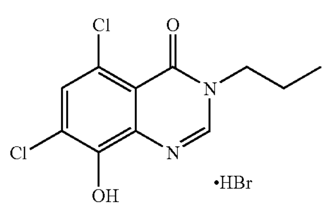 | 77 (Method B) | (DMSO-d$_6$): δ 8.50 (s, 1 H), 7.58 (s, 1 H), 3.90 (m, 2 H), 1.69 (m, 2 H), 0.89 (t, J = 6.3, 3 H) | m/z 273, 275, 277 (M$^+$ + 1, 100%, 66%, 11%) |
| 2-7J1 (1107) | 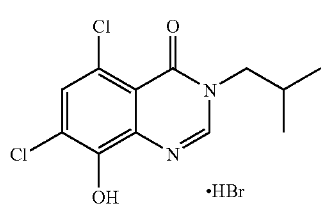 | 79 (Method B) | (DMSO-d$_6$): δ 8.44 (s, 1 H), 7.58 (s, 1 H), 3.76 (d, J = 7.6, 2 H), 2.08 (m, 1 H), 0.88 (d, J = 6.8, 6 H) | m/z 285, 287, 289 (M$^+$ − 1, 100%, 66%, 11%) |

TABLE 2-continued

Compounds 2-7A1-2-7R1 prepared from 2-6 according to Example 1

| Compound | Structure | Yield (%) and deprotection method in parentheses | ¹H NMR data# | Mass spectral data |
|---|---|---|---|---|
| 2-7K1 (1111) | 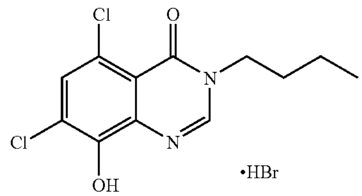 | 77 (Method B) | (DMSO-d$_6$): δ 8.48 (s, 1 H), 7.58 (s, 1 H), 3.93 (t, J = 7.6, 2 H), 1.65 (m, 2 H), 1.30 (m, 2 H), 0.91 (t, J = 7.2, 3 H). | m/z 285, 287, 289 (M$^+$ − 1, 100%, 66%, 11%) |
| 2-7L1 (1112) | 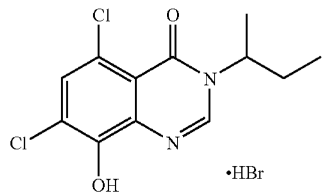 | 62 (Method B) | (DMSO-d$_6$): δ 8.43 (s, 1 H), 7.58 (s, 1 H), 4.71 (quin, J = 6.8, 1 H), 1.82 (m, 2 H), 1.40 (d, J = 6.8, 3 H), 0.80 (t, J = 7.2, 3 H). | m/z 285, 287, 289 (M$^+$ − 1, 100%, 66%, 11%) |
| 2-7M1 (1109) | 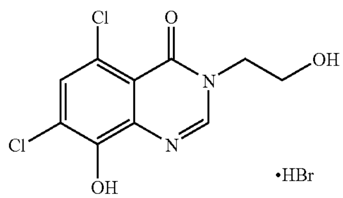 | 98 (Method B) | DMSO-d$_6$): δ 8.48 (s, 1 H), 7.62 (s, 1 H), 4.34 (t, J = 6.4, 2 H), 3.82 (t, J = 6.4, 2 H) | m/z 273, 275, 277 (M$^+$ − 1, 100%, 66%, 11%) |
| 2-7N1 (1110) | 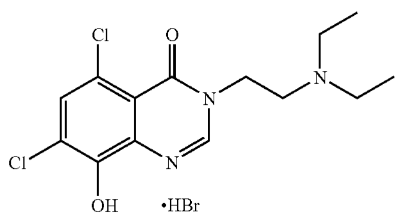 | 85 (Method B) | (DMSO-d$_6$): δ 8.53 (s, 1 H), 7.64 (s, 1 H), 4.30 (m, 2 H), 3.25 (m, 2 H), 2.54 (m, 2 H), 2.44 (m, 2 H), 1.23 (m, 6 H). | m/z 328, 330, 332 (M$^+$ − 1, 100%, 66%, 11%) |
| 2-7O1 (1098) | 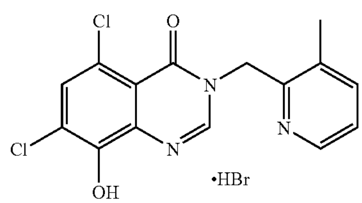 | 83 (Method B) | (DMSO-d$_6$): δ 8.61 (s, 1 H), 8.43 (d, J = 4.7, 1 H), 8.08 (d, J = 3.0, 1 H), 7.63 (s, 1 H), 7.53 (m, 1 H), 5.38 (s, 2 H), 2.50 (s, 3 H) | m/z 336, 338, 340 (M$^+$ + 1, 100%, 66%, 11%) |
| 2-7P1 (1114) | 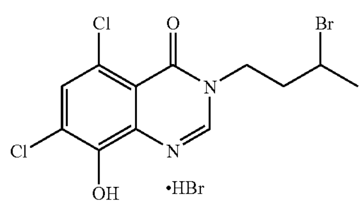 | 99 (Method B) | (DMSO-d$_6$): δ 8.45 (s, 1 H), 7.58 (s, 1 H), 4.33 (m, 1 H), 4.14 (m, 1 H), 4.00 (m, 1 H), 2.22 (m, 2 H), 1.71 (d, J = 6.8, 3 H) | m/z 365, 367, 369 (M$^+$ + 1, 45%, 66%, 30%) |
| 2-7Q1 (1101) | 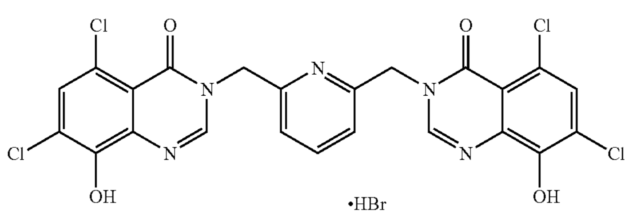 | 82 (Method B) | (DMSO-d$_6$): δ 8.42 (s, 2 H), 7.81 (t, J = 8, 1 H), 7.43 (s, 2 H), 7.32 (d, J = 8, 2 H), 5.18 (s, 4 H) | m/z 562, 564, 566 (M$^+$ − 1, 82%, 100%, 66%) |

TABLE 2-continued

Compounds 2-7A1-2-7R1 prepared from 2-6 according to Example 1

| Compound | Structure | Yield (%) and deprotection method in parentheses | $^1$H NMR data[#] | Mass spectral data |
|---|---|---|---|---|
| 2-7R1 (1115) | 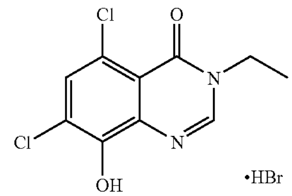 | 95 (Method B) | (DMSO-$d_6$): δ 8.51 (s, 1 H), 7.57 (s, 1 H), 3.97 (q, J = 7.2, 2 H), 1.27 (t, J = 7.2, 3 H) | m/z 259, 261, 263 ($M^+$ + 1, 100%, 66%, 11%) |
| 2-7S1 (1126) | 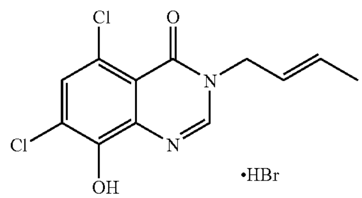 | 44 (Method A) | (DMSO-$d_6$): δ 8.44 (s, 1 H), 7.59 (s, 1 H), 5.70 (m, 2 H), 4.49 (d, J = 5.6, 2 H), 1.65 (d, J = 6.0, 3 H) | m/z 285, 287, 289 ($M^+$ + 1, 100%, 66%, 11%) |

[#]chemical shifts for the 8-OH and HBr (where applicable) have not been included in the assignments

Preparation of 2-amino-4,6-dichloro-3-hydroxybenzoic acid (1-8)

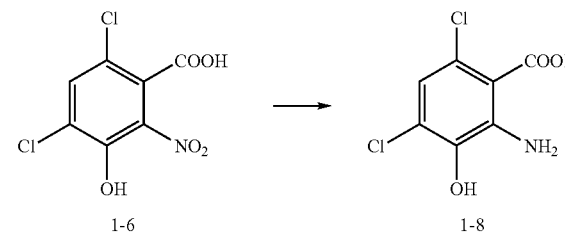

A mixture of 4,6-dichloro-3-hydroxy-2-nitrobenzoic acid (1-6) (700 mg, 2.78 mmol), iron powder (400 mg, 7.16 mmol) and glacial acetic acid (13 mL) was heated at 80° C. for 50 minutes, cooled, and the solids filtered off. The filtrate was concentrated to a brown solid. Subsequent $SiO_2$-gel column chromatography (ethyl acetate/HOAc, 100:1-100:3) gave 2-amino-4,6-dichloro-3-hydroxybenzoic acid (1-8) as a light brown solid (582 mg, 94%). —$^1$H NMR (DMSO-$d_6$): δ 6.68 (s); this is consistent with the literature.[4]

Preparation of 4,6-dichloro-2-formylamino-3-hydroxybenzoic acid (2-8)

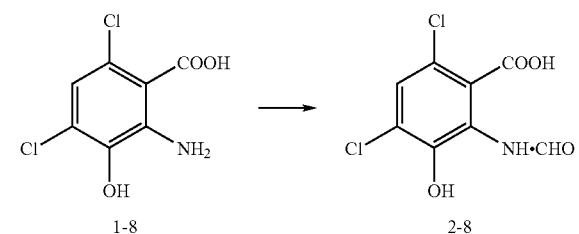

A solution of formic acid (1.04 mL of 90% solution) and acetic anhydride (2 mL) was heated at 50-60° C. for 2 hours and cooled. 2-Amino-4,6-dichloro-3-hydroxybenzoic acid (1-8) (425 mg, 1.91 mmol) was then added portionwise to the stirred acetic formic anhydride at room temperature. After 2.5 hours, the reaction mixture was poured onto a mixture of ice and water; the solid was isolated via filtration. This provided 4,6-dichloro-2-formylamino-3-hydroxybenzoic acid (2-8) as an orange solid (320 mg, 67%). —$^1$H NMR (DMSO-$d_6$): δ 8.76 (s, 1H), 8.29 (s, 1H), 8.13 (s, 1H); mass spectrum: m/z 248, 250, 252 ($M^+$−1, 100%, 66%, 11%).

Example 2

$PCl_3$-mediated condensation of 4,6-dichloro-2-formylamino-3-hydroxybenzoic acid (2-8) with amines

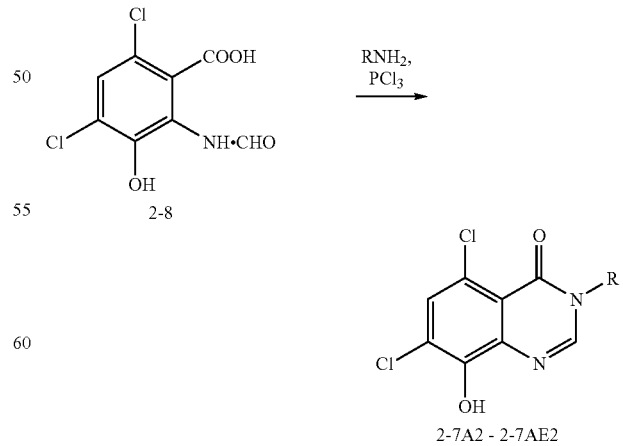

To a stirring mixture of 4,6-dichloro-2-formylamino-3-hydroxybenzoic acid (2-8) (200 mg, 0.80 mmol), the amine (0.88 mmol) and toluene (5 mL) was added a solution of PCl₃ (0.12 mL, 1.38 mmol) in toluene (1 mL) dropwise over 2 minutes. The resulting suspension was heated under reflux for 4-16 hours, and cooled. Saturated NaHCO₃ was added to pH 9. The pH of the mixture was then re-adjusted to 7 (5N HCl) and extracted with dichloromethane (3×), and the extracts combined and dried (Na₂SO₄). The volatiles were removed which afforded the 5,7-dichloro-8-hydroxy-3-(substituted)-3H-quinazolin-4-one (2-7). In some cases, the crude product was purified via washing with an appropriate solvent, typically diethyl ether or 5% methanol in diethyl ether, or SiO₂-gel chromatography or recrystallization; characterisation data for compounds 2-7A2 and 2-7M2 are shown in Table 3. Other compounds 2-7 prepared from 2-8 according to Example 2 are shown in Table 4.

Examples of amines used in Example 2: (C-thiazol-2-yl)methylamine gives 2-7A2, 2-(2-aminoethyl)pyridine gives 2-7B2, 3-aminopyridine gives 2-7C2, 4-aminomorpholine gives 2-7D2, 1-amino-4-methylpiperazine gives 2-7E2, 4-(aminomethyl)piperidine gives 2-7F2, 5-amino-1-ethylpyrazole gives 2-7G2, 5-amino-2-methoxypyridine gives 2-7H2, 2-amino-1-methylbenzamidazole gives 2-7I2, 2-amino-5-methylpyridine gives 2-7J2,2-amino-5-chloropyridine gives 2-7K2, 1-aminopiperidine gives 2-7L2 and 1-aminopyrrolidine gives 2-7M2. In the case of amine hydrochloride salts, appropriate equivalents of a base such as triethylamine were added to the reaction mixture. Other compounds prepared according to Example 2 are 2-7O2-2-7AE2 (Table 4).

TABLE 3

Compounds 2-7 prepared from 2-8 according to Example 2

| Compound | Structure | Yield (%) | ¹H NMR data# | Mass spectral data |
|---|---|---|---|---|
| 2-7A2 (1082) | 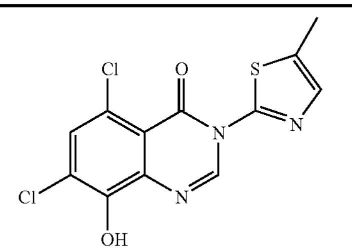 | 50 | (DMSO-d₆): δ 9.23 (s, 1 H), 7.71 (s, 1 H), 7.53 (s, 1 H), 2.50 (s, 3 H) | m/z 326, 328, 330 (M⁺ − 1, 100%, 66%, 11%) |
| 2-7B2 (1091) | 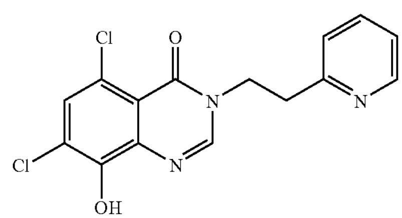 | 31 | (DMSO-d₆): δ 10.6 (br, 1 H), 8.50 (d, J = 4.6, 1 H), 8.24 (s, 1 H), 7.71 (m, 1 H), 7.59 (s, 1 H), 7.29 (d, J = 7.9, 1 H), 7.25 (m, 1 H), 4.34 (t, J = 6.8, 2 H), 3.19 (t, J = 6.8, 2 H) | m/z 334, 336, 338 (M⁺ − 1, 100%, 66%, 11%) |
| 2-7C2 (1092) | 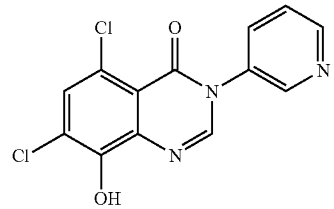 | 60 | (DMSO-d₆): δ 8.76 (d, J = 2.4, 1 H), 8.70 (d, J = 4.4, 1 H), 8.47 (s, 1 H), 8.03 (d, J = 8, 1 H), 7.67 (s, 1 H), 7.62 (dd, J = 8, 4.8, 1 H). | m/z 308, 310, 312 (M⁺ + 1, 100%, 66%, 11%) |
| 2-7D2 (1080) | 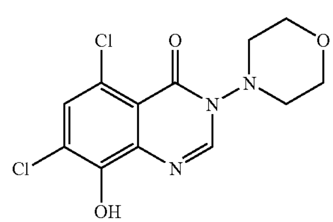 | 43 | (CDCl₃): δ 8.18 (s, 1 H), 7.48 (s, 1 H), 4.22 (br, 2 H), 3.95 (br, 2 H), 3.78 (br, 2 H), 2.93 (br, 2 H) | m/z 314, 316, 318 (M⁺ − 1, 100%, 66%, 11%) |
| 2-7E2 (1081) | 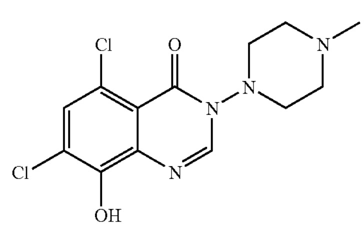 | 16 | (CDCl₃): δ 8.15 (s, 1 H), 7.45 (s, 1 H), 4.30 (br, 2 H), 3.10 (br 2 H), 2.59 (s, 3 H), 1.90 (br, 4 H) | m/z 329, 331, 333 (M⁺ + 1, 100%, 66%, 11%) |

TABLE 3-continued
Compounds 2-7 prepared from 2-8 according to Example 2
| Compound | Structure | Yield (%) | ¹H NMR data# | Mass spectral data |
|---|---|---|---|---|
| 2-7F2 (1094) | 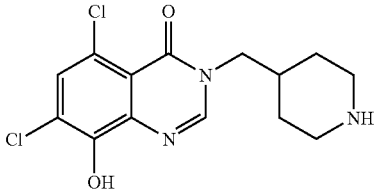 | | | m/z 328, 330, 332 (M⁺ + 1, 100%, 66%, 11%) |
| 2-7G2 (1088) | 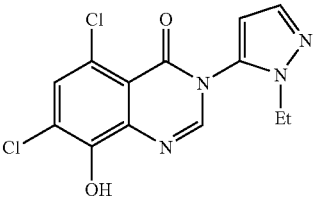 | 42 | (CDCl₃): δ 7.89 (s, 1 H), 7.49 (s, 1 H), 7.40 (s, 1 H), 6.22 (s, 1 H), 3.84 (m, 2 H), 1.32 (m, 3 H) | m/z 325, 327, 329 (M⁺ + 1, 100%, 66%, 11%) |
| 2-7H2 (1093) | 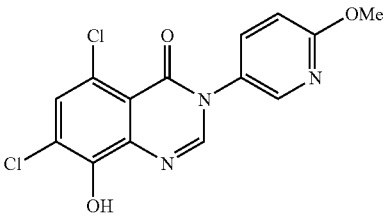 | 45 | (DMSO-d₆): δ 8.38 (s, 1 H), 7.74 (d, J = 4.0, 1 H), 7.64 (s, 1 H), 7.57 (dd, J = 2.4 and 9.6, 1 H), 6.42 (d, J = 9.6, 1 H), 3.91 (s, 3 H) | m/z 338, 340, 342 (M⁺ + 1, 100%, 66%, 11%) |
| 2-7I2 (1083) | 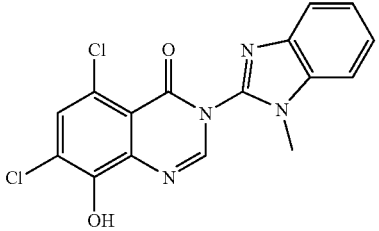 | 65 | (DMSO-d₆): δ 8.17 (br, 1 H), 7.71 (m, 2 H), 7.41 (m, 2 H), 7.33 (m, 1 H), 3.70 (s, 3 H) | m/z 361, 363, 365 (M⁺ + 1, 100%, 66%, 11%) |
| 2-7J2 (1089) | 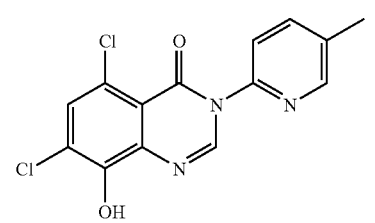 | 45 | (DMSO-d₆): δ 8.55 (s, 1 H), 8.48 (s, 1 H), 7.88 (m, 1 H), 7.68 (m, 2 H), 2.40 (s, 3 H) | m/z 322, 324, 326 (M⁺ + 1, 100%, 66%, 11%) |
| 2-7K2 (1087) | 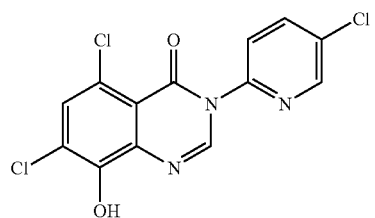 | 16 | (DMSO-d₆): δ 8.76 (d, J = 2.4, 1 H), 8.59 (s, 1 H), 8.24 (dd, J = 2.4 and 8.4, 1 H), 7.86 (d, J = 8.4, 1 H), 7.70 (s, 1 H) | m/z 342, 344, 346 (M⁺ + 1, 100%, 66%, 11%) |

TABLE 3-continued

Compounds 2-7 prepared from 2-8 according to Example 2

| Compound | Structure | Yield (%) | $^1$H NMR data$^\#$ | Mass spectral data |
|---|---|---|---|---|
| 2-7L2 (1086) | 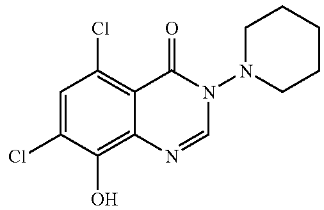 | 45 | (DMSO-d$_6$): δ 8.27 (s, 1 H), 7.59 (s, 1 H), 3.55 (s, 2 H), 3.15 (s, 2 H), 1.65 (m, 6 H). | m/z 314, 316, 318 (M$^+$ + 1, 100%, 66%, 11%) |
| 2-7M2 (1090) | 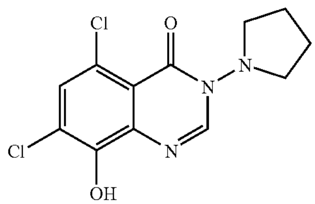 | 33 | (CDCl$_3$): δ 8.23 (s, 1 H), 7.36 (s, 1 H), 3.60 (m, 2 H), 3.37 (m, 1 H), 3.10 (m, 1 H), 1.91 (m, 4 H) | m/z 303, 305, 307 (M$^+$ + 1, 100%, 66%, 11%) |

$^\#$the chemical shift for the 8-OH has not been included in the assignments

TABLE 4

Other 2-7N2-2-7AE2 prepared from 2-8 according to Example 2

| Compound | Structure |
|---|---|
| 2-7N2 | 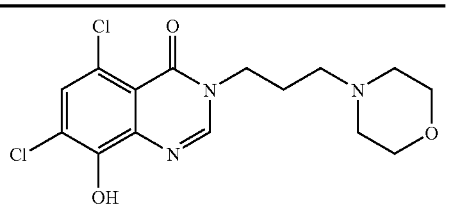 |
| 2-7O2 | 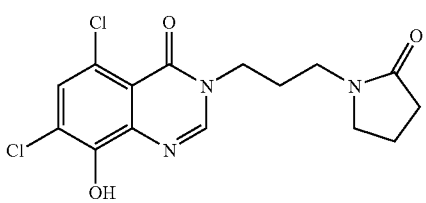 |
| 2-7P2 | 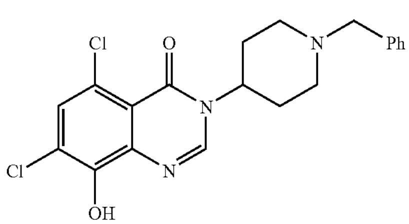 |
| 2-7Q2 | 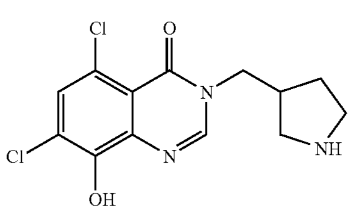 |
| 2-7R2 | |
| 2-7S2 | |
| 2-7T2 | |

TABLE 4-continued

Other 2-7N2-2-7AE2 prepared from 2-8 according to Example 2

| Compound | Structure |
|---|---|
| 2-7U2 | 5,7-dichloro-8-hydroxy-3-(1,3,5-trimethyl-1H-pyrazol-4-yl)quinazolin-4(3H)-one |
| 2-7V2 | 5,7-dichloro-8-hydroxy-3-(pyridin-4-ylmethyl)quinazolin-4(3H)-one |
| 2-7W2 | 5,7-dichloro-8-hydroxy-3-(thiazol-2-ylmethyl)quinazolin-4(3H)-one |
| 2-7X2 | 5,7-dichloro-8-hydroxy-3-(piperidin-4-yl)quinazolin-4(3H)-one |
| 2-7Y2 | 5,7-dichloro-8-hydroxy-3-(2,3,5,6-tetrafluoropyridin-4-yl)quinazolin-4(3H)-one |
| 2-7Z2 | 5,7-dichloro-3-(4,5-dimethylthiazol-2-yl)-8-hydroxyquinazolin-4(3H)-one |
| 2-7AA2 | 5,7-dichloro-3-(6-fluorobenzo[d]thiazol-2-yl)-8-hydroxyquinazolin-4(3H)-one |
| 2-7AB2 | 5,7-dichloro-3-(2,4-difluorophenyl)-8-hydroxyquinazolin-4(3H)-one |
| 2-7AC2 | 5,7-dichloro-3-(3-fluorophenyl)-8-hydroxyquinazolin-4(3H)-one |
| 2-7AD2 | 5,7-dichloro-8-hydroxy-3-(2-isopropoxyethyl)quinazolin-4(3H)-one |
| 2-7AE2 | 5,7-dichloro-8-hydroxy-3-(2,2,6,6-tetramethylpiperidin-4-yl)quinazolin-4(3H)-one |

TABLE 5
Other compounds prepared according to Examples 1 and 2
| Compound | Structure |
|---|---|
| 8A1 | 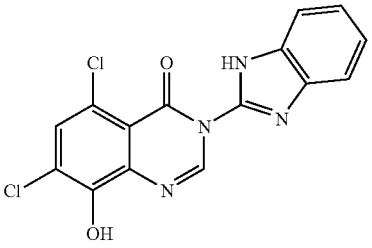 |
| 8B1 | 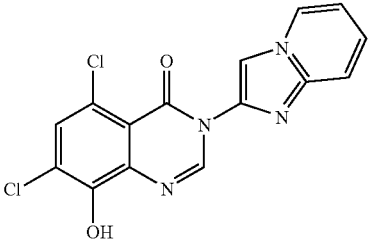 |
| 8C1 | 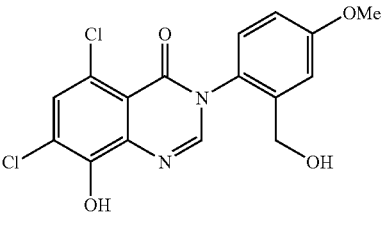 |
| 8D1 | 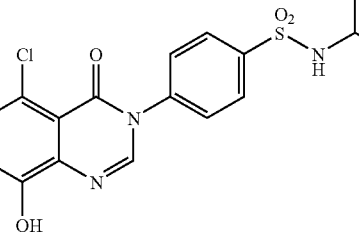 |
| 8E1 | 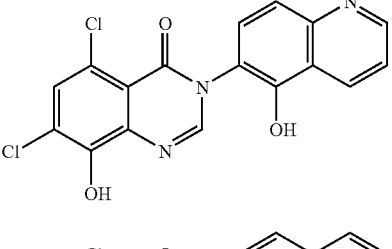 |
| 8F1 | 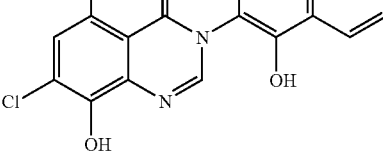 |
| 8G1 | 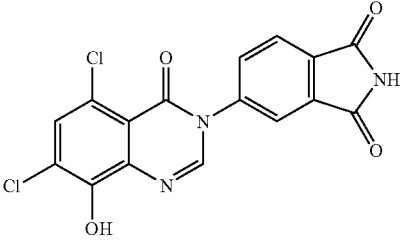 |
| 8H1 | 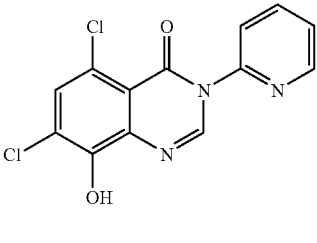 |
| 8I1 | 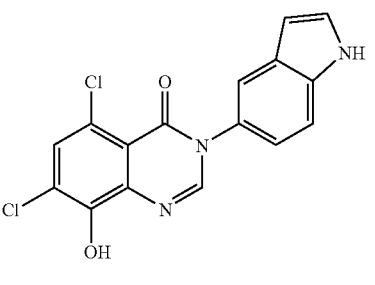 |
| 8J1 | 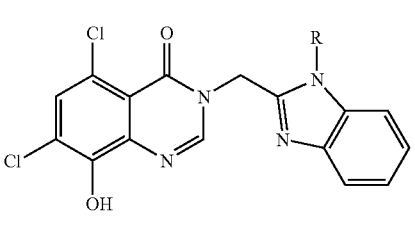<br>R = H, Me, Et, n-propyl |
| 8K1 | 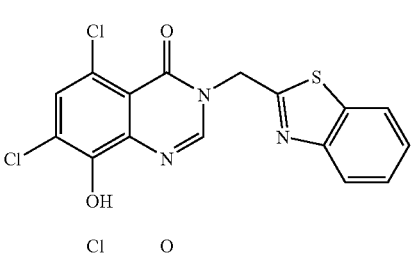 |
| 8L1 | 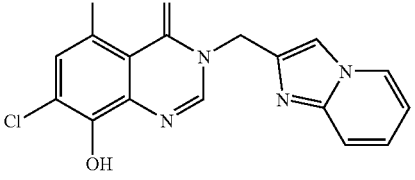 |

TABLE 5-continued

Other compounds prepared according to Examples 1 and 2

| Compound | Structure |
|---|---|
| 8M1 | (structure: 5,7-dichloro-8-hydroxy-quinazolin-4(3H)-one linked at N3 to phthalimide N-R) |

R = Me, Et, iso-propyl, n-propyl, n-butyl

| Compound | Structure |
|---|---|
| 8N1 | (structure: 5,7-dichloro-8-hydroxy-quinazolin-4(3H)-one linked to pyridine-benzothiazole) |
| 8O1 | (structure: 5,7-dichloro-8-hydroxy-quinazolin-4(3H)-one-N-CH₂-C(O)-NH-(2-pyridyl)) |
| 8P1 | (structure: 5,7-dichloro-8-hydroxy-quinazolin-4(3H)-one-N-CH₂-C(O)-NH-n-propyl) |
| 8Q1 | (structure: 5,7-dichloro-8-hydroxy-quinazolin-4(3H)-one-N-CH₂-C(O)-N(Et)₂) |
| 8R1 | (structure: 5,7-dichloro-8-hydroxy-quinazolin-4(3H)-one-N-CH₂-C(O)-NH-benzothiazol-2-yl) |

| Compound | Structure |
|---|---|
| 8S1 | (structure: 5,7-dichloro-8-hydroxy-quinazolin-4(3H)-one-N-CH₂-C(O)-NH-benzimidazol-2-yl, N-R) |

R = H, Me, Et, n-propyl

| Compound | Structure |
|---|---|
| 8T1 | (structure: 5,7-dichloro-8-hydroxy-quinazolin-4(3H)-one-N-CH₂-C(O)-NH-imidazo[1,2-a]pyridin-2-yl) |
| 8U1 | (structure: 5,7-dichloro-8-hydroxy-quinazolin-4(3H)-one-N-CH₂-C(O)-NH-indol-3-yl, N-R) |

R = H, Me, Et, n-propyl

| Compound | Structure |
|---|---|
| 8V1 | (structure: 5,7-dichloro-8-hydroxy-quinazolin-4(3H)-one-N-CH₂-C(O)-NH-propargyl) |
| 8W1 | (structure: 5,7-dichloro-8-hydroxy-quinazolin-4(3H)-one-N-CH₂CH₂-phthalimide) |
| 8X1 | (structure: 5,7-dichloro-8-hydroxy-quinazolin-4(3H)-one-N-CH₂CH₂-isoindolin-2-yl) |

TABLE 5-continued

Other compounds prepared according to Examples 1 and 2

| Compound | Structure |
|---|---|
| 8Y1 | 5,7-dichloro-8-hydroxy-3-[2-(1-oxoisoindolin-2-yl)ethyl]quinazolin-4(3H)-one |
| 8Z1 | 5,7-dichloro-8-hydroxy-3-[2-(1H-indol-3-yl)ethyl]quinazolin-4(3H)-one |
| 8A2 | 5,7-dichloro-8-hydroxy-3-[(2-(NHR)pyridin-4-yl)methyl]quinazolin-4(3H)-one; R = H, Me, Et |
| 8B2 | 5,7-dichloro-8-hydroxy-3-[(2-(NHR)benzothiazol-6-yl)methyl]quinazolin-4(3H)-one; R = H, Me, Et |
| 8C2 | 5,7-dichloro-8-hydroxy-3-[(2-(NHR)benzimidazol-6-yl)methyl]quinazolin-4(3H)-one; R = H, Me, Et, n-propyl |
| 8D2 | 5,7-dichloro-3-[2-(ethylamino)ethyl]-8-hydroxyquinazolin-4(3H)-one |
| 8E2 | 5,7-dichloro-8-hydroxy-3-{2-[(4-fluorophenyl)sulfonylamino]ethyl}quinazolin-4(3H)-one |
| 8F2 | 5,7-dichloro-8-hydroxy-3-[2-(propylsulfonylamino)ethyl]quinazolin-4(3H)-one |
| 8G2 | 5,7-dichloro-8-hydroxy-3-[2-(2-oxoindolin-1-yl)ethyl]quinazolin-4(3H)-one |
| 8H2 | 5,7-dichloro-8-hydroxy-3-(1-R-2-oxoindolin-5-yl)quinazolin-4(3H)-one; R = H, Me, Et, n-propyl |
| 8I2 | 5,7-dichloro-8-hydroxy-3-[(2-aminoquinolin-6-yl)methyl]quinazolin-4(3H)-one |
| 8J2 | 3-(2-aminoethyl)-5,7-dichloro-8-hydroxyquinazolin-4(3H)-one |

Example 3

Preparation of 2,3-disubstituted-3H-quinazolin-4-ones (4-9)

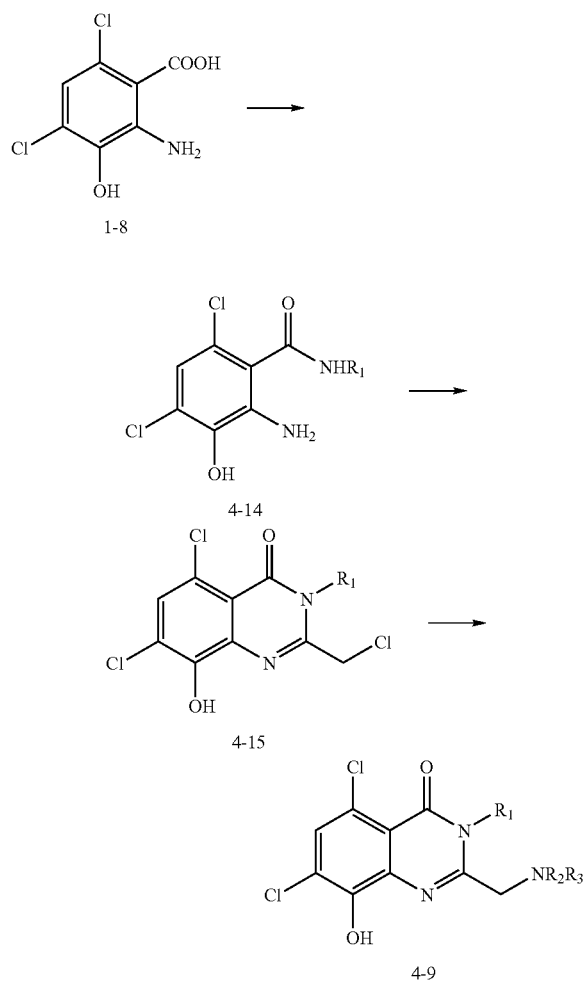

Step 1: To a solution of the acid 1-8 (1.00 g, 4.50 mmol) in anhydrous benzene (8.3 mL) was added thionyl chloride (2.09 g, 17.6 mmol) dropwise under an argon atmosphere. The mixture was heated under reflux for 5 h after which time the excess thionyl chloride and benzene were removed by evaporation. The residue was dissolved in anhydrous dichloromethane (8.3 mL), cooled to 0° C., and treated with n-propylamine (798 mg, 13.5 mmol). The mixture was stirred at 0° C. for 15 min, then warmed to room temperature and stirred for a further 16 h. Evaporation and purification of the crude residue via column chromatography (ethyl acetate/petroleum ether, 3:7-1:1) afforded the benzamide, 2-amino-4,6-dichloro-3-hydroxy-N-(n-propyl)lbenzamide (4-14, $R_1$=n-propyl), as an orange solid (550 mg, 46%).

2-Amino-4,6-dichloro-3-hydroxy-N-propylbenzamide: $^1$H NMR (DMSO-$d_6$): δ 8.39 (t, J=5.6, 1H), 6.67 (s, 1H), 4.94 (br, 1H), 3.16 (m, 2H), 2.44 (m, 2H), 1.50 (m, 2H), 0.88 (m, 3H).

Step 2: To a solution of 2-amino-4,6-dichloro-3-hydroxy-N-propylbenzamide (1.00 g, 4.50 mmol) in glacial acetic acid (5.5 mL) was added chloroacetyl chloride (718 mg, 6.36 mmol) dropwise under an argon atmosphere. The mixture was heated under reflux for 2 h and then stirred at room temperature for 1 h. The reaction mixture was evaporated in vacuo and the residue neutralised with 2M NaOH. The precipitate was isolated via filtration, washed with water, and dried in vacuo. Dichloromethane (10 mL) was added to the resulting residue and the insoluble material was filtered off. The filtrate was concentrated to afford the chloride, 2-chloromethyl-5,7-dichloro-8-hydroxy-3-n-propyl-3H-quinazolin-4-one (4-15, $R_1$=n-propyl), as an orange solid (600 mg, 89%).

2-Chloromethyl-5,7-dichloro-8-hydroxy-3-n-propyl-3H-quinazolin-4-one: $^1$H NMR (DMSO-$d_6$): δ 7.86 (s, 1H), 5.15 (s, 2H), 4.27 (s, 2H), 1.52 (m, 2H), 0.93 (m, 3H); mass spectrum: m/z 323, 325, 327 (M$^+$+1, 100%, 66%, 11%).

Step 3: To a solution of 2-chloromethyl-5,7-dichloro-8-hydroxy-3-n-propyl-3H-quinazolin-4-one (285 mg, 0.886 mmol) in anhydrous THF (1.3 mL) was added a solution of methylamine in ethanol (7.5 mL of a 8.0M solution, 60 mmol) dropwise under an argon atmosphere. The mixture was stirred at room temperature for 18 h, then concentrated, and to the resulting residue was added 2M HCl (5 mL). The mixture was evaporated and more 2M HCl (5 mL) was added. The residue was evaporated and the procedure repeated two more times. The mixture was triturated with dichloromethane and dried in vacuo to yield 5,7-dichloro-8-hydroxy-2-methylaminomethyl-3-n-propyl-3H-quinazolin-4-one hydrochloride (4-9A) as a yellow solid (157 mg, 50%)(Table 6).

Other 2,3-disubstituted-3H-quinazolin-4-ones (4-9B-4-9E) prepared via substitution of n-propylamine (Step 1) and methylamine (Step 3) in Example 3 for the appropriate amine(s) are given in Table 6.

TABLE 6

Compounds 4-9A-4-9E prepared according to Example 3

| Compound | Structure | $^1$H NMR data | Mass spectral data |
|---|---|---|---|
| 4-9A | 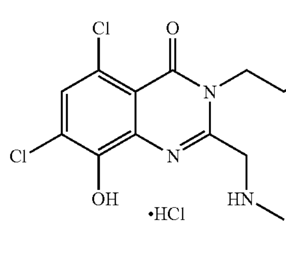 | (DMSO-$d_6$): δ 7.06 (s, 1 H), 4.57 (m, 2 H), 3.83 (t, J = 6.0, 2 H), 3.14 (m, 1 H), 2.80 (d, J = 4.4, 3 H), 1.49 (q, J = 7.2, 2 H), 0.90 (t, J = 7.2, 3 H) | m/z 316, 318, 320 (M$^+$ + 1, 100%, 66%, 11%) |

TABLE 6-continued
Compounds 4-9A-4-9E prepared according to Example 3
| Compound | Structure | ¹H NMR data | Mass spectral data |
|---|---|---|---|
| 4-9B | 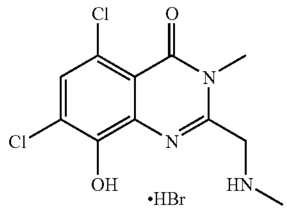 | (DMSO-$d_6$): δ 7.66 (s, 1 H), 4.52 (br, 2 H), 3.41 (s, 3 H), 3.15 (br, 1 H), 2.73 (br, 3 H) | m/z 288, 290, 292 ($M^+ + 1$, 100%, 66%, 11%) |
| 4-9C | 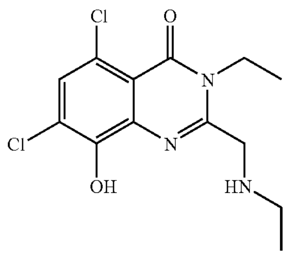 | | |
| 4-9D | 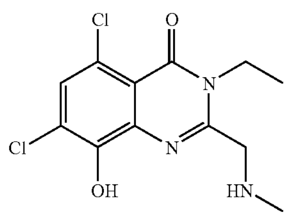 | | |
| 4-9E | 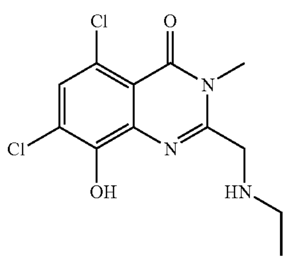 | | |
Example 4
Preparation of 2-substituted-3H-quinazolin-4-ones (4-16A-4-16D)
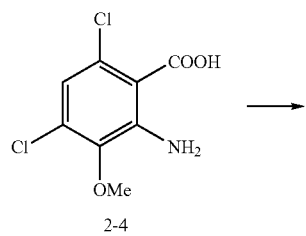
2-4
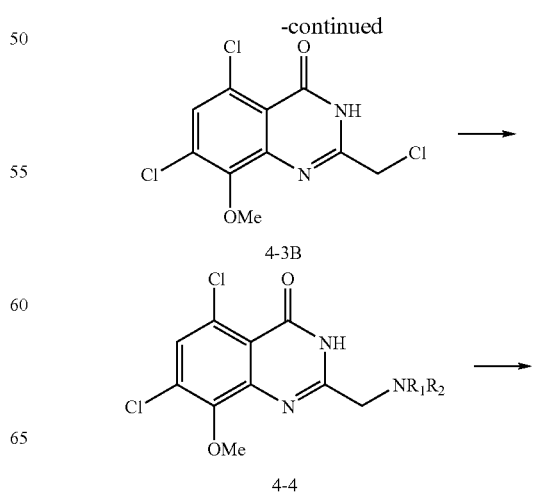
4-3B
4-4

-continued

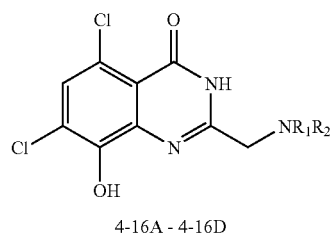

4-16A - 4-16D

To an ice-cooled solution of sodium methoxide in methanol (2.8 mL of a 0.32 M solution, 0.89 mmol) was added chloroacetonitrile (0.25 mL, 3.90 mmol) dropwise under an argon atmosphere.[7] The reaction mixture was allowed to stir at RT for 30 minutes and then re-cooled to 0° C. prior to the addition of a solution of 2-4 (0.80 g, 3.39 mmol) in anhydrous methanol (14 mL). The solution was left to stir at RT for 20 h and heated under reflux for an additional 20 h. Evaporation and purification of the resulting residue via column chromatography (ethyl acetate/petroleum ether, 3:7) afforded the chloride 4-3B as a white solid (225 mg, 23%).

Subsequent treatment of 4-3B with a suitable amine according to conditions as described in Step 3 in Example 3 gave the 2-substituted-8-methoxy-3H-quinazolin-4-one: ethylamine gave 4-4A, 1-propylamine gave 4-4B, diethylamine gave 4-4C, and dimethylamine gave 4-4D. Subsequent respective removal of the 8-methoxy protecting group according to the general deprotection procedure (Example 1, Method A) gave 4-16A-4-16D (Table 7).

TABLE 7

| Compound | Structure | $^1$H NMR data | Mass spectral data |
|---|---|---|---|
| 4-4A | 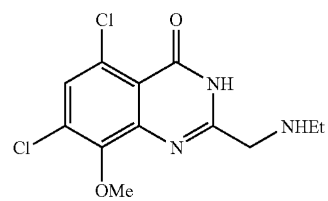 | | |
| 4-4B | 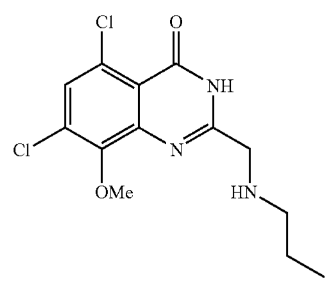 | | |
| 4-4C | 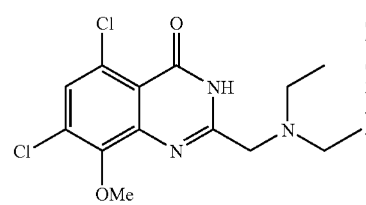 | (DMSO-$d_6$): δ 7.63 (s, 1 H), 3.94 (s, 3 H), 3.55 (s, 2 H), 2.61 (q, J = 7.2, 4 H), 0.98 (t, J = 7.2, 6 H) | m/z 328, 330, 332 (M$^+$ + 1, 100%, 66%, 11%) |
| 4-4D | 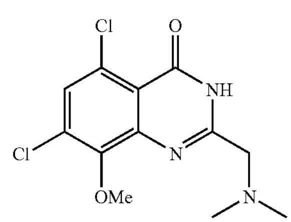 | (DMSO-$d_6$): δ 7.64 (s, 1 H), 3.95 (s, 3 H), 2.27 (s, 6 H) | m/z 302, 304, 306 (M$^+$ + 1, 100%, 66%, 11%) |

Compounds 4-4A-4-4D and 4-16A-4-16D prepared according to Example 4

TABLE 7-continued

Compounds 4-4A-4-4D and 4-16A-4-16D prepared according to Example 4

| Compound | Structure | $^1$H NMR data | Mass spectral data |
|---|---|---|---|
| 4-16A | (structure) | | |
| 4-16B | (structure) | | |
| 4-16C | (structure) | (DMSO-$d_6$): δ 7.36 (s, 1 H), 4.34 (s, 2 H), 3.28 (q, J = 7.2, 4 H), 1.20 (t, J = 7.2, 6 H) | m/z 316, 318, 320 (M$^+$ + 1, 100%, 66%, 11%) |
| 4-16D | (structure) | (DMSO-$d_6$): δ 7.63 (s, 1 H), 4.39 (s, 2 H), 2.99 (s, 6 H) | m/z 288, 290, 292 (M$^+$ + 1, 100%, 66%, 11%) |

Preparation of 3-Amino-5,7-dichloro-8-hydroxy-3H-quinazolin-4-one hydrobromide (5-4 or PB 1099)

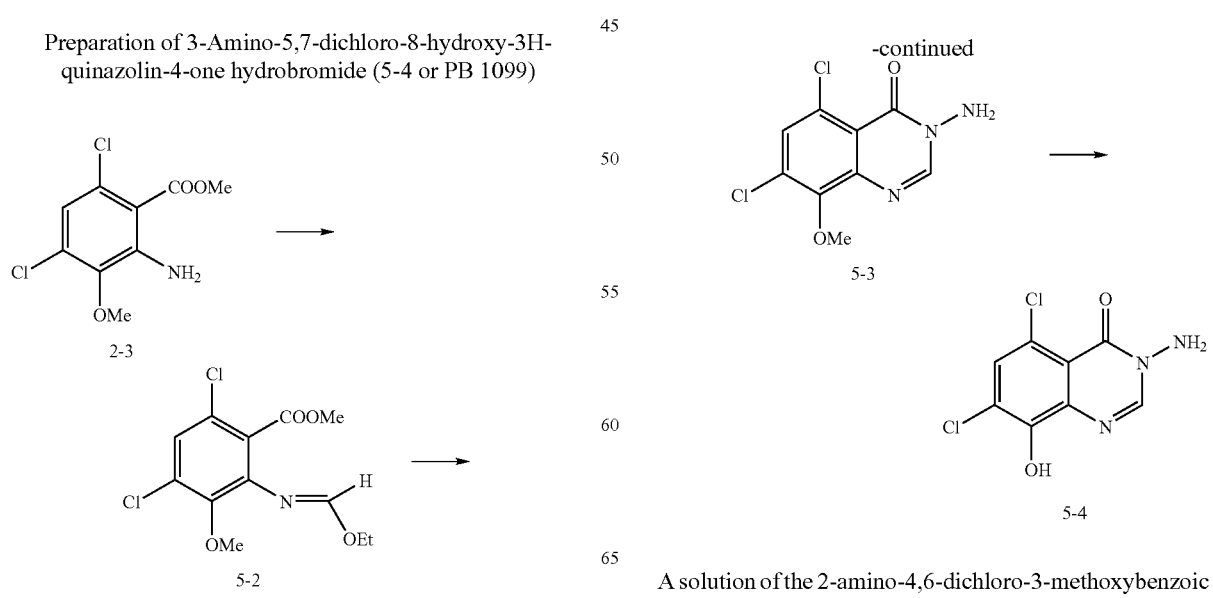

A solution of the 2-amino-4,6-dichloro-3-methoxybenzoic acid methyl ester (2-3) (6.35 g, 25.4 mmol) and triethyl orthoformate (60 mL, 361 mmol) was heated under reflux for 5 days. The solution was cooled to room temperature and evaporated under reduced pressure to afford the imidate, 4,6-dichloro-2-ethoxymethyleneamino-3-methoxybenzoic acid methyl ester (5-2), and starting material (7.80 g) as a brown oil; 5-2:2-3-9:1.

4,6-Dichloro-2-ethoxymethyleneamino-3-methoxybenzoic acid methyl ester (5-2): $^1$H NMR (DMSO-$d_6$): δ 7.99 (s, 1H), 7.48 (s, 1H), 4.22 (q, 2H), 3.79 (s, 3H), 3.62 (s, 3H), 1.28 (t, J=7.2, 3H).

To an ice-cooled solution of the imidate 5-2 (400 mg, 1.31 mmol) in ethanol (12 mL), was added under an argon atmosphere, hydrazine hydrate (1.8 mL, 57.8 mmol). After 15 min, the solution was warmed to room temperature and stirred for a further 2 h. The thick suspension was diluted with ethanol and filtered. The solid was washed with cold ethanol and dried under vacuum to give 3-amino-5,7-dichloro-8-methoxy-3H-quinazolin-4-one (5-3) as a white fluffy solid (289 mg, 85%).

3-Amino-5,7-dichloro-8-methoxy-3H-quinazolin-4-one (5-3): $^1$H NMR (DMSO-$d_6$): δ 8.48 (s, 1H), 7.74 (s, 1H), 5.85 (s, 2H), 3.94 (s, 3H); mass spectrum: m/z 260, 262, 264 (M$^+$+1, 100%, 66%, 11%).

A solution of 5-3 (60 mg, 0.231 mmol) and 48% aqueous hydrobromic acid (2 mL) was heated at 120° C. for 2 h. The solution was cooled to room temperature and the precipitate was isolated via filtration, washed successively with dichloromethane and diethyl ether, and dried in vacuo to provide 3-amino-5,7-dichloro-8-hydroxy-3H-quinazolin-4-one hydrobromide (5-4) as a white solid (44 mg, 58%).

3-Amino-5,7-dichloro-8-hydroxy-3H-quinazolin-4-one hydrobromide (5-4): $^1$H NMR (DMSO-$d_6$): δ 8.44 (s, 1H), 7.60 (s, 1H); m/z 246, 248, 250 (M$^+$+1, 100%, 66%, 11%).

Example 5

Preparation of 3-(substituted)amino-5,7-dichloro-8-hydroxy-3H-quinazolin-4-ones

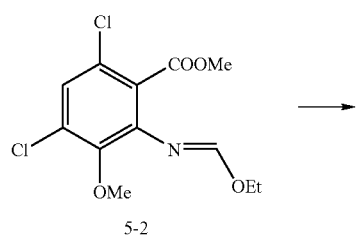

5-2

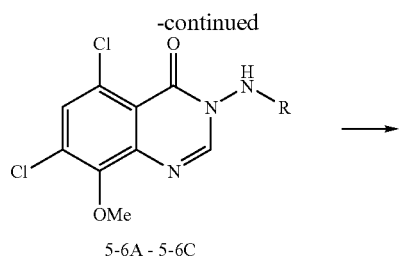

5-6A - 5-6C

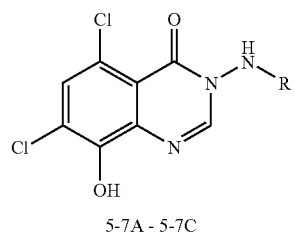

5-7A - 5-7C

To an ice-cooled suspension of the substituted-phenylhydrazine hydrochloride (1.61 mmol) in ethanol (4 mL) was added, under an argon atmosphere, triethylamine (185 mg, 1.83 mmol). The mixture was stirred at 0° C. for 15 min prior to the addition of a solution of the imidate 5-2 (180 mg, 0.59 mmol) in ethanol (3 mL). The resulting mixture was stirred at 0° C. for 40 min, then at room temperature for 4 days. The suspension was filtered and the white solid washed with cold ethanol and dried in vacuo to afford the 8-methoxy-3-(substituted)amino compound 5-6.

Examples of hydrazines used: 2,4-difluorophenylhydrazine hydrochloride gives 5-6A, 4-methoxyphenylhydrazine hydrochloride gives 5-6B, and 4-fluorophenylhydrazine hydrochloride gives 5-6C.

A solution of the 8-methoxy compound (5-6A, 5-6B or 5-6C) (0.133 mmol) and 48% aqueous hydrobromic acid (3 mL) was heated at 120° C. for 6 h, and allowed to cool to room temperature. The solid was isolated via filtration, washed with dichloromethane and diethyl ether and dried in vacuo to provide the 3-(substituted)amino compound (5-7A, 5-7B or 5-7C) (Table 8).

TABLE 8

Compounds prepared according to Example 5

| Compound | Structure | Yield (%) | $^1$H NMR data[#] | Mass spectral data |
|---|---|---|---|---|
| 5-6A | (structure shown) | 32 | (DMSO-$d_6$): δ 9.16 (s, 1 H), 8.62 (s, 1 H), 7.80 (s, 1 H), 7.29 (td, J = 2.4 and 9.2, 1 H), 6.89 (m, 2 H), 3.99 (s, 3 H) | m/z 372, 374, 376 (M$^+$ + 1, 100%, 66%, 11%) |

TABLE 8-continued

Compounds prepared according to Example 5

| Compound | Structure | Yield (%) | $^1$H NMR data[#] | Mass spectral data |
|---|---|---|---|---|
| 5-6B | 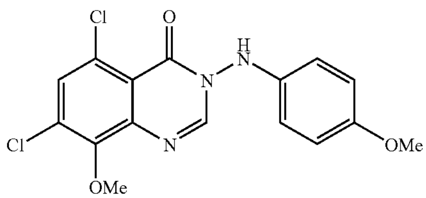 | | | |
| 5-6C | 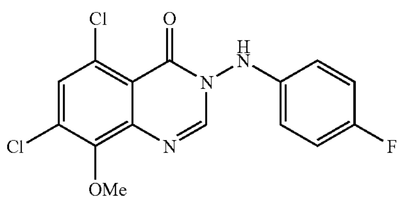 | | | |
| 5-7A (1100) | 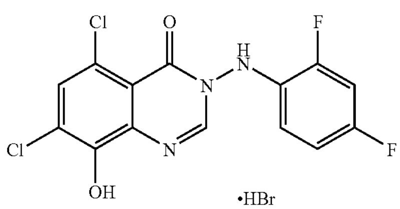 | 23 | (DMSO-d$_6$): δ 9.15 (s, 1 H), 8.60 (s, 1 H), 7.66 (s, 1 H), 7.29 (m, 1 H), 6.81 (m, 2 H). | m/z 356, 358, 360 (M$^+$ − 1, 100%, 66%, 11%) |
| 5-7B | 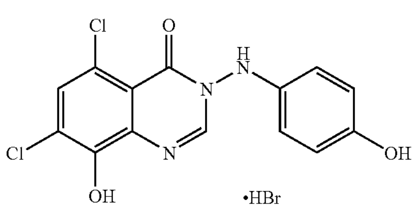 | | | |
| 5-7C | 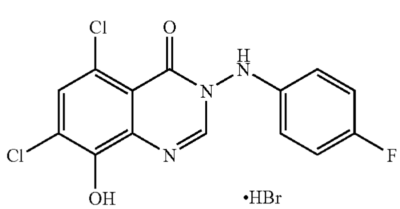 | | | |

[#]the chemical shifts for the 8-OH and HBr (where applicable) have not been included in the assignments

TABLE 9

Compounds prepared according to processes described in Scheme 5

| Compound | Structure |
|---|---|
| 5-7D | 5,7-dichloro-8-hydroxy-3-((cyclopropylmethyl)amino)quinazolin-4(3H)-one |
| 5-7E | 5,7-dichloro-8-hydroxy-3-(isobutylamino)quinazolin-4(3H)-one |
| 5-7F | 5,7-dichloro-8-hydroxy-3-(propylamino)quinazolin-4(3H)-one |
| 5-7G | 5,7-dichloro-8-hydroxy-3-(butylamino)quinazolin-4(3H)-one |
| 5-7H | 5,7-dichloro-8-hydroxy-3-(ethylamino)quinazolin-4(3H)-one |
| 5-7I | 5,7-dichloro-8-hydroxy-3-(isopropylamino)quinazolin-4(3H)-one |
| 5-5A | N-(5,7-dichloro-8-hydroxy-4-oxoquinazolin-3(4H)-yl)butyramide |
| 5-5B | N-(5,7-dichloro-8-hydroxy-4-oxoquinazolin-3(4H)-yl)-4-fluorobenzamide |
| 5-5C | N-(5,7-dichloro-8-hydroxy-4-oxoquinazolin-3(4H)-yl)-4-hydroxybenzamide |

TABLE 10

Compounds prepared via alkylation or acylation of some of the compounds from Tables 1 and 2

| Compound | Structure | Precursor |
|---|---|---|
| 6-1 | 5,7-dichloro-8-hydroxy-3-(2-(4-propylpiperazin-1-yl)ethyl)quinazolin-4(3H)-one | 2-7S2 |

TABLE 10-continued

Compounds prepared via alkylation or acylation
of some of the compounds from Tables 1 and 2

| Compound | Structure | Precursor |
|---|---|---|
| 6-2 | 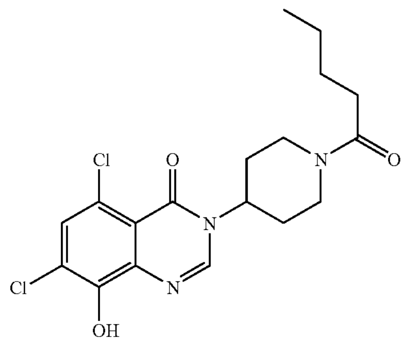 | 2-7X2 |
| 6-3 | 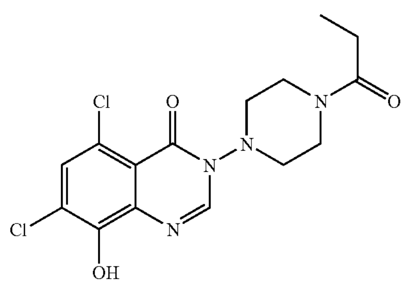 | 2-7R2 |
| 6-4 | 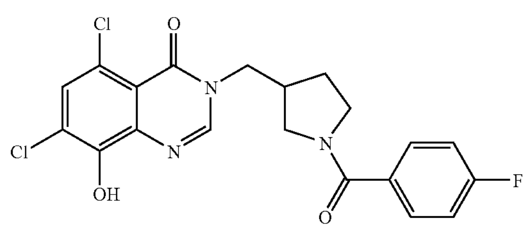 | 2-7Q2 |
| 6-5 | 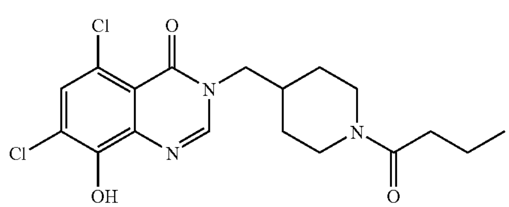 | 2-7I1 |
| 6-6 | 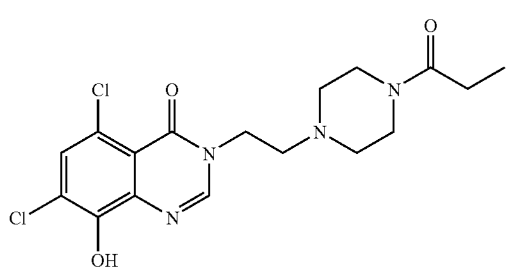 | 2-7S2 |

Example 6

Preparation of 3-substituted-3H-quinazolin-4-thione (7-2)

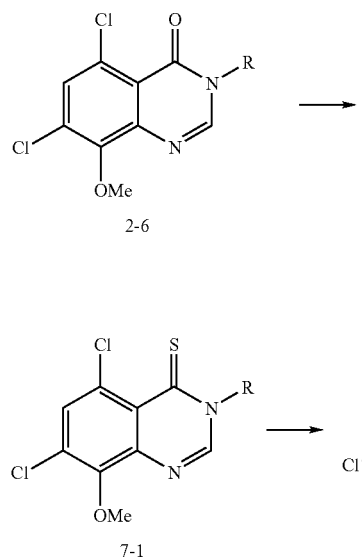

A mixture of the 3-substituted-3H-quinazolin-4-one (0.70 mmol), $P_4S_{10}$ (0.93 mmol) and pyridine (5 mL) was heated under reflux. When the reaction was complete, as monitored by TLC analysis, the mixture was concentrated to dryness and the resulting residue gave, after column chromatography ($SiO_2$; eluting with ethyl acetate/methanol, 100:1), the corresponding 3H-quinazolin-4-thione 7-1.

A mixture of the 3H-quinazolin-4-thione 7-1 was treated with $BBr_3$ according to conditions previously described in Example 1. Workup in the usual manner with methanol provided the corresponding 3H-quinazolin-4-thione 7-2 (Table 11).

TABLE 11

Compounds prepared according to Example 6

| Compound | Structure |
|---|---|
| 7-2A | 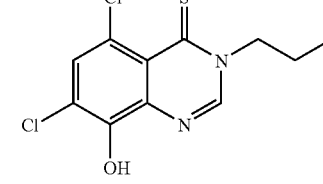 |
| 7-2B | 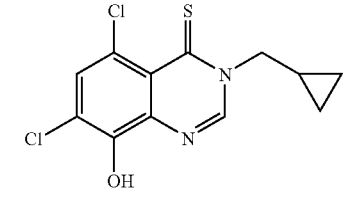 |
| 7-2C | 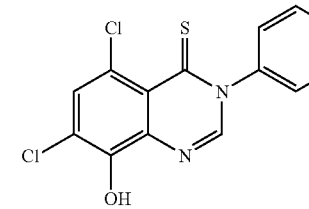 |
| 7-2D | 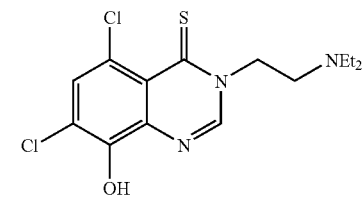 |
| 7-2E | 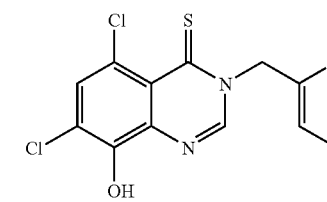 |
| 7-2F | 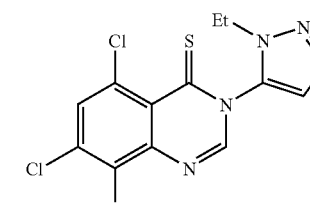 |
| 7-2G | 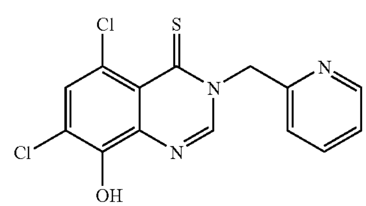 |
| 7-2H | 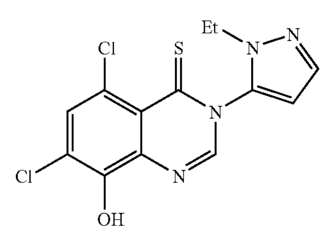 |

Example 7

Assessment of Compounds of Formula I

The following Assays were used in the assessment of the compounds of formula I for suitability for use in the methods of the invention.

Assay 1. Fluorometric $H_2O_2$ Assay

A fluorometric assay was used to test the ability of a test compound to inhibit hydrogen peroxide generation by Aβ in the presence of copper based on dichlorofluoroscein diacetate (DCF; Molecular Probes, Eugene Oreg.). The DCF solution (5 mM) in 100% dimethyl sulphoxide (previously purged with argon for 1 hr at 20° C.) was deacetylated in the presence of 0.025M NaOH for 30 min and neutralised at pH 7.4 to a final concentration of 1 mM. Horseradish peroxidase (HRP) stock solution was prepared to 1 µM at pH 7.4. The reactions were carried out in PBS, pH 7.4 in a 96 well plate (total volume=250 µl/well). The reaction solutions contained Aβ 1-42 at concentrations in the range of 50 nM to 1 µM, copper-glycine chelate (Cu-Gly), was prepared by adding $CuCl_2$ to glycine in the ratio of 1:6 and added to the Aβ in the proportion 2Cu-Gly:1Aβ), reducing agents including dopamine (5 µM) or ascorbic acid, deacetylated DCF 100 µM, and HRP, 0.1 µM. 1-10 µM EDTA or another chelator may also be present as a control for free copper, but was not required for the assay to function. The reaction mixture was incubated at 37 C for 60 min. Catalase (4000 units/ml) and $H_2O_2$ (1-2.5 µM) standards in PBS pH 7.4 may be included as positive controls. Fluorescence was recorded using a plate reader with excitation and emission filters at 485 nM and 530 nM respectively. $H_2O_2$ concentration may be established by comparing fluorescence with the $H_2O_2$ standards. Inhibition of Aβ $H_2O_2$ production was assayed by including a given concentration of test compound(s) in the test wells.

Assay 2. Neurotoxicity Assays
Primary Cortical Neuronal Cultures

Cortical cultures were prepared as previously described (White et al., 1998). Embryonic day 14 BL6Jx129sv mouse cortices were removed, dissected free of meninges and dissociated in 0.025% (wt/vol) trypsin. Dissociated cells were plated in 48 well culture plates at a density of $2\times10^6$ cells/mL in MEM with 25% (vol/vol) FCS and 5% (vol/vol) HS and incubated at 37° C., 2 hrs. Media was then replaced with Neurobasal media (Invitrogen Life Technologies) and B27 supplements (Invitrogen Life Technologies). Cultures were maintained at 37° C. in 5% $CO_2$. Prior to experimentation, the culture medium was replaced with Neurobasal media and B27 minus antioxidants (Invitrogen Life Technologies).

Primary Cerebellar Granule Neuronal Cultures

Cerebella from post-natal day 5-6 (P5-6) mice were removed and dissected free of meninges and dissociated in 0.025% trypsin. Cerebellar granule neurons (CGN) were plated in 24 well culture plates at 350 000 cells/$cm^2$ in BME (Invitrogen Life Technologies) supplemented with 10% Fetal Calf Serum (FCS), 2 mM glutamine and 25 mM KCl. Gentamycin sulphate (100 µg/mL) was added to all plating media and cultures were maintained at 37° C. in 5% $CO_2$.

Assay 3. Assays for Cell Viability
(a) MTS Assay for Cell Viability

Cell viability is determined using the MTS assay. Culture medium is replaced with fresh neurobasal medium plus B27 supplements minus antioxidants. 1/10 volume MTS solution (Cell Titre 96 Aqueous One, Promega Corporation) and incubated at 37° C., 2 hrs. 200 microlitre aliquots are measured with a spectrophotometer at 560 nm.

(b) LDH Assay for Cell Viability

Cell death is determined from culture supernatants free of serum and cell debris using the lactate dehydrogenase (LDH) Cytotoxicity Detection Kit (Boehringer Ingelheim) according to the manufacturer's instructions.

(c) Assay for Aβ Neurotoxicity and Aβ Neuroprotection

Neuronal cortical cells were cultured for five days as per Assay 2. On day six the neurobasal (NB) media (Invitrogen Life Technologies) and B27 supplement (Invitrogen Life Technologies) were replaced with NB media and B27 supplement (no antioxidants). On day six, test compounds were individually added to the neuronal cell cultures:

The test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 25 uM, 2.5 uM.

Aβ Preparation:

Aβ was initially dissolved in 20 mM NaOH to a concentration of 1 mM and sonicated for 5 minutes. The peptide was then diluted in $H_2O$ and 10×PBS to a final concentration of 200 uM Aβ in 1× PBS. The peptide was again sonicated for 5 minutes and then spun at 14000 rpm for 5 min and transferred to a fresh tube.

The test compounds were dissolved in 100% DMSO to a concentration of 2.5 mM (10 mM if excess compound was weighed out per vial—then diluted to 2.5 mM). 2.5 mM stock solution was serially diluted 1 in 10 [in NB media and B27 (no antioxidants)] to give working solutions of 250 uM, 25 uM, 2.5 uM. Test compounds were not added directly to cells, instead they were added to a 48 well 'Drug Plate' as comprised below:

Preparation of "Drug Plate":
To a 48 well plate add:
Well 1: 515 ul NB+B27 (no antioxidant)*+24 ul 25 uM test compound+60 ul Aβ diluent**
Well 2: 515 ul NB+B27 (no antioxidant)+24 ul 250 uM test compound+60 ul Aβ diluent
Well 3: 515 ul NB+B27 (no antioxidant)+24 ul test compound diluent***+60 ul Aβ1-42
Well 4: 515 ul NB+B27 (no antioxidant)+24 ul 2.5 uM test compound+60 ul Aβ1-42
Well 5: 515 ul NB+B27 (no antioxidant)+24 ul 25 uM test compound+60 ul Aβ1-42
Well 6: 515 ul NB+B27 (no antioxidant)+24 ul 250 uM test compound+60 ul Aβ1-42 diluent
Well 7: 515 ul NB+B27 (no antioxidant)+24 ul test compound diluent+60 ul Aβ1-42 diluent
Well 8: 600 ul NB+B27 (no antioxidant)

N.B. 60 ul Aβ1-42 equals 20 ul Aβ1-42 per well equals 20 uM Aβ1-42

The Drug Plate was incubated at 37° C. for 15 mins. 200 ul of each well was added in triplicate to the corresponding cell plate. The cell plate was incubated at 37 C, for 4 days.

* NB media+B27 (no antioxidants)
** Aβ diluent 2 mM NaOH, 1×PBS
*** PBT diluent 10% DMSO in NB+B27 (no antioxidant)

Completion of the Assay:

On the $4^{th}$ day after treating the cells the assay is completed by adding MTS to the cells.

(d) Assay for Test Compound Cytoxicity

Neuronal cortical cells were cultured for five days as per Assay 2 in NB media and B27 supplement.

On day six the test compounds were added to the neuronal cell cultures in NB media and B27 supplement minus antioxidants.

Test compounds were dissolved in 100% DMSO to a concentration of 2.5 mM (10 mM if excess compound was weighed out per vial—then diluted to 2.5 mM). 2.5 mM stock solution was serially diluted 1 in 10 to give working solutions of 250 uM, 25 uM, 2.5 uM. Test compounds were not added directly to cells, instead they were added to a 48 well 'Drug Plate' as comprised below:

Preparation of "Drug Plate":
To a 48 well plate add:
Well 1: 576 ul NB+B27 (no antioxidant)*+24 ul 2.5 uM test compound
Well 2: 576 ul NB+B27 (no antioxidant)+24 ul 25 uM test compound
Well 3: 576 ul NB+B27 (no antioxidant)+24 ul 250 uM test compound
Well 4: 576 ul NB+B27 (no antioxidant)+24 ul 2.5 uM test compound
Well 5: 576 ul NB+B27 (no antioxidant)+24 ul 25 uM test compound
Well 6: 576 ul NB+B27 (no antioxidant)+24 ul 250 uM test compound
Well 7: 576 ul NB+B27 (no antioxidant)+24 ul test compound diluent**
Well 8: 600 ul NB+B27 (no antioxidant)

The Drug Plate was incubated at 37° C. for 15 mins. 200 ul of each well was added in triplicate to the corresponding cell plate. The cell plate was incubated at 37° C., for 4 days, (2 compounds are tested on each plate of cells).
* NB media and B27 (no antioxidants),
** PBT diluent 10% DMSO in NB+B27 (no antioxidants)

On completion of the assay, 1/10 volume MTS was added per well of plate (ie 25 ul/250 ul). The plates were incubated at 37° C. for 2 hrs, and then absorbance was read at 560 nm.

Assay 4. Caspase Assay

To measure caspase activity in neuronal cultures, growth medium is removed, cells are washed twice with control salt solution (pH 7.4) and ice-cold cell extraction buffer is added directly to the cultures. The extraction buffer consists of 20 mM Tris (pH 7.4), 1 mM sucrose, 0.25 mM EDTA, 1 mM dithiothreitol (DTT), 0.5 mM PMSF, 1% Triton X-100 (Tx-100) and 1 μg/mL of pepstatin and aprotinin. After incubation for 15 min on ice, the extraction buffer is removed, centrifuged for 5 min at 4° C. in a microcentrifuge and 100 μL of supernatant is added to each well of a 96 well plate. 100 μL of 200 μM substrate (either DEVD-pNA, VEID-pNA or IETD-pNA for caspases 3, 6 and 8 respectively) is added to each well to give a final concentration of 100 μM substrate. Plates are incubated at 37° C. for 2, 4, 6 or 24 hr and the absorbance is determined at a wavelength of 415 nm (Abs415). The absorbance reading is compared to a known standard of pNA alone.

Assay 5. Annexin V Assay

To determine the level of annexin V binding to cells, cultures are washed twice with control salt solution (pH 7.4) followed by the addition of annexin V-FITC at a concentration of approximately 0.5 μg/mL in control salt solution (pH 7.4). Propidium iodide (10 pg/mL) is also added to the cultures at the same time. Cells are incubated in the dark for 30 min at ambient temperature and subsequently washed three times with fresh control salt solution. Analysis of FITC fluorescence (ex. 488 nm, em. 510 nm) is determined using a Leica DMIRB microscope. Photographs are taken with a Leica MPS 60 camera attachment using ASA400 colour film, and negatives are scanned into Adobe Photoshop v2.0.1.

Assay 6. Lipoprotein Oxidation Assay

Two different assays of metal-mediated lipid peroxidation can be utilized. The first assay involves measuring the oxidative activity of metallated proteins. This is determined by mixing dialyzed metallated or native protein (at designated concentrations) with 0.5 mg/mL LDL for 24 hr (37° C.). Lipid peroxidation (LPO) is measured using a lipid peroxidation assay kit (LPO 486, Oxis International Inc. Portland, Oreg.) as per kit instructions. The level of LPO is determined by comparing absorbance (486 nm) with LDL alone (100% LPO). The second assay is used to measure the LPO activity of native proteins in the presence of free, non-protein-bound Cu. This involves adding non-metallated peptides (140 μM) to 0.5 mg/mL LDL together with 20 μM Cu-gly and assaying for LPO as for the metallated proteins. The level of LPO is determined by comparing the absorbance (486 nm) with LDL+Cu-gly (100% LPO). As a negative control, LDL is also exposed to dialysed Cu-gly solutions comparable to those used to Cu-metallate the proteins.

Assay 7. Cytotoxicity Induced by Cu-Metallated Proteins

Proteins or synthetic peptides are mixed with metal-glycine solutions at equimolar or two-fold metal to protein concentration. Metal-protein mixtures are incubated overnight at 37° C. and then extensively dialysed (24 hr against two changes of $dH_2O$ (3 L/change) at room temperature) using mini-dialysis cups with a 3,500 kilodalton cut-off (Pierce, Rockford, Ill.). Dialysis of proteins against PBS pH 7.4 resulted in metallated proteins with identical activity to $dH_2O$ dialysis.

To determine their neurotoxic effects, metallated proteins, native proteins or peptides are added to two day-old primary cortical neuronal cultures. The cultures are also exposed to Cu-gly (5 or 10 μM) or LDL. Positive control cultures are treated with Cu-gly+LDL or the LPO product, 4-hydroxynonenol (HNE, Sigma Chemicals). Cultures are assayed for cell death using the lactate dehydrogenase (LDH) assay kit (Roche Molecular Biochemicals, Nunawading, Australia) according to the manufacturer's instructions.

Assay 8. Acridine Orange Assay for Aβ-Mediated Loss of Lysosomal Acidification

Cultured mouse cortical neurons are treated with Aβ1-42 (20 μM) for 16 h and then stained with 5 mg/ml acridine orange (AO) for 5 min at 37° C. 15 min at 37° C. The AO-induced fluorescence is measured with a red filter on a fluorescence microscope. AO is a lysosomotropic weak base which accumulates in the endosomal/lysosomal compartments and displays orange fluorescence during incubation. AO is sequestered inside the lysosomes as long as there is a substantial proton gradient over the lysosomal membranes. Treatment of cells with Aβ1-42 disrupts the lysosomal membrane proton gradient and relocalises AO into the cytosol, as indicated by the loss of orange fluorescence within 16-24 hr.

Assay 9. Human Brain Amyloid Solubilisation Assay

This assay was performed in order to assess the ability of a test compound to mobilise Aβ from the insoluble to the soluble phase of an extract of tissue from post mortem human AD brain.

Up to 0.5 g of plaque-bearing cortex without meninges was homogenized using a DIAX 900 homogenizer (Heudolph and Co, Kelheim, Germany) or other suitable device for three 30-second periods at full speed in up to 2 ml of ice-cold phosphate-buffered saline, pH 7.4. To obtain the phosphate-buffered saline-extractable fraction, the homogenate was centrifuged at 100,000×g for 30 min and the supernatant removed. Alternatively, the tissue was freeze dried then pulverised to form a powder which was then weighed out into aliquots for extraction as above. A 10 μl aliquot of supernatant was removed after centrifugation and mixed with an equal volume of 2×Tris-Ticene SDS sample buffer, pH 8.3, containing 8% SDS, 10% 2-mercaptoethanol. Samples were then heated for 10 mins at 90° C. and separated by gel electrophoresis. The insoluble fraction of the cortical samples was obtained by resuspending the initial pelleted sample in 1 ml of phosphate-buffered saline. A 50-μl aliquot of this suspension was then boiled in 200 ml of sample buffer as above.

Tris-Tricine polyacrylamide gel electrophoresis was performed by loading appropriately diluted samples on to 10% to 20% gradient gels (Novex, San Diego, Calif.) followed by transfer on to 0.2-μm nitrocellulose membrane (Bio-Rad, Hercules, Calif.). Aβ was detected by using monoclonal antibody W02, which detects residues 5 through 8, 17 (or another suitable antibody) in conjunction with horseradish peroxidase-conjugated rabbit anti-mouse IgG (Dako, Denmark), and visualized by using enhanced chemiluminescence (eg ECL; Amersham Life Science, Buckinghamshire, UK). Each gel included three lanes containing 0.5, 1, and 2 ng of synthetic Aβ$_{40}$ (Keck Laboratory, Yale University, New Haven, Conn.) as reference standards.

Blot membranes were read using a suitable imager eg. Fuji LAS3000 and densitometry performed using suitable software, eg Multigauge. The linear range of signal intensity for densitometric analysis of the mono- and dimeric Aβ bands was established relative t known Aβ standards. The percentages calculated in Table 13 represent the average readings from the treatment mouse group relative to the vehicle treated mouse group.

All samples were analysed several times, and gel loadings and dilutions were adjusted to fit within the quantifiable region of the standard curve. The insoluble Aβ being comprised of the pelletable fraction derived from the insoluble amyloid plaque from the above cortical samples and the soluble fraction comprising monomeric and/or oligomeric soluble Aβ.

Several gels were run per test compound with a PBS control included on each gel. Each gel containing varying concentrations of the test compound. A student's 't test' was used to compare the mean of the highest value obtained by the test compound for each gel at any concentration, to the mean of the PBS values taken from the multiple gels. Accordingly a determination can be made of whether the average increase in solubilisation obtained by any test compound is significant compared with PBS alone. Test compounds with a (+) score are compounds which achieved a statistically significant increase in plaque solubilisation over that of PBS alone. A test compound with a (−) score is a compound which does not achieve a statistically significant increase in plaque solubilisation over that of PBS alone.

Assay 10. Metal Partitioning

To assay effects upon the partitioning of various metals, including zinc and copper, following extraction of brain tissue in the presence of a test compound, soluble and insoluble fractions from an extract of human brain tissue are prepared as for the amyloid solubilisation assay. Metals in the two fractions are analysed by inductively-coupled plasma mass spectrometry, following appropriate pretreatment with nitric acid and/or hydrogen peroxide where necessary.

Assay 11. Effect of Administration of Test Compounds on Aβ Deposits in Transgenic Animals Transgenic mouse models are available for a number of neurological disorders, including Alzheimer's disease (Games et al., 1995; Hsiao et al., 1996); Parkinson's disease (Masliah et al., 2000); familial amyotrophic lateral sclerosis (ALS) (Gurney et al., 1994); Huntington's disease (Reddy et al., 1998); and Creutzfeld-Jakob disease (CJD) (Telling et al., 1994). We have found that one of the transgenic models for Alzheimer's disease, the APP2576 transgenic mouse (Hsiao et al., 1996) also has a high incidence of cataract. These animal models are suitable for testing the methods of the invention.

Transgenic mice of the strain APP2576 (Hsiao et al 1996) are used. Eight to nine month old female mice are selected and divided into groups for treatment.

Mice are sacrificed at intervals, and their brains examined to determine whether the treatment with test compounds decreased brain amyloid formation, and the identification of the most effective administration protocol. The levels of soluble and insoluble Aβ in the brain and serum are determined using calibrated Western blots as per the methodology described for Assay 9. Brain Amyloid Solubilisation Assay.

Other mice in each group are tested over a period of up to eight months for cognitive performance, using a Morris water maze according to standard methods. The general health and well-being of the animals is also measured every day by a blinded operator, using a five point integer scale which subjectively rates a combination of features, including motor activity, alertness and general health signs.

Assay 12. Physiochemical Properties
Polar Surface Area Calculations (PSA)

Polar surface area values were calculated using the web-based program available through "Molinspiration", a package for calculation of molecular properties.

Turbidimetric Solubility Measurements

The solubility estimate was measured at both pH 2.0 and pH 6.5. This is within the pH range that can be anticipated along the proximal gastrointestinal tract in humans.

The compounds were dissolved in DMSO to appropriate concentrations and then spiked into either 0.01M HCl (approx. pH=2.0) or pH 6.5 isotonic phosphate buffer, the final DMSO concentration being 1%. Samples were then analysed via Nephelometry to determine a solubility range. [as per D. Bevan and R. S. Lloyd, Anal. Chem. 2000, 72, 1781-1787].

cLog P Values

Theoretical Log P values were determined using the ACD Log P software. The values quoted have been calculated from an untrained database and refer to the unionised species.

Assay 13. Blood Brain Barrier Penetration

The test compounds were dissolved in DMSO and phosphate buffered saline (PBS) was added to obtain solutions at a concentration of 50 μM in PBS containing 1.25-2.5% DMSO. A trace amount of $^{14}$C-sucrose was added to each stock infusion solution (approx 0.01 μCi/mL) to act as Blood-Brain Barrier (BBB)-impermeable marker in order to assess the integrity of the BBB during each perfusion and to estimate the volume of the residual vascular space (RVS) in samples of brain tissue (ie: the volume of fluid remaining inside the lumen of blood vessels at the end of each perfusion).

Adult male Spague Dawley rats (180-190 g) were anaesthetized with intraperitoneal injections of Urethane (25% w/v) at a dose of 1.0 mL/100 g body weight. The right common carotid artery was surgically exposed and cannulated for perfusion of the cerebral circulation. The right external carotid artery (which supplies tissues outside the skull) was then ligated distal to its bifurcation from the right common carotid artery so that all of the infusion solution would pass into the brain via the remaining right internal carotid artery. The heart was then exposed and transected immediately prior to the commencement of the infusion. The rate of the infusion was controlled by a pump set to deliver at 3.2 mL/min (approx. 85% of the normal blood supply to the brain for this size of rat). The infusion cannula initially contained a 0.5 mL pre-wash of heparinised PBS (10 IU/ml) that acts to flush blood vessels and to prevent blood from clotting and blocking small vessels.

After 1.5 minutes, the infusion pump automatically stopped, the cannula was withdrawn from the carotid artery and a sample of the infusion solution (1-1.5 mL) was then collected from the tip of the infusion cannula. The brain was then dissected free and divided into 3 parts; the right hemisphere together with the right midbrain, the left hemisphere together with the left midbrain and the hindbrain (cerebellum, pons and brainstem). Only the right part of the brain was used for subsequent measurements because perfusion via the right internal carotid artery preferentially supplies the right hemisphere and right midbrain (the left hemisphere and hindbrain receive a variable collateral perfusion). The brain tissue samples from each animal were frozen at −30° C., homogenized and weighed aliquots analysed by LC-MS to give total brain concentration. The analysis was carried out using the Micromass Triple Quad instrument. The mobile phase consisted of an acetonitrile/water gradient (containing 0.05% Formic acid) and the column was a Phenomenex Luna CN.

Small aliquots from each brain tissue sample and the corresponding infusion solution were analysed by liquid scintillation counting to determine the level of $^{14}C$-sucrose. The residual vascular space (RVS) in each brain tissue sample was calculated by dividing the measured concentration of sucrose in brain tissue (dpm/mg) by its concentration in the corresponding infusion solution (dpm/μL). This is the volume of fluid that remains inside blood vessels at the end of each perfusion. Multiplying this RVS by the concentration of the test compound in the infusion solution gives the total residual amount of the test compound that is present inside blood vessels in each brain tissue sample (ie: that which has not crossed the BBB). Subtracting this from the total brain concentration gives the amount of drug in each brain tissue sample that is outside the blood vessels (ie: which has crossed the BBB). Dividing this RVS-corrected brain concentration gives the brain uptake ratio (Equation. 1).

$$\text{Brain Uptake Ratio} = \frac{[\text{brain } ng \cdot mg^{-1}] - [RVS\ ng \cdot \mu l^{-1}]}{[\text{infusion solution } ng \cdot \mu L^{-1}]} \quad \text{Equation 1}$$

A total of 5-6 brain perfusion experiments were performed for each of the test compounds and mean brain uptake ratios were calculated.

Ratios of greater than 50% indicate compounds that enter the brain extremely rapidly; ratios between 10 and 50% indicate compounds that enter the brain well; ratios less than 10% (not observed) would indicate compounds that enter the brain very slowly and would not be suitable for therapeutic administration; ratios less than 1% (not observed) would indicate compounds that are effectively excluded from the brain.

Assay 14. Transgenic Mouse Brain Immunohistochemistry

The APP2576 transgenic mouse (Hsiao et al., 1996) as referred to in Assay 11 is utilized in this assay. The contralateral formalin-fixed mouse brain tissue is coronally cut. Sections (10 μm) are taken from the corresponding sites and treated with 80% formic acid for antigen retrieval. The primary antibody used is monoclonal antibody 1E8, which recognizes epitopes between residues 18 and 22 of Aβ (SmithKline Beecham, UK). Immunoreactivity is developed with secondary antibody linked to horseradish peroxidase (using a 3,39-diaminobenzidinechromagen) (Dako) and alkaline phosphatase (using 5-bromo-4-chloro 3-indoxyl phosphate and nitroblue tetrazolium chloride chromagen) (Dako). Plaque abundance per section is assessed by two operators blinded to treatment according to the following scale:

0=no plaques apparent

1=plaques present but very sparse

2=several plaques present

3=numerous plaques visible in restricted areas

4=plaques abundant and not restricted to any particular area.

Intermediate values eg 2.5 are assigned where applicable. Students 't' test is used for comparisons between groups.

Assay 15. Pharmacokinetic Profile

Intravenous infusion of test compound; 2 mg/Kg in a suitable vehicle is administered to 2 rats and arterial blood is sampled up to 24 hours.

Oral administration of test compound; 30 mg/Kg in a suitable vehicle is administered via oral gavage to 2 rats and arterial blood is sampled up to 24 hours.

Plasma concentrations of test compound are determined by suitable analytical method.

Calculations:

$$CL_{total} = \frac{Dose_{IV}}{AUC_{IV}}$$

$$V_{d\beta} = \frac{CL_{total}}{\beta}$$

$$BA(\%) = \frac{AUC_{oral} * Dose_{IV}}{AUC_{IV} * Dose_{oral}}$$

| | |
|---|---|
| $CL_{total}$ = | total plasma clearance after IV administration |
| $V_{d\beta}$ = | volume of distribution during the elimination phase after IV administration |
| BA = | oral bioavailability |
| $AUC_{IV}$ = | area under the plasma concentration versus time profile from time zero to infinity after IV administration |
| $AUC_{oral}$ = | area under the plasma concentration versus time profile from time zero to infinity after oral administration |
| β = | terminal elimination rate constant after IV administration |

Assay 16. Determination of Mouse Plasma Levels of Test Compounds

PB 1075

Oral administration of PB 1075 at 30 mg/kg, as a suspension in Na-Carboxymethyl Cellulose (CMC) was administered by oral gavage to four mice. Two mice were sacrificed 30 minutes after administration and two mice were sacrificed 60 minutes after administration. Blood was obtained by cardiac puncture and plasma separated by centrifugation.

The concentration of PB 1075 was determined by LC/MS using the triple quadrupole instrument. The mobile phase consisted of an acetonitrile (ACN)/water gradient (containing 0.05% Formic acid) and the column was a Phenomenex Lunea 5 um C8 (50×2 mm) column.

The supplied acute toxicity mouse plasma samples were directly injected following a protein precipitation with ACN. The analytical method in plasma was linear in the range of 10 to 10,000 ng/ml ($R^2$=0.994). Recovery of PB 1075 from plasma was ~100%.

The concentrations of PB 1075 in the mouse plasma samples are given in Table 12.

TABLE 12

Concentrations of PB 1075 in Mouse Plasma after Oral Dosing at 30 mg/kg

| Exp. No. | Time (min) | Conc. (ng/ml) |
|---|---|---|
| 2459 | 30 | 431.26 |
| 2470 | 30 | 298.46 |
| 2495 | 60 | 424.81 |
| 2781 | 60 | 519.56 |

PB 1076

Oral administration of PB 1076 at 30 mg/kg, as a suspension in Na-Carboxymethyl Cellulose (CMC) was administered by oral gavage to four mice. Two mice were sacrificed 30 minutes after administration and two mice were sacrificed 60 minutes after administration. Blood was obtained by cardiac puncture and plasma separated by centrifugation.

The concentration of PB 1076 was determined by LC/MS using the triple quadrupole instrument. The mobile phase consisted of an acetonitrile (ACN)/water gradient (containing 0.05% Formic acid) and the column was a Phenomenex Luna 5 µM C8 (50×2 mm) column.

The mouse plasma samples were directly injected following a protein precipitation with ACN. The analytical method in plasma was linear in the range of 500 to 10,000 ng/ml ($R^2$=0.999). Recovery of PB 1076 from plasma was ~85%.

The concentration of PB 1076 in mouse plasma after dosing orally at 30 mg/kg is given in Table 13.

TABLE 13

Concentrations of PB 1076 in Mouse Plasma after Oral Dosing at 30 mg/kg

| Mouse ID | Time (min) | Conc. (ng/ml) |
|---|---|---|
| 3036 | 30 | 2325.77 |
| 3041 | 30 | 1593.61 |
| 3014 | 60 | 2697.62 |
| 3015 | 60 | 1167.52 |

PB 1077

Oral administration of PB 1077 at 30 mg/kg, as a suspension in Na-Carboxymethyl Cellulose (CMC) was administered by oral gavage to four mice. Two mice were sacrificed 30 minutes after administration and two mice were sacrificed 60 minutes after administration. Blood was obtained by cardiac puncture and plasma separated by centrifugation.

The concentration of PB 1077 was determined by LC/MS using the triple quadrupole instrument. The mobile phase consisted of an acetonitrile (ACN)/water gradient (containing 0.05% Formic acid) and the column was a Phenomenex Luna 5 µM C8 (50×2 mm) column.

The mouse plasma samples were directly injected following a protein precipitation with ACN. The analytical method in plasma was linear in the range of 5 to 5,000 ng/ml ($R^2$=0.999). Recovery of PB 1077 from plasma was ~92%.

The concentration of PB 1077 in mouse plasma after dosing orally at 30 mg/kg is given in Table 14.

TABLE 14

Concentrations of PB 1077 in Mouse Plasma after Oral Dosing at 30 mg/kg

| Mouse ID | Time (min) | Conc. (ng/ml) |
|---|---|---|
| 3062 | 30 | 731.2 |
| 3060 | 30 | 984.7 |
| 3093 | 60 | 752.8 |
| 3095 | 60 | 495.1 |

Assay 17. Synthetic Amyloid Plaque Disaggregation Assay

This assay measures the ability of test compounds to dissolve aggregates of synthetic Alzheimer's A-beta 42 residue peptide formed by precipitation with zinc.

The synthetic plaque disaggregation assay is a thioflavin T fluorescence-based assay which measures the ability of a test compound to disaggregate synthetic aggregates generated by the incubation of Alzheimer's amyloid A-beta protein (Aβ) in the presence of zinc.

The 42 residue A-beta which is the form most prevalent in Alzheimer's amyloid plaques is precipitated by the addition of zinc salts to form a beta sheet conformational aggregate physicochemically congruent with the crystalline amyloid plaque cores. Thioflavin T, an agent which exhibits specific fluorescence when it intercalates within a beta sheet structure, is incorporated into the A-beta/Zn aggregate during the aggregation process. Solubilisation of the metal bound aggregates by a test compound will result in reduced fluorescence as the beta sheet conformation is lost. The activity of a compound in this assay is a combination of its metal chelating properties, solubility, hydrophobicity and structural elements which influence interaction with the amyloid mass.

The assay models the process by which a test compound is acting, either to compete for bound metals with Aβ or alternatively to displace metals by competitively binding at the metal binding site, resulting in Aβ precipitated by zinc, being solubilised, as an in vitro model of plaque disaggregation.

Assay Reagents

Aliquots of synthetic Aβ peptide are prepared for convenience. Aβ is dissolved in distilled H2O and peptide concentration is assessed by absorption at 214 nm against a validated standard curve. Abeta/Zn aggregates in the presence of solvent only (DMSO) and control vehicle (PBS) are included in each assay as negative controls. The test compounds were dissolved in DMSO to a concentration of 5 mM. Dilutions were made in DMSO as appropriate to 100 times the desired final concentration and added immediately to the A-beta aggregates.

Method

A-beta 1-42 is incubated with ZnCl2 and Thioflavine T (ThT) in a molar ratio of (1:2:2) for 24 hours at 37 degrees on a rotating wheel in PBS pH 6.6. Following incubation, aggregates are incubated with test drug for a further 2 hours at 37 degrees with rotation. PBS blank, untreated aggregates and DMSO controls are included with each experiment. After 2 hour incubation, samples are measured for ThT fluorescence using an LS55 (Perkin Elmer) fluorimeter in a cuvette.

Data are generated in FL Winlab software (Perkin Elmer) and analysed using GraphPad Prism v4.0 software. Data are calculated as the average of multiple reads.

Results

Results are presented in tabular form as the concentration (uM) at which 50% disaggregation ($IC_{50}$) is obtained and as percent disaggregation at 5 uM (expressed as 5/% reduction). The two values together provide a measure of the efficiency of disaggregation.

If the compound does not achieve 50% disaggregation within the concentration range tested the result is recorded as >20 μM, corresponding to the maximum concentration at which the compound is tested. This result indicates that the test compound is relatively poor at being able to disaggregate the Aβ 1-42 aggregates. A test compound able to achieve an $IC_{50}$ at less than 20 μM and scoring greater than 20% disaggregation at 5 μM is considered 'good'. A test compound able to achieve an $IC_{50}$ at less than 20 μM and scoring greater than 40% disaggregation at 5 μM is considered 'very good'.

TABLE 15

| Assay | Assay 1 Peroxide $IC_{50}$ (μM) | Assay 3(d) Cytotoxicity (% viable at 1 and 10 uM) | Assay 3(c) Neuroprotection (% inhibition of Abeta toxicity) | Assay 12 ClogP | Assay 12 Polar surface area (PSA) | Assay 16 Mice plasma concentration | Assay 11 and Assay 14 Tg mice Soluble Fraction: % change compared with vehicle alone control mice. Insoluble Fraction: % change compared with vehicle alone control mice. Plaques score represents an average count score per treatment group relative to the average score of the vehicle (sham) treated group score ... | Assay 17 Disaggregation EC50 (μM) and percentage disaggregation at 5 uM |
|---|---|---|---|---|---|---|---|---|
| 1075 | 0.73 | 99, 87 | | 2.58 | 58.4 | Up to 520 ng/mL in mice | +9% (insol), −19% (sol), −22% (plaque) | |
| 1076 | 0.45 | 116, 105 | | 2.74 | 55.1 | Up to 2698 ng/mL in mice | −21% (insol) −24% (sol) −29% (plaque) | |
| 1077 | 0.48 | 101, 86 | | 2.03 | 68.0 | Up to 984 ng/mL in mice | Negligible effect on insol ... −17% (sol), −30% (plaque) | |
| 1078 | 0.73 | 94, 94 | | 2.87 | 58.4 | | Up to 262 ng/mL in mice. | |
| 1080 | 0.44 | 105, 70 | 15 | 1.84 | | | | |
| 1081 | 0.55 | | 7 | 2.41 | | | Up to 207 ng/mL | |
| 1082 | 4.5 | | 94, 70 | 1.76 | | | | |
| 1083 | 2.3 | | 105, 97 | 2.67 | | | | |
| 1084 | 0.36 | 100, 93 | 2 | 2.37 | | Upto 2439 ng/mL | −17% (insol), −29% (sol) −21% (plaque) | |
| 1085 | 0.37 | 99, 72 | 7 | 1.95 | | Upto 3644 ng/mL | | |
| 1086 | 0.39 | 98, 51 | | 2.94 | | | | |
| 1087 | 1.52 | 94, 58 | 11 | 2.53 | | | | |
| 1088 | 0.84 | 102, 94 | 3 | 1.94 | | | Upto 3896 ng/mL in mice | |
| 1089 | 0.78 | 96, 83 | 13 | 2.31 | | | | |
| 1091 | 0.46 | 100, 92 | −8 | 2.36 | | | | |
| 1092 | 0.86 | 95, 81 | | 1.81 | | | | |
| 1093 | 0.39 | 122, 13 | | 2.58 | | | | |
| 1094 | | 97, 96 | 1 | 1.99 | | | | |
| 1097 | 0.28 | 99, 78 | | 2.19 | | Upto 261 ng/mL in mice | −22% (sol) +1% (insol) −3% (plaque) | |
| 1098 | 0.44 | 99, 88 | | 2.48 | | Upto 439 ng/mL in mice | | |
| 1099 | 0.69 | 103, 101 | | 2.50 | | | | |
| 1100 | 0.42 | 100, 92 | | 3.13 | | | | 17 uM, 42 5/% |
| 1101 | <4.1 | 89, 17 | | 3.42 | | | | 11.7 uM, 45 5/% |
| 1107 | 0.4 | 92, 59 | | 3.22 | | Upto 1802 ng/mL in mice | | |
| 1108 | 0.25 | 100, 53 | | 2.6 | | Upto 383 ng/mL in mice | | |
| 1110 | 0.46 | 107, 77 | | 3.24 | | | | |
| 1111 | 0.32 | 93, 67 | | 3.35 | | | | |
| 1112 | 0.33 | 89, 46 | | 3.13 | | Upto 2949 ng/mL in mice | | |
| 1114 | 0.58 | 101, 73 | | | | | | |
| 1115 | 0.73 | 101, 73 | | | | | | |
| 1126 | 0.37 | | | 3.07 | | | | |
| 1128 | 0.34 | | | 2.55 | | | | 13.2 uM, 41 5/% |
| 1130 | 0.88 | | | 1.89 | | | | |
| 1131 | 0.5 | | | 2.42 | | | | |

TABLE 15-continued

| Assay | Assay 1 Peroxide IC$_{50}$ (μM) | Assay 3(d) Cytotoxicity (% viable at 1 and 10 uM) | Assay 3(c) Neuroprotection (% inhibition of Abeta toxicity) | Assay 12 ClogP | Assay 12 Polar surface area (PSA) | Assay 16 Mice plasma concentration | Assay 11 and Assay 14 Tg mice Soluble Fraction: % change compared with vehicle alone control mice. Insoluble Fraction: % change compared with vehicle alone control mice. Plaques score represents an average count score per treatment group relative to the average score of the vehicle (sham) treated group score ... | Assay 17 Disaggregation EC50 (μM) and percentage disaggregation at 5 uM |
|---|---|---|---|---|---|---|---|---|
| 1132 | 0.47 | | | 2.34 | | | | 15.2 uM, 16 5/% |
| 1133 | 0.79 | | | 1.63 | | | | |
| 1147 | 0.26 | | | 1.50 | | | | |
| 1161 | 0.14 | | | 1.13 | | | | |

References cited in the description and examples are listed on the following pages, and are incorporated herein by this reference.

REFERENCES

Ariga, T., Kobayashi, K., Hasegawa, A., Kiso, M., Ishida, H., and Miyatake, T. (2001) Characterization of high-affinity binding between gangliosides and amyloid β-protein. Arch. Biochem. Biophys. 388, 225-230.

Atwood et al., J. Biol. Chem., 1998, 273(21), 12817-12826.

Beyreuther K, Christen Y, Masters C L (eds) Neurodegenerative Disorders Loss of Function Through Gain of Function. Springer. Berlin. 2001. 189 pp.

Brower V. Harnessing the immune system to battle Alzheimer's: Some of the most promising approaches to fight Alzheimer's diseases aim to develop vaccines. EMBO Rep 2002; 3:207-9.

Bush A I, Masters C L. Clioquinol's return. Science 2001; 292:2251-2252.

Bush A I. Therapeutic targets in the biology of Alzheimer's disease. Current Opinion in Psychiatry 2001; 14:341-348.

Corder, E. H., Saunders, A. M., Strittmatter, W. J., Schmechel, D. E., Gaskell, P. C., Small, G. W., Haines, J. L., and Pericak-Vance, M. A. (1993) Gene dose of apolipoprotein E type 4 allele and the risk of Alzheimer's disease in the late onset familial disease. Science 261, 921-923.

Curtain, C. C., Ali, F., Volitakis, I., Chemy, R. A., Norton, R. S., Beyreuther, K., Barrow, C. J., Masters, C. L., Bush, A. I., and Barnham, K. J. (2001) Alzheimer's disease amyloid β binds copper and zinc to generate an allosterically ordered membrane-penetrating structure containing superoxide dismutase-like subunits. J. Biol. Chem. 276, 20466-20473.

Czech, C., Forstl, H., Hentschel, F., Monning, U., Besthorn, C., Geigerkabisch, C., Sattel, H., Masters, C., and Beyruether, K. (1994) Apolipoprotein E-4 gene dose in clinically diagnosed Alzheimer's disease: prevalence, plasma cholesterol levels and cerebrovascular change. Eur. Arch. Psychiatry Clin. Neurosci. 243, 291-292.

Fassbender, K., Simons, M., Bergmann, C., Stroick, M., Lutjohann, D., Keller. P., Runz, H., Kuhl, S., Bertsch, T., von Bergmann. K., Hennerici, M., Beyreuther, K., and Hartmann, T. (2001) Simvastatin strongly reduces levels of Alzheimer's disease β-amyloid peptides Aβ 42 and Aβ 40 in vitro and in vivo. Proc. Natl. Acad. Sci. USA. 98, 5856-5861.

Frears, E. R., Stephens, D. J., Walters, C. E., Davies, H., and Austen, B. M. (1999) The role of cholesterol in the biosynthesis of b-amyloid. NeuroReport 10, 1699-1705.

Friedhoff, L. T., Cullen, E. I., Geoghagen, N. S., and Buxbaum, J. D. (2001) Treatment with controlled-release lovastatin decreases serum concentrations of human β-amyloid (Aβ) peptide. Int. J. Neuropsychopharmacol. 4, 127-130.

Games D., Adams D., Alessandrini R., Barbour R., Berthelette P., Blackwell C., Carr T., Clemens J., Donaldson T., Gillespie F., Guido T., Hagopian S., Johnsonwood K., Khan K., Lee M., Leibowitz P., Lieberburg I., Little S., Masliah E., Mcconlogue L., Montoyazavala M., Mucke L., Paganini L., Penniman E., Power M., Schenk D., Seubert P., Snyder B., Soriano F., Tan H., Vitale J., Wadsworth S., Wolozin B., Zhao J., NATURE, 1995, 373 (6514): 523-527.

Gilgun-Sherki Y., Melamed E., Offen D., Neuropharmacology, 2001, 40 (8): 959-975.

Gurney M. E., Pu H. F., Chiu A. Y., Dalcanto M. C., Polchow C. Y., Alexander D. D., Caliendo J., Hentati A., Kwon Y. W., Deng H. X., Chen W. J., Zhai P., Sufit R. L., Siddique T., SCIENCE, 1994, 264 (5166): 1772-1775.

Hartmann, T. (2001) Cholesterol, Aβ and Alzheimer's disease. Trends Neurosci. 24,S45-S48.

Hertel, C., Terzi, E., Hauser, N., Jakob-Rotne, R., Seelig, J., and Kemp, J. A. (1997) Inhibition of the electrostatic interaction between β-amyloid peptide and membranes prevents β-amyloid-induced toxicity. Proc. Natl. Acad. Sci. USA. 94, 9412-9416.

Hsiao, K., Chapman, P., Nilsen, S., Eckman, C., Harigaya, Y., Younkin, S., Yang, F., Cole, G. (1996) Correlative memory deficits, Aβ elevation, and amyloid plaques in transgenic mice SCIENCE; 274(5284):99-102.

Huang X, Atwood C S, Hartshorn M A et al. The Aβ peptide of Alzheimer's disease directly produces hydrogen peroxide through metal ion reduction. Biochemistry 1999; 38:7609-7616.

Ji, S. R., Wu, Y., and Sui, S. F. (2002) Cholesterol is an important factor affecting the membrane insertion of β-amyloid peptide (Aβ 1-40), which may potentially inhibit the fibril formation. J. Biol. Chem. 277, 6273-6279.

Karbownik M., Lewinski A., Reiter R. J., Int. J. Biochemistry & Cell Biology, 2001, 33 (8): 735-753.

Lee J-Y, Cole T B, Palmiter R D, Suh S W, Koh J-Y. Contribution by synaptic zinc to the gender-disparate plaque formation in human Swedish mutant APP transgenic mice. Proc Natl Acad Sci USA 2002: Early edition.

Manfredini S, Pavan B, Vertuani S, Scaglianti M, Compagnone D, Biondi C, Scatturin A, Tanganelli S, Ferraro L, Prasad P, Dalpiaz A, JOURNAL OF MEDICINAL CHEMISTRY, 45 (3): 559-562 Jan. 31, 2002

Masliah E., Rockenstein E., Veinbergs I., Mallory M., Hashimoto M., Takeda A., Sagara Y., Sisk A., Mucke L., SCIENCE, 2000, 287 (5456): 1265-1269.

Nunan, J., and Small, D. H. (2000) Regulation of APP cleavage by α-, β- and δ-secretases. FEBS Lett. 483, 6-10.

Petersen, R. C, Stevenas, J. C., Ganguli, M., Tangalos, E. G., Cummings, J. L., and DeKosky, S. T. Practice parameter: Early detection of dementia: Mild cognitive impairment Neurology 2001 56 1133-1142.

Reddy P. H., Williams M., Charles V., Garrett L., Pike-Buchanan L., Whetsell W. O., Miller G., Tagle D. A., NATURE GENETICS, 1998, 20 (2): 198-202.

Rogers S L, Farlow M R, Doody R S, Mohs R, Friedhoff L T. A 24-week, double-blind, placebo-controlled trial of donepezil in patients with Alzheimer's disease. Donepezil Study Group. Neurology 1998; 50:136-45.

Rosen W G, Mohs R C, Davis K L. A new rating scale for Alzheimer's disease. Am J Psychiatry 1984; 141:1356-64.

Sakaeda T, Tada Y, Sugawara T, Ryu T, Hirose F, Yoshikawa T, Hirano K, Kupczyk-Subotkowska L, Siahaan T J, Audus K L, Stella V J, JOURNAL OF DRUG TARGETING, 9 (1): 23-37 2001.

Schenk, D., Barbour, R., Dunn, W., Gordon, G., Grajeda, H., Guido, T., Hu, K., Huang, J., Johnson-Wood, K., Khan, K., Kholodenko, D., Lee, M., Liao, Z., Lieburburg, I., Motter, R., Mutter, L., Soriano, F., Shopp, G., Vasquez, N., Vandervert, C., Walker, S., Wogulis, M., Yednock, T., Games, D., and Seubert, P. (1999) Immunization with amyloid-β attenuates Alzheimer's disease like pathology in the PDAPP mouse. Nature 400, 173-177.

Selkoe, D. J. Alzheimer's disease: genes, proteins and therapy. Physiol Rev 81 (2): 741-766.

Shearman M S, Beher D, Clarke E E et al. L-685,458, an aspartyl protease transition state mimic, is a potent inhibitor of amyloid β-protein precursor β-secretase activity. Biochemistry 2000; 29:8698-704.

Shiraki, H. The neuropathology of subacute myelo-optico-neuropathy (SMON) in the humans: With special reference to the quinoform intoxication. Jpn J Med Sci Biol 1975; 28 (suppl): 101-164.

Simons M, Schwarzler F, Lutjohann D et al. Treatment with simvastatin in normocholesterolemic patients with Alzheimer's disease: a 26-week randomised, placebo-controlled, double-blind trial. Ann of Neurol In Press.

Sinha S, Anderson J P, Barbour R et al. Purification and cloning of amyloid precursor protein β-secretase from human brain. Nature 1999; 402:537-40.

St George-Hyslop, P. H. (2000) Molecular genetics of Alzheimer's disease. *Biol. Psychiatry* 47, 183-199.

T. C. Wang, Y. L. Chen, K. H. Lee and C. C. Tzeng, *Tetrahedron Lett.*, 1996, 37, 6369-6370.

Telling G. C., Scott M., Hsiao K. K., Foster D., Yang S. L., Torchia M., Sidle K. C. L., Collinge J., Dearmond S. J., Prusiner S. B., PROCEEDINGS OF THE NATIONAL ACADEMY OF SCIENCES OF THE UNITED STATES OF AMERICA, 11 Oct. 1994, 91 (21): 9936-9940.

Valdez-Gonzalez, T., Inagawa, J., and Ido, T. (2001) Neuropeptides interact with glycolipid receptors: a surface plasmon resonance study. Peptides 22; 1099-1106.

White et al., J Neuroscience, (1998) 18, 6207-6217.

Wright, J. S. Johnson, E. R. and DiLabio, G. A. *J. Am. Chem. Soc* 2001 123 1173-1183.

Yassin M S, Ekblom J, Xilinas M, Gottfries C G, Oreland L. Changes in uptake of vitamin B(12) and trace metals in brains of mice treated with clioquinol. J Neurol Sci 2000; 173:40-44.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The claims defining the invention are as follows:

1. A compound of the formula

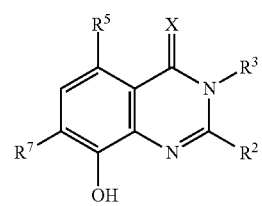

I or pharmaceutically acceptable salts, tautomers or stereoisomers thereof, in which
   $R^2$ is $CH_2NR^1R^4$ in which $R^1$ and $R^4$ are independently selected from H and $C_{1-3}$ alkyl;
   $R^3$ is optionally substituted $C_{1-4}$ alkyl;
   $R^5$ and $R^7$ are chloro; and
   X is O
   wherein the optional substituents are independently selected from alkyl, alkenyl, alkynyl, aryl, formyl, halo, haloalkyl, haloalkenyl, haloalkynyl, haloaryl, hydroxy, alkoxy, alkenyloxy, aryloxy, benzyloxy, haloalkoxy, haloalkenyloxy, haloaryloxy, nitro, nitroalkyl, nitroalkenyl, nitroalkynyl, nitroaryl, nitroheterocyclyl, amino, alkylamino, dialkylamino, alkenylamino, alkynylamino, arylamino, diarylamino, benzylamino, dibenzylamino, acyl, alkenylacyl, alkynylacyl, arylacyl, acylamino, diacylamino, acyloxy, alkylsulphonyloxy, arylsulphenyloxy, heterocyclyl, heterocyclyloxy, heterocyclylamino, haloheterocyclyl, alkylsulphenyl, arylsulphenyl, carboalkoxy, carboaryloxy, mercapto, alkylthio, benzylthio and acylthio.

2. A compound according to claim 1 in which $R^2$ is $CH_2NHR^1$ in which $R^1$ is methyl or ethyl; $R^3$ is $C_{1-3}$alkyl; $R^5$ and $R^7$ are chloro; and X is O or the pharmaceutically acceptable salts thereof.

3. A compound according to claim 2 in which $R^2$ is $CH_2NHR^1$ in which $R^1$ is methyl or ethyl; $R^3$ is $C_{2-3}$alkyl; $R^5$ and $R^7$ are chloro; and X is O or the pharmaceutically acceptable salts thereof.

4. A compound according to claim 2 in which $R^2$ is $CH_2NHR^1$ in which $R^1$ is methyl or ethyl; $R^3$ is methyl; $R^5$ and $R^7$ are chloro; and X is O or the pharmaceutically acceptable salts thereof.

5. A pharmaceutical or veterinary composition comprising an effective amount of the compound of formula I as defined in claim 1 or pharmaceutically acceptable salts, tautomers, or stereoisomers thereof and a pharmaceutically or veterinarily acceptable carrier.

* * * * *